United States Patent
Kawabata et al.

(10) Patent No.: US 9,429,572 B2
(45) Date of Patent: Aug. 30, 2016

(54) COMPLEX FORMATION METHOD AND SEPARATION METHOD

(75) Inventors: Tomohisa Kawabata, Hyogo (JP); Shinji Satomura, Hyogo (JP); Henry Garrett Wada, Atherton, CA (US)

(73) Assignee: WAKO PURE CHEMICAL INDUSTRIES, LTD., Osaka (JP)

(*) Notice: Subject to any disclaimer, the term of this patent is extended or adjusted under 35 U.S.C. 154(b) by 1388 days.

(21) Appl. No.: 11/991,170

(22) PCT Filed: Aug. 24, 2006

(86) PCT No.: PCT/US2006/033043
§ 371 (c)(1),
(2), (4) Date: Feb. 28, 2008

(87) PCT Pub. No.: WO2007/027495
PCT Pub. Date: Mar. 8, 2007

(65) Prior Publication Data
US 2009/0152114 A1   Jun. 18, 2009

Related U.S. Application Data

(60) Provisional application No. 60/713,346, filed on Sep. 2, 2005.

(51) Int. Cl.
| | |
|---|---|
| G01N 33/48 | (2006.01) |
| G01N 33/50 | (2006.01) |
| G01N 33/561 | (2006.01) |
| C12M 1/00 | (2006.01) |
| G06F 19/00 | (2011.01) |
| G06F 19/18 | (2011.01) |
| C12M 3/06 | (2006.01) |
| G01N 33/53 | (2006.01) |
| G01N 33/536 | (2006.01) |
| G01N 33/537 | (2006.01) |

(52) U.S. Cl.
CPC .......... *G01N 33/561* (2013.01); *C12M 23/16* (2013.01); *C12M 45/07* (2013.01); *G01N 33/5306* (2013.01); *G01N 33/536* (2013.01); *G01N 33/5375* (2013.01); *G06F 19/18* (2013.01); *G06F 19/702* (2013.01); *Y10S 977/705* (2013.01)

(58) Field of Classification Search
None
See application file for complete search history.

(56) References Cited

U.S. PATENT DOCUMENTS

| | | | | |
|---|---|---|---|---|
| 5,348,633 | A * | 9/1994 | Karger et al. | 204/452 |
| 5,958,202 | A | 9/1999 | Regnier et al. | |
| 7,842,175 | B2 * | 11/2010 | Kawabata et al. | 204/450 |
| 2004/0118688 | A1 * | 6/2004 | Dumas | 204/548 |
| 2005/0003362 | A1 | 1/2005 | Krylov et al. | |
| 2009/0152114 | A1 * | 6/2009 | Kawabata et al. | 204/451 |

FOREIGN PATENT DOCUMENTS

EP   0 103 965   *   3/1984

OTHER PUBLICATIONS

Chu et al. Affinity capillary electrophoresis can simultaneously measure binding constants of multiple peptides to vancomycin. Journal of Organic Chemistry, vol. 57, 1992, pp. 3524-3525.*
Mammen et al. Determination of the binding of ligands containing the N-2,4-dinitrophenyl group to bivalent monoclonal rat anti-DNP antibody using affinity capillary electrophoresis. Analytical Chemistry, vol. 67, 1995, pp. 3526-3535.*
Watzig et al. Capillary electrophoresis—a high performance analytical separation technique. Clinical Chemistry Laboratory Medicine, vol. 41, 2003, pp. 724-738.*
Schrader et al. Progesterone-binding components of chick oviduct. The Journal of Biological Chemistry, vol. 247, 1972, pp. 51-59.*
Everaerts et al. Determination of substances at low concentrations in complex mixtures by isotachophoresis with column coupling. Journal of Chromatography, vol. 169, 1979, pp. 21-38.*
Isotachophoresis, 2 pages, 2011. Dorland's Illustrated Medical Dictionary. Retrieved online on Aug. 3, 2014 from <<http://www.credoreference.com>>.*
Chu et al. Affinity capillary electrophoresis can simultaneously measure binding constants of multiple peptides to vancomycin. Journal of Organic Chemistry, 1992, vol. 57, pp. 3524-3525.*
Chu et al. Affinity capillary electrophoresis. Acc. Chem. Res., 1995, vol. 28, pp. 461-468.*
Kawabata et al., "Liquid-Phase Binding Assay of α0Fetoprotein Using DNA-Coupled Antibody and Capillary Chip Electrophoresis," Anal. Chem., 2005, 77:5579-5582.
Kiessig et al.,"Interaciton of cyclophilin and cyclosporins monitored by affinity capillary electrophoresis," Journal of Chromatography A, 1999, 853:469-477.
Priego-Capote et al., "Dual injection capillary electrophoresis: Foundations and appliations," Electrophoresis, 2004, 25:4074-4085.
Van Dyck et al., "Advances in capillary electrophoretically mediated microanalysis," Electrophoresis, 2003, 24:3868-3878.

* cited by examiner

*Primary Examiner* — Russell S Negin
(74) *Attorney, Agent, or Firm* — Finnegan, Henderson, Farabow, Garrett & Dunner LLP

(57) ABSTRACT

An object of the present invention is to provide a method for forming a complex between an analyte or an analog thereof, and a substance formable the complex with said analyte or said analog thereof (the complex forming substance), in a short time and in high reaction efficiency, and a method for separating a complex formed, and a complex forming substance not involved in formation of said complex or an analog not involved in formation of said complex rapidly, simply and in high accuracy, along with a method for measuring an analyte in a sample in high sensitivity.

19 Claims, 4 Drawing Sheets

COMPLEX FORMATION METHOD AND SEPARATION METHOD

CROSS-REFERENCE TO RELATED APPLICATIONS

This application is a National Stage application of PCT/US2006/033043, filed Aug. 24, 2006, which claims priority from U.S. Provisional Application No. 60/713,346, filed Sep. 2, 2005.

BACKGROUND OF THE INVENTION

1. Technical Field

The present invention relates to a method for forming a complex between an analyte or an analogue thereof in a sample, and a substance formable a complex with said analyte or analogue thereof (hereinafter, abbreviated as a complex forming substance or CFS), a method for separating a complex formed, and a CFS or an analogue not involved in formation of said complex, along with a method for measuring an analyte in a sample, based on the amount of a complex separated, or the amount of a CFS or an analogue not involved in formation of a complex.

2. Background Art

Analysis of an analyte in a sample usually requires mixing a plurality of solutions such as a sample and various reagent solutions (for example, a reagent solution including an antibody to an analyte, a reagent solution containing a labeling substance, and the like) etc., and subjecting an analyte in a sample and a reactant in a reagent solution (an antibody to an analyte or a labeling substance, and the like) to a reaction.

In Micro Total Analysis System (µ-TAS) using micro fluidics device, wherein, technology thereof has recently been developing and various researches thereon have been made, a method for mixing these plurality of solutions in advance and subjecting to a reaction outside a capillary (channel), then introducing the mixed solution into a capillary (channel), or a method for simultaneously introducing a plurality of solutions into a mixing capillary (channel) to carry out mixing and reaction (Patent Literature 1) has been known.

However, in the former method, a sample or a reagent solution in the amount of micro litter (µl) order is required for mixing in advance, which loses merit of µ-TAS, namely possibility of micro analysis of a sample or a reagent solution in the amount of from nano litter (nl) to pico litter (pl) order. In addition, in the latter method, laminar flow generating in a capillary in introduction makes mixing of a plurality of solutions difficult, resulting in requirement to depend on molecular diffusion, which poses such a problem as, in the case of mixing a plurality of solutions with different molecular weight or viscosity, the variation of complete mixing time of these solutions due to variation of diffusion coefficient, or variation in viscosity ratio of solutions to be mixed varies volume ratio of a plurality of solutions to be introduced in a channel, which results in variation of mixing ratio depending on kinds of solutions to be mixed, which poses a problem of making mixing in constant mixing ratio impossible.

In addition, as a method other than the above, there are methods disclosed in Bao, J. M, Regnier, F. E, J. Chromatogr. 1992, 608, 217-224 (Non-Patent Literature 1) or JP-A-10-512371 (Patent Literature 2).

In these methods, in a capillary for analysis, a solution including a molecule with higher electrophoretic mobility is arranged at the backward of a solution containing a molecule with lower electrophoretic mobility, so that a molecule with higher electrophoretic mobility overtakes a molecule with lower electrophoretic mobility, by application of electric field, by which a reaction between these molecules themselves is carried out. These methods make possible molecular mixing uniformly and in a short time compared with conventional mixing methods depending on molecular diffusion.

However, these methods are not satisfactory in reaction efficiency, and countermeasures to ensure sufficient reaction efficiency is required to detect an analyte in a sample in high sensitivity, for example, to increase concentration of molecules to be fed to a reaction, or to longer reaction time by delaying molecular movement rate by electrophoresis.

Patent Literature 1: JP-A-2005-31070
Patent Literature 2: JP-A-10-512371
Non-Patent Literature 1: Bao, J. M, Regnier, F. E, J. Chromatogr. 1992, 608, 217-224

DISCLOSURE OF THE INVENTION

Problems to be Solved by the Invention

The present invention relates to a method for forming a complex between said analyte or analogue thereof, and said CFS in a short time and in high reaction efficiency, a method for separating a complex formed, and a CFS or an analogue not involved in formation of said complex quickly, easily and with a high degree of accuracy, along with a method for measuring an analyte in a sample in high sensitivity.

Means for Solving Problems

The present invention is composed of the following framework:

1. A Method for Forming a Complex Comprising the Following Steps:
    (1) a step of arranging (a) a solution containing an analyte or an analogue thereof and (b) a solution containing not less than one kind of a CFS, in a capillary, so that by applying a voltage to said capillary the complex between said analyte or said analogue thereof and the CFS are formed without mixing these solutions in advance; and
    (2) a step of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS.

2. A Method for Separating a Complex Comprising the Following Steps:
    (1) a step of arranging (a) a solution containing an analyte or an analogue thereof and (b) a solution containing not less than one kind of a CFS, in a capillary, so that by applying a voltage to said capillary the complex between said analyte or said analogue thereof and the CFS are formed without mixing these solutions in advance;
    (2) a step of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS; and (3) a step of separating said complex, and the CFS not involved in the formation of said complex or the analogue not involved in the formation of said complex by further electrical movement.

3. A Method for Measuring an Analyte Comprising the Following Steps:

(1) a step of arranging (a) a solution containing an analyte or an analogue thereof and (b) a solution containing not less than one kind of a CFS, in a capillary, so that by applying a voltage to said capillary the complex between said analyte or said analogue thereof and the CFS are formed without mixing these solutions in advance;

(2) a step of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS;

(3) a step of separating said complex, and the CFS not involved in the formation of said complex or the analogue not involved in the formation of said complex by further electrical movement; and (4) a step of measuring the amount of thus separated complex, or the amount of the CFS or the analogue not involved in the formation of said complex to determine the amount of said analyte based on the result.

Namely, the present inventors found that by arranging a solution containing an analyte or an analogue thereof, and a solution containing a CFS, in a channel, without mixing these solutions in advance, to form a complex between said analyte and analogue, and CFS while concentrating said analyte or analogue thereof and/or CFS electrophoretically by applying a voltage onto this capillary, by utilization of difference in electrophoretic mobility, said complex can be formed in a short time and in high reaction efficiency by using only ultra small amount of a sample and said solution from nano litter (nl) to pico litter (pl) order, and without taking consideration on variation in mixing ratio caused by difference in viscosity of a sample and said solution, and have thus completed the present invention.

Effect of the Invention

In accordance with a method of the present invention, a reaction between an analyte or an analogue thereof in a solution and a CFS in a solution, can be carried out in a short time and in high reaction efficiency. As a result, separation of a complex with a CFS, and a CFS or an analogue not involved in formation of a complex becomes possible rapidly, simply and in high accuracy, and furthermore, high sensitivity measurement of an analyte in a sample becomes possible, based on the amount of separated complex or the amount of a CFS or analogue not involved in formation of a complex.

BEST MODES FOR CARRYING OUT THE INVENTION

1. A Method for Forming a Complex of the Present Invention

A method of the present invention is characterized in that (a) a solution containing an analyte or an analogue thereof, and a solution containing a CFS are introduce and arranged into each separate zone in a capillary, without forming a complex between them by mixing these solutions in advance outside a capillary, and subsequently (b) a complex between said analyte or analogue thereof and CFS is formed while concentrating said analyte or analogue thereof and/or CFS electrophoretically to make contact these by applying a voltage onto said channel, before uniformly mixing these solutions in a capillary A method for forming a complex of the present invention specifically comprises the following step (1) and step (2):

(1) a step (a step of introduction) of arranging (a) a solution containing an analyte or an analogue thereof and (b) a solution containing not less than one kind of a CFS with said analyte or said analogue thereof, in a capillary, so that by applying a voltage to said capillary the complex between said analyte or said analogue thereof and the CFS are formed without mixing these solutions in advance; and (2) a step (a step of concentrating reaction) of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS.

1-1. A Step of Introduction [a Step (1)]

A step (1) of the present invention is a step of introducing and arranging a solution containing an analyte or an analogue thereof, and solutions containing not less than one kind of CFSs into a capillary, so that a complex between an analyte or an analogue thereof and a CFS is formed, without mixing these solutions in advance outside a capillary, and by applying a voltage onto a capillary, namely by carrying out a step (2) of the present invention as described later.

Here, "so that a complex between an analyte or an analogue thereof and a CFS is formed, by applying a voltage onto a capillary" means to form a complex between an analyte or an analogue thereof and a CFS by contacting the analyte or analogue thereof with the CFS, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed) and electrophoresis is carried out, a substance with higher electrophoretic mobility (faster electrophoretic speed) in a solution overtakes a substance with lower electrophoretic mobility (slow electrophoretic speed).

Namely, the present invention aims at forming a complex between (1) an analyte or an analogue thereof, or a complex between an analyte or an analogue thereof, and a certain CFS, and (2) at least one kind of a CFS (note: a CFS different from one described above) in a capillary by applying a voltage onto a capillary. In other words, the present invention includes not only the case that a complex between an analyte or an analogue thereof, and all of CFSs is formed only in a capillary, but also such a case is also included, for example, that when 2 or more kinds of CFSs are used, a complex (an intermediate complex) between an analyte or an analogue thereof, and a part of CFSs among 2 or more kinds of CFSs is formed in advance outside a capillary, or in a capillary without application of a voltage, and subsequently said intermediate complex and residual not less than one kind of CFSs are made contacted in a capillary by applying a voltage onto a capillary, to form a complex between the intermediate complex formed in advance, and the residual not less than one kind of CFSs.

For example, when 2 kinds of CFSs are used, such a case is naturally included that (1) a complex (an intermediate complex) between an analyte or an analogue thereof and one kind of a CFS, and a complex between said intermediate complex and a residual one kind of a CFS is formed in a capillary by applying a voltage onto a capillary, and such a case is also included that (2) an intermediate complex between an analyte or an analogue thereof, and a kind of a CFS is formed in advance outside a capillary, or in a capillary without application of a voltage, and subsequently said intermediate complex and a residual one kind of a CFS is formed in a capillary by applying a voltage onto a capillary. In addition, for example, when 3 kinds of CFSs are used, the case is naturally included that (1) a complex (an intermediate complex 1) between an analyte or an analogue thereof and one kind of a CFS (a CFS-1), a complex (an intermediate complex 2) between said intermediate complex 1 and the residual one kind of a CFS (a CFS-2), and a complex between the intermediate complex 2 and residual one kind of a CFS (a CFS-3) are formed in a capillary by applying a voltage onto a capillary, and such cases are also included that (2) an intermediate complex 1 between an analyte or an analogue thereof, and a CFS-1 is formed in advance outside a capillary, or in a capillary without application of a voltage, and then an intermediate complex 2 between said intermediate complex 1 and a CFS-2, along with a complex between said intermediate complex 2 and a CFS-3 are formed in a capillary by applying a voltage onto a capillary; or (3) an intermediate complex 1 between an analyte or an analogue thereof and a CFS-1, and an intermediate complex 2 between said intermediate complex 1 and a CFS-2 are formed in advance outside a capillary, or in a capillary without application of a voltage, and then, a complex between said intermediate complex 2 and a CFS-3 is formed in a capillary by applying a voltage onto a capillary. (In this connection, the cases when 4 or more kinds of CFSs are used are considered by the same way of thinking.)

Therefore, in the present invention, "without mixing solutions in advance" means no mixing of a solution containing an analyte or an analogue thereof, and a solution containing at least one kind of a CFS in advance, but does not necessarily mean exclusion of any mixing of a solution containing an analyte or an analogue thereof, and a solution containing at least one kind of a CFS in advance (in other words, it does not mean never to do to mix some of a sample including an analyte and solutions containing all of CFSs, along with if necessary, a solution containing analogues).

In the present invention, a direction toward which a complex between an analyte or an analogue thereof, and not less than one kind of CFSs, finally formed when voltage is applied, moves is defined as "downstream" side, and the opposite direction is defined as "upstream" side (the same hereinafter).

In addition, in the present invention, "electrophoretic speed (of an analyte or an analogue thereof, a CFS, and the like are subjected to electrophoresis) is "slow" or "electrophoretic mobility (of an analyte or an analogue thereof, a CFS, and the like are subjected to electrophoresis) is low" means not only the case when electrophoretic speed is slow (electrophoretic mobility is low) than those of at least not less than one kind other substances, but also means movement in a direction opposite to the direction of at least not less than one kind other substances.

Arrangement order of a solution containing an analyte or an analogue thereof, and solutions including not less than one kind of CFSs is not especially limited, as long as it is an order formable a complex between an analyte or an analogue thereof, and a CFS by applying a voltage onto a capillary.

In Tables 1-1 to 1-5, relations between arrangement order of a solution containing an analyte or an analogue thereof and a solution including a CFS, and electrophoretic mobility (electrophoretic speed) of an analyte or an analogue thereof, and a CFS are shown, however, the present invention is by no means limited thereto.

In this connection, in Tables 1-1 to 1-5, the cases when from one kind to 3 kinds of CFSs are used are shown, however, the same way of thinking as in Tables 1-1 to 1-5 is applied in suitable arrangement, also in the case when 4 or more kinds of CFSs are used.

In Tables 1-1 to 1-5, Ana represents an analyte or an analogue thereof, CFS-1 represents a CFS-1, CFS-2 represents a CFS-2, and CFS-3 represents a CFS-3. In addition, in Tables 1-1 to 1-5, arrangement order A in a capillary is a zone of a solution arranged at the most upstream side, among a solution containing an analyte or an analogue thereof, and solutions including not less than one kind of CFSs, B is a zone of a solution arranged at the downstream side of zone A, C is a zone of a solution arranged at the downstream side of zone B, and D is a zone of a solution arranged at the downstream side of zone C. In this connection, the arrangement orders (A to D) in said capillary is only the orders among a solution containing an analyte or an analogue thereof, and solutions including not less than one kind of CFSs, and such arrangement may naturally be allowed that a solution, and the like, other than said solutions is arranged at further downstream side of said solution arranged at the most downstream side among these, or at further upstream side of said solution arranged at the most upstream side.

TABLE 1-1

| Pattern | Arrangement order in capillary (Upstream→Downstream) | | | | Relationship of Electorophoretic Mobility between Ana and CFS |
|---|---|---|---|---|---|
| | A | B | C | D | |
| 1 | Solution containing Ana | Solution containing CFS-1 | — | — | Ana > CFS-1 |
| 2 | Solution containing CFS-1 | Solution containing Ana | — | — | Ana < CFS-1 |
| 3 | Solution containing Ana | Solution containing CFS-1 | Solution containing CFS-2 | — | (1) Ana > CFS-1; (Ana/CFS-1)complex > CFS-2 However, (Ana/CFS-1)complex is formed prior to (Ana/CFS-2)complex. |

TABLE 1-1-continued

| Pattern | Arrangement order in capillary (Upstream→Downstream) | | | | Relationship of Electorophoretic Mobility between Ana and CFS |
|---|---|---|---|---|---|
| | A | B | C | D | |
| 4 | | | | | (2) CFS-1 > Ana > CFS-2; (Ana/CFS-2)complex > CFS-1 However, (Ana/CFS-2)complex is formed prior to (Ana/CFS-1)complex. |
| 5 | Solution containing CFS-1 | Solution containing Ana | Solution containing CFS-2 | — | (1) Ana < CFS-1; (Ana/CFS-1)complex > CFS-2 However, (Ana/CFS-1)complex is formed prior to (Ana/CFS-2)complex. |
| 6 | | | | | (2) Ana > CFS-2; (Ana/CFS-2)complex < CFS-1 However, (Ana/CFS-2)complex is formed prior to (Ana/CFS-1)complex. |
| 7 | Solution containing CFS-1 | Solution containing CFS-2 | Solution containing Ana | — | (1) CFS-2 < CFS-1; Ana < CFS-1(Ana/CFS-1)complex < CFS-2 However, (Ana/CFS-1)complex is formed prior to (Ana/CFS-2)complex. |
| 8 | | | | | (2) Ana < CFS-2; (Ana/CFS-2)complex < CFS-1 However, (Ana/CFS-2)complex is formed prior to (Ana/CFS-1)complex. |

TABLE 1-2

| 9 | Solution containing Ana | Solution containing CFS-1 | Solution containing CFS-2 | Solution containing CFS-3 | (1) Ana > CFS-1; (Ana/CFS-1)complex > CFS-2; (Ana/CFS-1/CFS-2) complex > CFS-3 However, (Ana/CFS-1)complex is formed prior to (Ana/CFS-2)complex and (Ana/CFS-3)complex, (Ana/CFS-1/CFS-2)complex is formed prior to(Ana/CFS-1/CFS-3)complex. |
|---|---|---|---|---|---|
| 10 | | | | | (2) Ana > CFS-1; CFS-2 > (Ana/CFS-1)complex > CFS-3; (Ana/CFS-1/CFS-3)complex > CFS-2 However, (Ana/CFS-1)complex is formed prior to (Ana/CFS-2)complex and (Ana/CFS-3)complex, (Ana/CFS-1/CFS-3)complex is formed prior to (Ana/CFS-1/CFS-2)complex. |
| 11 | | | | | (3) CFS-1 > Ana > CFS-2; (Ana/CFS-2)complex > CFS-1; (Ana/CFS-2/CFS-1)complex > CFS-3 However, (Ana/CFS-2)complex is formed prior to (Ana/CFS-1)complex and (Ana/CFS-3)complex, (Ana/CFS-2/CFS-1)complex is formed prior to (Ana/CFS-2/CFS-3)complex. |
| 12 | | | | | (4) CFS-1 > Ana > CFS-2; CFS-1 > (Ana/CFS-2)complex > CFS-3; (Ana/CFS-2/CFS-3)complex > CFS-1 However, (Ana/CFS-2)complex is formed prior to (Ana/CFS-1)complex and (Ana/CFS-3)complex, (Ana/CFS-2/CFS-3)complex is formed prior to(Ana/CFS-2/CFS-1)complex. |
| 13 | | | | | (5) CFS-1, CFS-2 > Ana > CFS-3; (Ana/CFS-3)complex > CFS-1; (Ana/CFS-3/CFS-1)complex > CFS-2 However, (Ana/CFS-3)complex is formed prior to (Ana/CFS-1)complex and (Ana/CFS-2)complex, (Ana/CFS-3/CFS-1)complex is formed prior to (Ana/CFS-3/CFS-2)complex. |
| 14 | | | | | (6) CFS-1, CFS-2 > Ana > CFS-3; CFS-1 > (Ana/CFS-3)complex > CFS-2; (Ana/CFS-3/CFS-2)complex > CFS-1 |

TABLE 1-2-continued

|   |   |   |   | However, (Ana/CFS-3)complex is formed prior to (Ana/CFS-1)complex and (Ana/CFS-2)complex, (Ana/CFS-3/CFS-2)) complex is formed prior to (Ana/CFS-3/CFS-1)complex. |
|---|---|---|---|---|

TABLE 1-3

| | | | | |
|---|---|---|---|---|
| 15 | Solution containing CFS-1 | Solution containing Ana | Solution containing CFS-2 | Solution containing CFS-3 | (1) Ana < CFS-1; (Ana/CFS-1)complex > CFS-2; (Ana/CFS-1/CFS-2)complex > CFS-3 However, (Ana/CFS-1)complex is formed prior to (Ana/CFS-2)complex and (Ana/CFS-3)complex, (Ana/CFS-1/CFS-2)complex is formed prior to (Ana/CFS-1/CFS-3)complex. |
| 16 | | | | | (2) Ana < CFS-1; CFS-2 > (Ana/CFS-1)complex > CFS-3; (Ana/CFS-1/CFS-2)complex > CFS-3 However, (Ana/CFS-1)complex is formed prior to (Ana/CFS-2)complex and (Ana/CFS-3)complex, (Ana/CFS-1/CFS-3)complex is formed prior to(Ana/CFS-1/CFS-2)complex. |
| 17 | | | | | (3) Ana > CFS-2; (Ana/CFS-2)complex < CFS-1; (Ana/CFS-2/CFS-1)complex > CFS-3 However, (Ana/CFS-2)complex is formed prior to (Ana/CFS-1)complex and (Ana/CFS-3)complex, (Ana/CFS-2/CFS-1)complex is formed prior to (Ana/CFS-2/CFS-3)complex. |
| 18 | | | | | (4) Ana > CFS-2; (Ana/CFS-2)complex > CFS-3; (Ana/CFS-2/CFS-3)complex < CFS-1 However, (Ana/CFS-2)complex is formed prior to (Ana/CFS-1)complex and (Ana/CFS-3)complex, (Ana/CFS-2/CFS-3)complex is formed prior to (Ana/CFS-2/CFS-1)complex. |
| 19 | | | | | (5) CFS-2 > Ana > CFS-3; (Ana/CFS-3)complex < CFS-1; (Ana/CFS-3/CFS-1)complex > CFS-2 However, (Ana/CFS-3)complex is formed prior to (Ana/CFS-1)complex and (Ana/CFS-2)complex, (Ana/CFS-3/CFS-1)complex is formed prior to (Ana/CFS-3/CFS-2)complex. |
| 20 | | | | | (6) CFS-2 > Ana > CFS-3; (Ana/CFS-3)complex > CFS-2; (Ana/CFS-3/CFS-2)complex < CFS-1 However, (Ana/CFS-3)complex is formed prior to (Ana/CFS-1)complex and (Ana/CFS-2)complex, (Ana/CFS-3/CFS-2)complex is formed prior to (Ana/CFS-3/CFS-1)complex. |

TABLE 1-4

| | | | | |
|---|---|---|---|---|
| 21 | Solution containing CFS-1 | Solution containing CFS-2 | Solution containing Ana | Solution containing CFS-3 | (1) CFS-2 < CFS-1; Ana < CFS-1; (Ana/CFS-1)complex < CFS-2; (Ana/CFS-1/CFS-2)complex > CFS-3 However, (Ana/CFS-1)complex is formed prior to (Ana/CFS-2)complex and (Ana/CFS-3)complex, (Ana/CFS-1/CFS-2)complex is formed prior to(Ana/CFS-1/CFS-3)complex. |
| 22 | | | | | (2) CFS-2 < CFS-1; Ana < CFS-1; (Ana/CFS-1)complex > CFS-3; (Ana/CFS-1/CFS-3)complex < CFS-2 However, (Ana/CFS-1)complex is formed prior to (Ana/CFS-2)complex and (Ana/CFS-3)complex, |

TABLE 1-4-continued

| | | |
|---|---|---|
| 23 | | (Ana/CFS-1/CFS-3)complex is formed prior to (Ana/CFS-1/CFS-2)complex.<br>(3) Ana < CFS-2;<br>(Ana/CFS-2)complex < CFS-1;<br>(Ana/CFS-2/CFS-1)complex > CFS-3<br>However, (Ana/CFS-2)complex is formed prior to (Ana/CFS-1)complex and (Ana/CFS-3)complex,<br>(Ana/CFS-2/CFS-1)complex is formed prior to (Ana/CFS-2/CFS-3)complex. |
| 24 | | (4) Ana < CFS-2:<br>(Ana/CFS-2)complex > CFS-3;<br>(Ana/CFS-2/CFS-3)complex > CFS-1<br>However, (Ana/CFS-2)complex is formed prior to (Ana/CFS-1)complex and (Ana/CFS-3)complex,<br>(Ana/CFS-2/CFS-3)complex is formed prior to (Ana/CFS-2/CFS-1) complex. |
| 25 | | (5) Ana > CFS-3;<br>CFS-1 > CFS-2;<br>(Ana/CFS-3)complex < CFS-1;<br>(Ana/CFS-3/CFS-1)complex < CFS-2<br>However, (Ana/CFS-3)complex is formed prior to (Ana/CFS-1)complex and (Ana/CFS-2)complex,<br>(Ana/CFS-3/CFS-1)complex is formed prior to(Ana/CFS-3/CFS-2)complex. |
| 26 | | (6) Ana > CFS-3;<br>(Ana/CFS-3)complex < CFS-2;<br>(Ana/CFS-3/CFS-2)complex < CFS-1<br>However, (Ana/CFS-3)complex is formed prior to (Ana/CFS-1)complex and (Ana/CFS-2)complex,<br>(Ana/CFS-3/CFS-2)complex is formed prior to (Ana/CFS-3/CFS-1)complex. |

TABLE 1-5

| | Solution containing CFS-1 | Solution containing CFS-2 | Solution containing CFS-3 | Solution containing Ana | |
|---|---|---|---|---|---|
| 27 | Solution containing CFS-1 | Solution containing CFS-2 | Solution containing CFS-3 | Solution containing Ana | (1) CFS-1 > CFS-2, CFS-3, Ana;<br>CFS-2 > CFS-3;<br>(Ana/CFS-1)complex < CFS-2;<br>(Ana/CFS-1/CFS-2)complex < CFS-3<br>However, (Ana/CFS-1)complex is formed prior to (Ana/CFS-2)complex and (Ana/CFS-3)complex,<br>(Ana/CFS-1/CFS-2)complex is formed prior to (Ana/CFS-1/CFS-3)complex. |
| 28 | | | | | (2) CFS-1 > CFS-2, CFS-3, Ana;<br>(Ana/CFS-1)complex < CFS-3;<br>(Ana/CFS-1/CFS-3)complex < CFS-2<br>However, (Ana/CFS-1)complex is formed prior to (Ana/CFS-2)complex and (Ana/CFS-3)complex,<br>(Ana/CFS-1/CFS-3)complex is formed prior to (Ana/CFS-1/CFS-2)complex. |
| 29 | | | | | (3) CFS-2 > CFS-1, CFS-3, Ana;<br>CFS-1 > CFS-3;<br>(Ana/CFS-2)complex < CFS-1;<br>(Ana/CFS-2/CFS-1)complex < CFS-3<br>However, (Ana/CFS-2)complex is formed prior to (Ana/CFS-1)complex and (Ana/CFS-3)complex,<br>(Ana/CFS-2/CFS-1)complex is formed prior to (Ana/CFS-2/CFS-3)complex. |
| 30 | | | | | (4) CFS-2 > CFS-1, CFS-3, Ana;<br>(Ana/CFS-2)complex < CFS-1;<br>(Ana/CFS-2/CFS-3)complex < CFS-1<br>However, (Ana/CFS-2)complex is formed prior to (Ana/CFS-1)complex and (Ana/CFS-3)complex,<br>(Ana/CFS-2/CFS-3)complex is formed prior to (Ana/CFS-2/CFS-1)complex. |
| 31 | | | | | (5) CFS-3 > Ana;<br>CFS-1 > CFS-3;<br>(Ana/CFS-3)complex < CFS-1;<br>(Ana/CFS-3/CFS-1)complex < CFS-2<br>However, (Ana/CFS-3)complex is |

TABLE 1-5-continued

| | |
|---|---|
| 32 | formed prior to (Ana/CFS-1)complex and (Ana/CFS-2)complex, (Ana/CFS-3/CFS-1)complex is formed prior to (Ana/CFS-3/CFS-2)complex. (6) CFS-3 > Ana; (Ana/CFS-3)complex < CFS-2; (Ana/CFS-3/CFS-2)complex < CFS-1 However, (Ana/CFS-3)complex is formed prior to (Ana/CFS-1)complex and (Ana/CFS-2)complex, (Ana/CFS-3/CFS-2)complex is formed prior to (Ana/CFS-3/CFS-1)complex. |

In Tables 1-1 to 1-5, "formed prior to" means that the former complex is formed substantially before the latter complex is formed, but does not exclude when a part of the former complex and the latter complex are formed simultaneously or in reversed order, for example, in the following case.

(1) The case that by adjacently placing each zone (zone of a solution containing an analyte or an analogue thereof, zone of solutions containing CFSs) and by molecular diffusion generated at the vicinity of liquid-liquid interface between each zone among these, a part of the former complex and the latter complex are formed simultaneously or in reversed order.

(2) The case that from the relation of electrophoretic speed of an analyte or an analogue thereof and not less than one kind of CFSs, a part of the former complex and the latter complex are formed simultaneously or in reversed order.

(3) The case that because at least one kind of a CFS among an analyte or an analogue thereof and not less than one kind of CFSs move in a direction opposite from those of other substances, a part of the former complex and the latter complex are formed simultaneously or in reversed order.

In such cases, a solution containing an analyte or an analogue thereof, and solutions containing CFSs may suitably be arranged by the same way of thinking as in Tables 1-1 to 1-5.

In addition, for the case when 2 or more kinds of CFSs are used, among the cases in Tables 1-1 to 1-5, such a case is shown that all of CFSs (a CFS-1 to -3) bind to an analyte or an analogue thereof, namely all of the binding sites of 2 or more kinds of CFSs are present only at an analyte or an analogue thereof [binding form (1): a sandwich complex with Ana sandwiched by CFS-1 and CFS-2]. The following other cases may be understood as follows: A case, for example, a CFS-1 in 2 kinds of CFSs (a CFS-1 and -2) binds to an analyte or an analogue thereof, and a CFS-2 binds to new sites generated by formation of a complex between an analyte or an analogue thereof, and a CFS-1, in other words, binding sites of at least one kind of a CFS (for example, a CFS A) among 2 or more kinds of CFSs are present only on an analyte or an analogue thereof, and binding sites of other at least one kind of a CFS (for example, a CFS B) are present at new sites generated by formation of a complex between an analyte or an analogue thereof, and a CFS A, [binding form (2)]; or a case, for example, a CFS-1 in 2 kinds of CFSs (a CFS-1 and -2) binds to an analyte or an analogue thereof, and a CFS-2 binds to a CFS-1 bound with an analyte or an analogue thereof, in other words, binding sites of at least one kind of a CFS (for example, a CFS A) among 2 or more kinds of CFSs are present only on an analyte or an analogue thereof, and binding sites of other at least one kind of a CFS (for example, a CFS B) are present only on a CFS A, [binding form (3)]; are the cases when a sandwich complex of CFS-1, sandwiched by Ana and CFS-2, is formed in the binding form (1) [an analyte or an analogue thereof in the case of using 2 kinds of CFSs in Tables 1-1 to 1-5 is alternatively read as a CFS-1, and a CFS-1 in Tables 1-1 to 1-5 is alternatively read as an analyte or an analogue thereof]. In addition, in such cases as 3 kinds or more CFSs are used in the above-described binding forms (2) and (3), or such cases as the above-described binding forms (1) to (3) are suitably combined, a solution containing an analyte or an analogue thereof, and solutions containing CFSs may suitably be arranged by the same way of thinking as in Tables 1-1 to 1-5 and the above.

In this connection, in carrying out the present invention in a competitive method using an analogue of an analyte, any of the following arrangements may also be adopted; An analyte in a sample (namely, a sample including an analyte) and an analogue [for example, an analogue labeled by a labeling substance (a labeled analogue), and an analogue bound with a reaction improvement substance (a reaction improvement analogue)], are simultaneously present in the same solution and introduced and arranged into a capillary as one solution zone (namely, a zone of a solution containing a sample including an analyte and an analogue); a sample including an analyte, and a solution containing an analogue (for example, a labeling analogue or a reaction improvement analogue) are introduced and arranged into a capillary as each separate zone (solution); or a solution containing an analyte in a sample (namely, a sample including an analyte) and not less than one kind of CFSs, and a solution including an analogue (for example, a labeled analogue or a reaction improvement analogue) are introduced and arranged into a capillary as each separate zone (solution).

In this connection, in the above-described competitive method, to arrange, in a capillary, (1) a solution including a sample having an analyte and a labeled analogue (a solution containing an analyte and an analogue), along with solutions containing not less than one kind of CFSs (a CFS, a reaction improvement CFS and combinations thereof); or (2) a sample including an analyte (a solution containing an analyte or an analogue thereof), along with a solution containing a labeled analogue and solutions including not less than one kind of CFSs (a CFS, a reaction improvement CFS and combinations thereof); or (3) a solution including a sample having an analyte and not less than one kind of CFSs (a CFS, a reaction improvement CFS and combinations thereof), along with a solution containing a labeled analogue; so that a complex A between said analyte and CFS, and a complex B between said labeled analogue and CFS are formed by applying a voltage onto a channel, arrangement order of these solutions may be determined, in accordance with arrangement order of a solution including an analyte or an analogue thereof, and solutions containing not less than one kind of CFSs, as explained above, by consideration on electrophoretic mobility of an analyte, a labeled analogue and a CFS. In addition, to arrange, in a capillary, (1) a solution including a sample having an analyte and a reaction improvement analogue (a solution containing an analyte and an analogue), along with a solution containing not less than one kind of a CFS having property capable of forming a complex with an analyte or an analogue thereof and labeled with a labeling substance (hereinafter, abbreviated as a labeled binding substance or a labeled CFS); or (2) a sample including an analyte (a solution containing an analyte or an analogue), along with a solution including a reaction improvement analogue and a solution containing not less than one kind of labeled CFSs; or (3) a solution including a sample having an analyte and not less than one kind of labeled CFSs, along with a solution containing a reaction improvement analogue; so that a complex A between said analyte and labeled CFS, and a complex B between said reaction improvement analogue and labeled CFS are formed by applying a voltage onto a capillary, arrangement order of these solutions may be determined, in accordance with arrangement order of a solution containing an analyte or an analogue thereof, and solutions including not less than one kind of CFSs, as explained above, by consideration on electrophoretic mobility of an analyte, a reaction improvement analogue and a labeled CFS.

In addition, a solution containing an analyte or an analogue thereof, and solutions containing not less than one kind of CFSs are not necessarily made adjacent, and liquid such as water, a physiological salt solution, various buffer solutions, an organic solvent, and the like may be inserted between these solutions. In this connection, as such a buffer solution, any one not inhibit formation of a complex between an analyte or an analogue thereof and not less than one kind of CFSs, can be used, including buffers usually used in this field, for example, Tris buffer, Good's buffer, TE buffer, TAE buffer, TBE buffer, TBS buffer, a phosphate buffer, a borate buffer, and the like.

In this connection, a solution containing an analyte or an analogue thereof, and solutions including not less than one kind of CFSs, along with if necessary, the liquids, are formed and arranged as each separate zone in a capillary. In other words, between a solution containing an analyte or an analogue thereof, and solutions including not less than one kind of CFSs, along with if necessary, between the solution containing an analyte or analogue thereof and the liquid or between the solution including not less than one kind of CFSs and the liquid, liquid-liquid interface is formed and maintained at the time these solutions, and if necessary, the liquids are arranged.

In a step (1), as a method for introducing a solution containing an analyte or an analogue thereof, and solutions including not less than one kind of CFSs into a capillary, any method is allowed as long as a zone of the solution containing an analyte or an analogue thereof, and a zone of the solutions including not less than one kind of CFSs are separately formed in a capillary, so that arrangement as described above is formed, in other words, any method is allowed as long as liquid-liquid interface is formable between the solution containing an analyte or an analogue thereof, and the solutions including not less than one kind of CFSs, along with if necessary, between the solution containing an analyte or analogue thereof and a liquid or between the solution including not less than one kind of CFSs and the liquid, and a well-known methods for introducing can be used. Such well-known method for introducing includes, for example, a method for electrically introducing these solutions (and the liquids) into a capillary by applying a voltage onto a capillary; a method for introducing these solutions (and the liquids) into a capillary increasing and/or reducing a pressure of the capillary inside; a method for introducing these solutions (and the liquids) into a capillary using capillary phenomenon; and the like.

In addition as a method for introducing and arranging a solution containing an analyte or an analogue thereof, and solutions including not less than one kind of CFSs into a capillary, known methods themselves for introducing and arranging can be used. Such known method for introducing and arranging includes, for example, (1) a method for introducing first one kind of a solution among a solution containing an analyte or an analogue thereof, and solutions including not less than one kind of CFSs into a capillary from the tip of a capillary, by a method for introduction as described above, and subsequently introducing one kind of the remaining solutions into a capillary from the tip of a capillary similarly by a method for introduction as described above, which is repeated till all of the solutions are arranged into a capillary; (2) a method for dropping first one kind of a solution among a solution containing an analyte or an analogue thereof, and solutions including not less than one kind of CFSs into a fluid reservoir (a well), and introducing the content into a capillary by a method for introduction as described above, and then replacing the solution in the fluid reservoir (the well) with one kind of a solution among the remaining solutions, and introducing the content into a capillary by a method for introduction as described above, which is repeated till all of the solutions are arranged into a capillary; (3) a method for dropping a solution containing an analyte or an analogue thereof, and solutions including not less than one kind of CFSs, separately into a plurality of fluid reservoirs (wells), and introducing these separately into the same capillary by a method for introduction as described above, to arrange all of the solutions into a capillary; and the like. In this connection, a method for introducing a solution containing an analyte or an analogue thereof, and solutions including not less than one kind of CFSs into a capillary, and a method for introducing and arranging a solution containing an analyte or an analogue thereof, and solutions including not less than one kind of CFSs into a capillary are not limited to the above-described methods.

In addition, a method for introducing the following: A sample containing an analyte; a solution including a sample having an analyte and a labeled analogue or a reaction improvement analogue (a solution containing an analyte or an analogue); a solution containing an analyte and not less than one kind of CFSs (for example, a CFS, a labeled CFS, a reaction improvement CFS, combinations thereof); a solution including a labeled analogue; or a solution including a reaction improvement analogue; into a capillary is the same as a method for introducing a solution containing an analyte or an analogue thereof, and solutions including not less than one kind of CFSs into a capillary, as described above.

1-2. A Step of Concentrating Reaction [a Step (2)]

A step (2) of the present invention is a step of contacting said analyte or analogue thereof and CFS while concentrating said analyte or analogue thereof and/or CFS electrophoretically to form a complex between said analyte or analogue thereof and CFS, not by (not depending on) molecular diffusion.

"Before solutions (a solution containing an analyte or an analogue thereof and solutions containing not less than one kind of CFSs) are uniformly mixed" means "before each zone (liquid-liquid interface) of a solution containing an analyte or an analogue thereof and a solution including not less than one kind of CFSs, along with if necessary the liquid, arranged into a capillary by a step (1) of the present invention, are uniformly mixed by molecular".

In this connection, in the present invention, "interface" means, boundary where a solution containing an analyte or an analogue thereof, and solutions including not less than one kind of CFSs are contacting, or if necessary boundary where the solution containing an analyte or analogue thereof and the liquid are contacting or boundary where the solution including not less than one kind of CFSs and the liquid are contacting, and said interface does not necessarily mean completely no mixing, due to presence of diffusion from a practical standpoint.

In addition, in a competitive method using an analogue of an analyte, and when a labeled analogue is used, the above-described term means "before uniformly mixing the following zones (liquid-liquid interface) arranged into a capillary by a step (1), by molecular diffusion"; (1) an each zone (liquid-liquid interface) of a solution containing a sample having an analyte and a labeled analogue (a solution containing an analyte and an analogue) along with a solution containing not less than one kind of CFSs (a CFS, a reaction improvement CFS, combinations thereof), and if necessary the liquid; (2) an each zone (liquid-liquid interface) of a sample containing an analyte, a solution containing a labeled analogue and a solution containing not less than one kind of CFSs (a CFS, a reaction improvement CFS, combinations thereof), and if necessary the liquid; or (3) an each zone (liquid-liquid interface) of a solution containing a sample having an analyte and not less than one kind of CFSs (a CFS, a reaction improvement CFS, combinations thereof) and a solution containing a labeled analogue, and if necessary the liquid.

In a competitive method using an analogue of analyte, when a reaction improvement analogue is used, the above-described term means "before uniformly mixing the following zones (liquid-liquid interface) by molecular diffusion"; (1) an each zone (liquid-liquid interface) of a solution containing a sample having an analyte and a reaction improvement analogue (a solution containing an analyte and an analogue) along with a solution containing not less than one kind of labeled CFSs, and if necessary the liquid; (2) an each zone (liquid-liquid interface) of a sample containing an analyte, a solution containing a reaction improvement analogue and a solution containing not less than one kind of labeled CFSs, and if necessary the liquid; or (3) an each zone (liquid-liquid interface) of a solution containing a sample having an analyte and not less than one kind of CFSs (a CFS, a labeled CFS, combinations thereof) and a solution containing a reaction improvement analogue, and if necessary the liquid.

In this connection, "interface" also has the same meaning as above.

In a step (2), "concentrating an analyte or an analogue thereof, and/or at least one kind of a CFS by applying a voltage onto a capillary" means that at least one kind among an analyte or an analogue thereof and not less than one kind of CFSs gather in band-like (plug-like) on application of a voltage onto a capillary. In other words, it means that said substances gather on application of a voltage onto a capillary so that such a portion is generated wherein concentration of said substance becomes higher than that of a substance in a zone arranged in a step (1), namely it means that an analyte or an analogue thereof and/or a CFS gather on application of a voltage onto a capillary, and a portion is generated wherein concentration of an analyte or an analogue thereof and/or concentration of a CFS becomes higher than that of an analyte or an analogue and/or that of a CFS in a solution zone (for example, a zone of a solution containing an analyte or an analogue thereof, a zone of a solution containing a CFS) arranged in a step (1).

In this connection, as for level (degree) of concentration in the present invention, concentration of an analyte or an analogue thereof and/or at least one kind of a CFS at an gathered part (band-like) of said substance on application of a voltage onto a capillary, relative to concentration of an analyte or an analogue thereof and/or at least one kind of a CFS in a zone arranged by a step (1) is, as lower limit, usually not lower than 1.5 times, preferably not lower than 5 times, more preferably not lower than 10 times, and further preferably not lower than 25 times, and upper limit is not especially limited, however usually not higher than $10^7$ times, preferably not higher than $10^6$ times and more preferably not higher than $10^5$ times.

In addition, in the present invention, "contacting said analyte or analogue thereof with CFS" means that, as described above, contact between an analyte or an analogue thereof and a CFS is occurred not by (not depending on) molecular diffusion and by the phenomenon that a substance with (having?) higher electrophoretic mobility (faster electrophoretic speed) among an analyte or an analogue thereof and not less than one kind of CFSs overtakes a substance with (having?) lower electrophoretic mobility (slow electrophoretic speed), by utilization of the fact that when electrophoresis carried out under the condition that a solution containing a substance with (having?) higher electrophoretic mobility (faster electrophoretic speed) is arranged at upstream of a solution containing a substance with (having?) lower electrophoretic mobility (slow electrophoretic speed), a substance with (having?) higher electrophoretic mobility (faster electrophoretic speed) in a solution overtakes a substance with (having?) lower electrophoretic mobility (slow electrophoretic speed).

Namely, in a step (2) of the present invention, an analyte or an analogue thereof in a solution, and a CFS in a solution are made contact by movement (migration) electrophoretically, without mixing by (depending on) molecular diffusion generated by standing still a solution containing an analyte or an analogue thereof and a solution including not less than one kind of CFSs, along with if necessary the liquid, arranged in a capillary, or also not by physical mixing thereof in a capillary.

As described above, a step (2) of the present invention forms a complex between said analyte or analogue thereof and CFS by migrating an analyte or analogue thereof in a solution and a CFS in a solution electrophoretically and contacting them while concentrating an analyte or analogue thereof and/or a CFS electrophoretically, before a solution containing an analyte or an analogue thereof and solutions including a CFSs, along with if necessary the liquid, are uniformly mixed by molecular diffusion, and further without uniformly mixing these physically in a capillary, in other words, with maintaining a liquid-liquid interface between these adjacent solutions and if necessary between the liquid and the solution.

In the present invention, "contacting said analyte or analogue thereof with CFS while concentrating said analyte or analogue thereof and/or at least one kind of CFS by applying a voltage to a capillary" means the following both cases: (1) The case that the above-mentioned concentration of an analyte or an analogue thereof and/or a CFS, and contact of an analyte or an analogue thereof and a CFS are simultaneously carried out; or (2) the case that after substantial completion of the above-mentioned concentration of an analyte or an analogue thereof and/or a CFS, contact of an analyte or an analogue thereof and a CFS is carried out. Therefore, the term includes the cases other than the case that concentration of an analyte or an analogue thereof and/or a CFS is carried out after substantial completion of contact between an analyte or an analogue thereof and a CFS.

In other words, a step (2) of the present invention can be carried out by applying a voltage onto said capillary under condition that a complex between said analyte or analogue thereof and CFS can be formed by contacting said analyte or analogue thereof and CFS while concentrating said analyte or analogue thereof and/or at least one kind of CFS as described above by applying a voltage onto said capillary as described above, before a solution containing an analyte or an analogue thereof and solutions containing not less than one kind of CFSs are uniformly mixed.

Such conditions are specifically those used in so-called an electrophoresis concentration method for concentration of substances in a capillary.

An electrophoresis concentration method includes, for example, methods using difference in electrophoretic mobility in a capillary such as (1) Field Amplification Sample Stacking Method (FASS) [US-A-2003-0057092 A1; Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735; Ross, D., Locascio, L. E. *Anal Chem.* 2002, 71, 5137-5145, and the like]; (2) Field Amplification Sample Injection Method (FASI) [Chien, R. L et al. *J. Chromatogr.* 1991, 559, 141-148, and the like]; (3) Isotachophoresis (ITP) [Everaerts, F. M., Geurts, M. Mikkers, F. E. P., Verheggen, T. P. E. M *J. Chromatogr.* 1976, 119, 129-155; Mikkers, F. F. P., Everaerts, F. M., Peek, J. A. F. *J. Chromatogr.* 1979, 168, 293-315; Mikkers, F. E. P., Everaerts, F. M., Peek, J. A. F. *J. Chromatogr.* 1979, 168, 317-332; Hirokawa, T, Okamoto, H. Ikuta, N., and Gas, B., *Analytical Sciences* 2001, Vol. 17 Supplement i185, and the like]; (4) Isoelectric Focusing method (IF) [Wehr T, et al., *Am. Biotechnol. Lab.* 1990, 8, 22; Kilar F. et al., *Electrophoresis* 1989, 10, 23-29, and the like]; (5) Large-volume sample stacking method (LVSS) [Siri, N. et al., J. Chormatogr. B, (2003), 793, 151-157, and the like]; (6) pH junction method (pH-mediated stacking) [P. Britz-McKibbin et al., 2000, *Anal. Chem.*, 72, 1242, P. Britz-McKibbin et al., 2002, *Anal. Chem.*, 74, 3736]; (7) Sweeping method (stacking micellar electrokinetic chromatography) [J. P. Quirino et al., 1998, *Science*, 282, 465, J. P. Quirino et al., 1999, *Anal. Chem.*, 71, 1638, Y. Sera et al., 2001, *Electrophoresis*, 22, 3509]; and the like, however, not limited thereto.

Among the electrophoresis condensation methods described above, for example, ITP, FASS are preferable, and ITP is particularly preferable.

In this connection, ITP is based on principle that an objective substance can be concentrated when the objective substance is sandwiched between an electrophoresis medium (a leading buffer) including a leading ion having faster electrophoretic speed than that of an objective substance, and an electrophoresis medium (a trailing buffer) including a trailing ion having slow electrophoretic speed than that of an objective substance and subjected to electrophoresis.

Therefore, in carrying out a step (2) of the present invention by ITP, at least a an electrophoresis medium (leading buffer) including an leading ion having faster electrophoretic speed than that of an analyte or an analogue thereof and/or not less than one kind of CFSs, and an electrophoresis medium (a trailing buffer) including a trailing ion having slow electrophoretic speed than that of an analyte or an analogue thereof and/or not less than one kind of CFSs are necessary, and these components-are also included in "condition that an analyte or an analogue thereof and/or at least not less than one kind of CFSs are concentrated" of the present invention.

In this connection, a leading buffer is arranged further downstream side of a solution arranged at the most downstream side of a capillary, among a solution containing an analyte or an analogue thereof, and solutions including not less than one kind of CFSs, and a trailing buffer is arranged further upstream side of a solution arranged at the most upstream side of a capillary, among a solution containing an analyte or an analogue thereof, and solutions including not less than one kind of CFSs.

In the above description, as a leading ion, any ion having faster electrophoretic speed than that of an analyte or an analogue thereof and/or not less than one kind of CFSs may be used, and suitably be selected from those usually used in this field. Such ion includes, for example, $Cl^-$, and the like. In addition, use concentration of a leading ion may also suitably be selected from a range usually used in this field. Use concentration is, for example, usually 1 µM to 10 M, preferably 100 µM to 1 M, and more preferably 1 mM to 500 mM.

Also a leading buffer including such a leading ion is used by suitably selected from one usually used in this field, and for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In the above description, as a trailing ion, any ion having slow electrophoretic speed than that of an analyte or an analogue thereof and/or not less than one kind of CFSs may be used, and suitably be selected from one usually used in this field. Such ion includes, including, for example, Good's buffer such as HEPES, TAPS, MES, MOPS, and the like, an amino acid of such as glycine, threonine and the like. In addition, use concentration of a trailing ion may also suitably be selected from a range usually used in this field. Use concentration is, for example, usually 1 µM to 10 M, preferably 100 µM to 1 M, and more preferably 1 mM to 500 mM.

Also a trailing buffer including such a trailing ion is used by suitably selected from one usually used in this field, and for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In this connection, the above-described conditions (a leading ion, a leading buffer, a trailing ion, a trailing buffer, and the like), other reagents, operation methods, other conditions, and the like can be selected according to the description in the above-described references, and the like.

FASS, FASI and LVSS are based on principle that electrophoretic mobility of an objective substance is decreased and an objective substance is concentrated, when an objective substance reaches interface between a medium wherein an objective substance is present, and a medium having higher electric conductivity than that of a medium wherein an objective substance is present.

Therefore, when a step (2) of the present invention is carried out by FASS, LVSS or FASI, at least one kind of a solution among a solution containing an analyte or an analogue thereof, and solutions including not less than one kind of CFSs is required to have higher electric conductivity than that of other at least one kind of a the solutions; or an electrophoresis medium (high electric conductivity electrophoresis medium) having higher electric conductivity than that of a solution containing an analyte or an analogue thereof, and/or solutions including not less than one kind of CFSs is required to be separately used, and these components are also included in "condition that an analyte or an analogue thereof and/or not less than one kind of CFSs are concentrated" of the present invention.

In this connection, a high electric conductivity electrophoresis medium is arranged at further downstream side of a solution arranged at the most downstream in a capillary, among a solution containing an analyte or an analogue thereof, and solutions including not less than one kind of CFSs.

In addition, a high electric conductivity electrophoresis medium may be any one as long as having higher salt concentration than that of a solution containing an analyte or an analogue thereof, and/or solutions including not less than one kind of CFSs, and is used by suitably be selected from one usually used in this field. Such high electric conductivity electrophoresis medium includes, for example, an electrophoresis medium containing NaCl, KCl, and the like. As an electrophoresis medium, for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 μM to 10 M, preferably 100 μM to 1 M, and more preferably 1 mM to 500 mM, and pH is usually 2 to 12, preferably 4 to 10 and more preferably 6 to 9.

In this connection, the above-described conditions (high electric conductivity electrophoresis medium, and the like), other reagents, operation methods, other conditions, and the like can suitably be selected according to the description in the above-described references, and the like.

IF is based on principle that an objective substance is concentrated by filling a capillary (channel) with a solution of amphoteric substances having various isoelectric points, then forming pH gradient in a capillary (channel) by applying a voltage, and when an objective substance reaches pH region corresponding to an isoelectric point.

Therefore, in the case when a step (2) of the present invention is carried out by IF, at least an electrophoresis medium formable pH gradient in a capillary is required, and this component is also included in "condition to make an analyte or an analogue thereof and/or at least one kind of CFSs concentrated" of the present invention.

In the above description, as an electrophoresis medium formable pH gradient in a capillary, anyone formable pH gradient in a capillary by applying a voltage is used by suitably selecting from one usually used in this field. As such an electrophoresis medium formable pH gradient in a capillary, for example, an electrophoresis medium containing a substance formable pH gradient in a capillary, such as ampholyte is included. As such an electrophoresis medium, for example, Good's buffer, Tris buffer, a borate buffer, a phosphate buffer, a histidine buffer, an imidazole buffer, a glycine buffer, and the like are included. Use concentration and pH thereof also may suitably be selected from those usually used in this field, and use concentration is usually 1 μM to 10 M, preferably 100 μM to 1 M, and more preferably 1 mM to 500 mM.

In this connection, the above-described conditions (an electrophoresis medium containing a substance formable pH gradient in a capillary, and the like), other reagents, operation methods, other conditions, and the like can be selected according to the description in the above-described references, and the like.

A pH junction method is one for carrying out concentration of an objective substance contained in a sample at the boundary surface between a sample and an alkaline electrophoresis medium by forming an acidic or a weak acidic sample region (zone) in the alkaline electrophoresis medium.

Therefore, in the case when a step (2) of the present invention is carried out by a pH junction method, at least an electrophoresis medium having more alkaline range pH than that of a solution containing a sample is required, and this component is also included in "condition to make an analyte or an analogue thereof and/or not less than one kind of CFSs concentrated" of the present invention.

In the above description, as an electrophoresis medium having alkaline range pH, any one formable a boundary surface with different pH, between a solution containing a sample and said electrophoresis medium in a capillary by applying a voltage is used by suitably selected from one usually used in this field. As such an electrophoresis medium, for example, Good's buffer such as HEPES, TAPS, MES, MOPS, and the like, a borate buffer, a phosphate buffer, a histidine buffer, an imidazole buffer, a glycine buffer, and the like are included. Use concentration and pH thereof may suitably be selected from those usually used in this field, and use concentration is usually 1 μM to 10 M, preferably 100 μM to 1 M, and more preferably 1 mM to 500 mM, and pH is usually 7 to 11, preferably 7 to 10 and more preferably 7 to 9.

In this connection, the above-described conditions (an electrophoresis medium having alkaline range pH, and the like), other reagents, operation methods, other conditions, and the like can be selected according to the description in the above-described references, and the like.

A sweeping method is based on the following principle:

Namely, an electrophoresis medium including a charged substance forming a micelle is arranged at the upstream side of a solution zone including an objective substance. By applying a voltage here, the micelle formed overtakes an objective substance and forms a micelle complex with an objective substance. When the micelle complex reaches interface between a medium wherein an objective substance is present, and a medium having higher electric conductivity than that of a medium wherein an objective substance is present, electrophoretic speed of an objective substance is decreased and thus an objective substance is concentrated.

Therefore, when a step (2) of the present invention is carried out by a sweeping method, at least one kind of a solution among a solution containing an analyte or an analogue thereof and solutions including not less than one kind of CFSs is required to have high electric conductivity than that of other at least one kind of a the solutions; or an electrophoresis medium (high electric conductivity electrophoresis medium) having higher electric conductivity than that of a solution containing an analyte or an analogue thereof and/or solutions including not less than one kind of CFSs is required to separately be used; and an electrophoresis medium including a charged substance forming a micelle with higher electrophoretic speed than that of an analyte or an analogue thereof and/or not less than one kind of CFSs, and having lower electric conductivity than that of a solution (or an electrophoresis medium) having higher electric conductivity is required; and these components are also included in "condition to make an analyte or an analogue thereof and/or not less than one kind of CFSs concentrated" of the present invention.

In this connection, a high electric conductivity electrophoresis medium is arranged further downstream side of a solution arranged at the most downstream side of a capillary, among a solution containing an analyte or an analogue thereof, and solutions including not less than one kind of CFSs, and an electrophoresis medium including a charged substance forming a micelle is arranged further upstream side of a solution arranged at the most upstream side of a capillary, among a solution containing an analyte or an analogue thereof, and solutions including not less than one kind of CFSs.

In the above description, as a charged substance forming a micelle, any charged substance may be used as long as having faster electrophoretic speed than that of an analyte or an analogue thereof and/or not less than one kind of CFSs, and suitably be selected from one usually used in this field. Such charged substance includes, for example, a surfactant such as SDS, and the like. In addition, use concentration of said charged substance may also suitably be selected from a range usually used in this field, and the amount over critical micelle concentration is used, and, in more specifically, use concentration of said charged substance is for example, usually 1 μM to 10 M, preferably 100 μM to 1 M, and more preferably 1 mM to 500 mM.

Also an electrophoresis medium is used by suitably selected from one usually used in this field, and, for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 μM to 10 M, preferably 100 μM to 1 M, and more preferably 1 mM to 500 mM, and pH is usually 2 to 12, preferably 4 to 10 and more preferably 6 to 9.

In this connection, the above-described conditions [a charged substance forming a micelle, an electrophoresis medium, and the like], other reagents, operation methods, other conditions, and the like can suitably be selected according to the description in the above-described references, and the like.

Applied voltage in a step (2) may be in a range wherein an analyte or analogue thereof and/or a CFS is sufficiently concentrated, and a complex between an analyte or an analogue thereof and a CFS is sufficiently formed, and may suitably be selected from that usually used in this field. In more specifically, voltage is applied, so that electric field intensity is in the following range: as lower limit, usually not lower than 5 V/cm, preferably not lower than 10 V/cm, more preferably not lower than 50 V/cm, further preferably not lower than 500 V/cm, and particularly preferably not lower than 1000 V/cm, and as upper limit, usually not higher than 10000 V/cm, preferably not higher than 5000 V/cm, more preferably not higher than 2000 V/cm.

In addition, other reaction conditions (for example, pH, temperature, time, and the like) preferably be in a range not to inhibit concentration of an analyte or analogue thereof and/or a CFS, and formation of a complex between an analyte or an analogue thereof and a CFS.

Specifically, although not to simply be described because of dependency on property of an analyte or an analogue thereof and a CFS, lower limit of pH is usually not lower than 2, preferably not lower than 5, and upper limit of pH is usually not higher than 10, and preferably not higher than 9; and lower limit of temperature is usually not lower than 0° C., preferably not lower than 5° C., and more preferably not lower than 10° C., and upper limit of temperature is usually not higher than 50° C., preferably not higher than 40° C., and more preferably not higher than 30° C. Reaction time depends on binding constant of a CFS to be used to an analyte or an analogue thereof, and relatively low binding constant requires relatively long reaction time but relatively high binding constant requires relatively short reaction time. In more specifically, for example, lower limit is usually not shorter than 1 minute, preferably not shorter than 3 minutes and more preferably not shorter than 5 minutes; and upper limit is usually not longer than 24 hours, preferably not longer than 12 hours, more preferably not longer than 1 hour and further preferably not longer than 30 minutes.

1-3. A Capillary (Channel)

A capillary (channel) used in the present invention is any one usually used in this field such as a capillary electrophoresis method, a capillary chip electrophoresis method, and the like, and not especially limited.

Material of a capillary (channel) used in the present invention is any one usually used in this field, and not especially limited as long as it can finally form a complex between an analyte or an analogue thereof and not less than one kind of CFSs by making contact of an analyte or an analogue thereof and not less than one kind of CFSs. Examples of a material of capillary (channel) are, for example, silica-based compounds such as glass, quartz and silicon, synthetic polymers such as cyclic olefin copolymer (COC), cyclic olefin polymer (COP), polymethylmethacrylate, polymethylsiloxane, polyvinyl chloride, polyurethane, polystyrene, polysulfone, polycarbonate, polytetrafluoroethylene, and the like. In addition, inner diameter and length of a capillary (channel) are not especially limited as long as they are sufficient to concentrate an analyte or an analogue thereof and/or a CFS, and form a complex between an analyte or analogue thereof and a CFS. For example, inner diameter is usually 1 to 1000 μm, preferably 1 to 200 μm and more preferably 1 to 100 μm, and length is usually 0.1 mm to 100 cm, preferably 0.1 mm to 20 cm and more preferably 0.1 mm to 10 cm.

A step (2) of the present invention is usually carried out in a state that the above-mentioned capillary is filled with an electrophoresis medium. As an electrophoresis medium, a buffer solution for electrophoresis or said buffer solution for electrophoresis containing fillers, and the like are included. In this connection, an electrophoresis medium may be used alone or in combination with two or more kinds. In addition, as a method for introducing an electrophoresis medium into a capillary includes a method for introducing a solution containing an analyte or an analogue thereof, and solutions including not less than one kind of CFSs into a capillary as described above. And any one of the following timings of introduction of an electrophoresis medium into a capillary may be adopted: (1) before the introduction of a solution containing an analyte or an analogue thereof, and/or solutions including not less than one kind of CFSs into a capillary; (2) simultaneously with the introduction of a solution containing an analyte or an analogue thereof, and/or solutions including not less than one kind of CFSs into a capillary; and (3) after the introduction of a solution containing an analyte or an analogue thereof, and/or solutions including not less than one kind of CFSs into a capillary.

Such a buffer solution for electrophoresis is not especially limited as long as it is usually used in this field. Examples of a buffer solution for electrophoresis are, for example, the buffer solutions etc. usually used in the field of a hybridization method, an immunization, and the like such as Tris buffer, a phosphate buffer, Veronal buffer, a borate buffer, Good's buffer, SSC buffer, TBE buffer, TAE buffer, and the like. Concentration of these buffer solutions is usually 0.1 mM to 10 M, preferably 1 mM to 5 M, and more preferably 5 mM to 1M. In addition, any pH of said buffer solution may be used as long as not to give bad effect on separation of substances, and is usually 2 to 13, preferably 4 to 11 and more preferably 5 to 9. In this connection, these buffer solutions may be used alone or in combination with two or more kinds.

Fillers (polymers) filled in a capillary are not especially limited as long as they are usually used in this field. Examples of fillers are, for example, polyethers such as polyethylene oxide (polyethylene glycol), polypropylene oxide; polyalkylene imines such as polyethylene imine; polyacrylic acid polymers such as polyacrylic acid, polyacrylate esters, and poly(methyl acrylate); polyamide-based polymers such as polyacrylamide, polymethacrylamide; polymethacrylic acid-based polymers such as polymethacrylic acid, polymethacrylate esters and poly(methyl methacrylate); polyvinyl-based polymers such as polyvinyl acetate, polyvinyl pyrrolidone and polyvinyl oxazolidone; water-soluble hydroxyl polymers such as pullulan, elsinan, xanthan, dextran and guar gum; water-soluble cellulosic compounds such as methyl cellulose, hydroxyethyl cellulose and hydroxypropyl cellulose; derivatives thereof, and copolymers having a plurality of kinds of monomer unites composing these polymers, and the like. In this connection, these fillers may be used alone or in combination with two or more kinds.

Molecular weight of the fillers as described above is usually 500 Da to 6000 kDa, preferably 1 to 1000 kDa and more preferably 50 to 500 kDa.

Use concentration of the fillers as described above may suitably be selected from a range usually used in this field, and is usually 0.01 to 40% (w/v), preferably 0.01 to 20% (w/v), and more preferably 0.1 to 10% (w/v).

In this connection, viscosity of a buffer solution for electrophoresis when the above-described fillers are added thereto, is usually 1 to 1000 centipoises, preferably 1 to 200 centipoises, and more preferably 1 to 10 centipoises.

1-4. Analyte, Sample, Analogue and Solution Containing Analyte or Analogue (1) Analyte An analyte in the present invention includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, decomposition product thereof, and serum protein such as ferritin, etc.]; enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), a creatine kinase (CK-1, CK-2 and mCK, etc.), a lactate dehydrogenase (LDH1 to LDH5, etc.), a glutamate oxaloacetate transaminase (ASTm and ASTs, etc.), a glutamate-pyruvate transaminase (ALTm and ALTs, etc.), a choline esterase (ChE1 to ChE5, etc.), a leucine aminopeptidase (C-LAP, AA and CAP, etc.), renin, a protein kinase and a tyrosine kinase, etc.]; microorganism such as bacteria (tuberculosis bacteria, pneumococcal organisms, diphtheria organisms, meningococcus, gonococcus, *staphylococcus*, *streptococcus*, enteric bacteria, coliform bacillus and *Helicobacter pylori*, etc.), viruses (rubella virus, herpes virus, hepatitis virus, ATL virus, AIDS virus, influenza virus, adenovirus, enterovirus, poliovirus, EB virus, HAV, HBV, HCV, HIV and HTLV, etc.), fungus (*candida* and *Cryptococcus*, etc.), spirochete (leptospire, *Treponema pallidum*, etc.), *chlamydia* and *mycoplasma*; protein, a peptide or a carbohydrate antigen derived from said microorganisms; various allergen causative of bronchospasm, allergic rhinitis and atopic dermatitis, etc. (allergen derived from the house dust, mites such as *Dermatophagoides farinae* and *Dermatophagoides pteronyssinus*, etc., pollen from cedar, cypress, *Pasupalum thunbergii*, ragweed, timothy, sweet vernal grass and rye, etc., an animal such as a cat, a dog or a crab, etc., food such as rice and egg white, etc., fungus, insect, wood, drug or chemical substance, etc.); lipids (lipoprotein, etc.); protease (trypsin, plasmin and serine protease, etc.); protein antigen tumor marker (PSA, PGI and PGII, etc.); a carbohydrate antigen [AFP (L1 to L3, etc.), hCG (hCG family, etc.), transferrin, IgG, thyroglobulin, Decay-accelerating factor (DAF), carcinoembryonic antigen (CEA, NCA, NCA-2 and NFA, etc.), CA19-9, PIVKA-II, CA125, prostate-specific antigen, a carbohydrate antigen tumor marker having a particular carbohydrate (sugar) chain produced by cancer cell and an ABO carbohydrate antigen, etc.]; carbohydrate (sugar) chain [hyaluronic acid, β-glucan and carbohydrate (sugar) chain contained in the above-described carbohydrate antigen, etc.]; a carbohydrate (sugar) chain binding protein (hyaluronic acid binding protein and β-glucan binding protein, etc.); lectin (concanavalin A, lentil lectin, kidney bean lectin, thorn apple lectin and wheat germ lectin, etc.); phospholipid (cardiolipin, etc.); lipopolysaccharide (endotoxin, etc.); chemical substances (hormones such as PTH, T3, T4, TSH, insulin, LH, FSH and prolactin, etc., an endocrine-disturbing chemicals such as tributyltin, nonyl phenol, 4-octyl phenol, di-n-butyl phthalate, dicyclohexyl phthalate, benzophenone, octachlorostyrene and di-2-ethylhexyl phthalate, etc.); a receptor (receptor for estrogen and TSH, etc.); a ligand (estrogen and TSH, etc.); and antibodies thereto, and the like.

Among the above-described, the method of the present invention is useful for analysis (quantitative determination) of glycoprotein having different carbohydrate (sugar) chain structure, a nucleotide chain (oligonucleotide chain and polynucleotide chain) and a peptide chain (including polypeptide), is especially useful for glycoprotein having different carbohydrate (sugar) chain structure. In this connection, as the carbohydrate (sugar) chain structure is known to be changed in a particular disease such as cancer, and reported its usefulness in the clinical laboratory (clinical chemistry), the glycoprotein having different carbohydrate (sugar) chain structure can be reassessed for its usefulness in the clinical laboratory (clinical chemistry) using the method of the present invention. In addition, the separation of a mutant type generated by minute mutation or substitution, etc. of a nucleotide chain (an oligonucleotide chain or a polynucleotide chain) or a peptide chain (including polypeptide), etc. from the wild type has been considered as an important analytical target in the field of molecular biology and molecular clinical laboratory (clinical chemistry), and therefore, by analyzing (determining quantity) these mutant type and/or wild type using the method of the present invention, the possibility of finding out some valuable factors and the like in the clinical laboratory (clinical chemistry) will be increased.

(2) Sample Containing Analyte

A sample containing an analyte of the present invention described above may be exemplified by the followings: samples derived from biological origin including body fluid such as serum, plasma, spinal fluid, synovial fluid, lymph fluid, etc., excretions such as urine, faces, etc., expectoration, purulent matter, dermal exfoliation, environmental samples such as food, beverage, tapwater, seawater, waterof lakes andmarshes, river water, factory waste water, washings for semiconductors, washings after washing of medical instruments, etc.; and their processed products reconstituted by dissolving in water or a buffer usually used in this field such as Tris buffer, phosphate buffer, Veronal buffer, borate buffer, Good's buffer, etc. In this connection, a sample relevant to the present invention encompasses one containing an analytes as described above produced by chemical synthesis.

(3) Analogue (a Labeled Analogue and a Reaction Improvement Analogue)

An analogue used in the present invention is a substance to which a CFS, binding to a target analyte for analysis in a sample, is bindable. In other words, an alalogue is a substance a having the same binding site as the binding site present in an analyte in said sample to which a CFS is bindable.

Such a substance includes, for example, the same one as an analyte in a sample, a target of an analysis; one wherein a part of structure of an analyte in a sample is modified, altered, denatured, removed, etc. (so-called an analogue); and the like. Examples of a substance are, for example, recombinant protein introduced with partial mutation at an analyte in a sample, a target of an analysis; peptide with partially modified peptide sequence of an analyte in a sample, a target of an analysis; a nucleotide chain with partially modified nucleotide sequence of an analyte in a sample, a target of an analysis; and the like. In this connection, specific examples of an analyte in a sample, a target of an analysis, are as described above.

In this connection, a labeled analogue and a reaction improvement analogue used in the present invention are ones wherein a labeling substance or a reaction improvement substance is bound to the above described substances, and specific examples and preferable embodiments of a labeling substance and a reaction improvement substance are as described later. In addition, a method for binding a labeling substance or a reaction improvement substance to the above-described substances may be in accordance with a similar method to a method for binding between a reaction improvement substance and a CFS or a method for labeling a CFS by a labeling substance, to be described later.

Use amount of an analogue (a labeled analogue or a reaction improvement analogue) is not simply described because of dependency on kinds of an analogue (a labeled analogue or a reaction improvement analogue) to be used, or kinds or use concentration of a CFS, and the like.

In more specifically, an analogue (a labeled analogue or a reaction improvement analogue) may be contained in a solution (for example, a solution containing an analyte and an analogue, a solution containing an analogue, a solution containing an analogue and a CFS), so that use amount of an analogue (a labeled analogue or a reaction improvement analogue) in a solution as described above is, as lower limit, usually not lower than 10 pM, preferably not lower than 1 nM and more preferably not lower than 100 nM, and as an upper limit, usually not higher than 10 µM, preferably not higher than 1 µM and more preferably not higher than 500 nM.

(4) Solution Containing Analyte or Analogue

"A solution containing an analyte or an analogue" in the present invention means a solution including an analyte (a sample including the analyte) or an analogue (a labeled analogue or a reaction improvement analogue) of the present invention, as described above.

Such a solution includes (a) a sample itself including an analyte, as described above, (b) a solution including a sample having an analyte and not less than one kind of CFSs (in other words, a solution including a complex between an analyte and not less than one kind of CFSs), (c) a solution containing an analogue (a labeled analogue or a reaction improvement analogue), (d) a solution containing a sample having an analyte and an analogue (a labeled analogue or a reaction improvement analogue) (in other words, a solution including an analyte and an analogue), (e) a solution containing an analogue (a labeled analogue or a reaction improvement analogue) and not less than one kind of CFSs (in other words, a solution including a complex between an analogue and not less than one kind of CFSs), (f) a solution including a sample having an analyte, an analogue (a labeled analogue or a reaction improvement analogue) and not less than one kind of CFSs, and the like.

In this connection, as the above solution (b) or (e), for example, when 2 or more kinds of CFSs are used in the present invention, a solution containing a complex (an intermediate complex) between a part of CFSs among all of CFSs finally binding with an analyte or an analogue thereof (a part of the whole CFSs), and an analyte or an analogue thereof, in other words, a solution containing a complex (an intermediate complex) between CFS (s) fewer than CFSs composing a finally formed complex between an analyte or an analogue thereof and 2 or more kinds of CFSs, and an analyte or an analogue thereof is specifically included.

Namely, for example, when 2 kinds of CFSs are used, it is a solution containing a complex (an intermediate complex) between one kind of a CFS and an analyte or an analogue thereof. And for example, when 3 kinds of CFSs are used, it is a solution containing a complex (an intermediate complex) between one kind of a CFS and an analyte or an analogue thereof, and a solution containing a complex (an intermediate complex) between 2 kinds of CFSs and an analyte or an analogue thereof. (In this case, also when 4 or more kinds of CFSs are used, a way of thinking is the same as in theses cases.)

In more specifically, for example, as will be described later, when a CFS not bound with a labeling substance and a reaction improvement substance, and a reaction improvement CFS are used in combination as a CFS, a solution containing a complex (an intermediate complex) between an analyte and said CFS, and a solution containing a complex (an intermediate complex) between an analyte and a reaction improvement CFS correspond to a solution (b) as described above; and when a labeled CFS and a reaction improvement CFS are used in combination as a CFS, a solution containing a complex (an intermediate complex) between an analyte and a labeled CFS, and a solution containing a complex (an intermediate complex) between an analyte and a reaction improvement CFS correspond to a solution (b) as described above. In addition, when a CFS not bound with a labeling substance and a reaction improvement substance, and a labeled reaction improvement CFS are used in combination as a CFS, a solution containing a complex (an intermediate complex) between an analyte and said CFS, and a solution containing a complex (an intermediate complex) between an analyte and a labeled reaction improvement CFS correspond to a solution (b) as described above.

In this connection, in the above description, usually, a solution containing a sample having an analyte, and not less than one kind of CFSs is generally a reaction solution obtained by suitably mixing a sample including an analyte as described above (a CFS is not included) and a solution including a CFS as will be described later.

The above solution (e) includes, in more specifically, for example, when a labeled analogue or a reaction improvement analogue is used, and when 2 or more kinds of CFSs are used, a solution containing, similarly as described above, a complex (an intermediate complex) between a part of CFSs among all of CFSs finally binding with a labeled analogue or a reaction improvement analogue (a part of the whole CFSs), and a labeled analogue or a reaction improvement analogue, in other words, a solution containing a complex (an intermediate complex) between CFS (s) fewer than CFSs composing a finally formed complex between a labeled analogue or a reaction improvement analogue and 2 or more kinds of CFSs, and a labeled analogue or a reaction improvement analogue. In this connection, in the above description, usually, a solution containing an analogue (a labeled analogue or a reaction improvement analogue) is generally a reaction solution obtained by suitably mixing a solution including a labeled analogue or a reaction improvement analogue, and a solution including a CFS as will be described later.

In addition, as the above solution (d), for example, a solution containing an analyte in a sample, and an analogue labeled with a labeling substance (a labeled analogue) or an analogue bound with a reaction improvement substance (a reaction improvement analogue) is included. In this connection, a solution containing a sample having an analyte and an analogue is usually and generally a mixed solution obtained by suitably mixing a sample including an analyte (a CFS is not contained) and a solution including an analogue.

As the above solution (f), in more specifically, for example, when a labeled analogue or a reaction improvement analogue is used, and when 2 or more kinds of CFSs are used, a solution containing, similarly as described above, a complex (an intermediate complex) between a part of CFSs among all of CFSs finally binding with an analyte and/or a labeled analogue (or a reaction improvement analogue), and an analyte and/or a labeled analogue (or a reaction improvement analogue) (a part of the whole CFSs), in other words, a solution containing a complex (an intermediate complex) between CFS(s) fewer than CFSs composing a finally formed complex between an analyte and/or a labeled analogue (or a reaction improvement analogue) and 2 or more kinds of CFSs, and an analyte and/or a labeled analogue (or a reaction improvement analogue). In this connection, a solution including a sample having an analyte, an analogue (a labeled analogue or a reaction improvement analogue) and not less than one kind of CFSs is usually and generally a reaction solution obtained by suitably mixing a solution including a sample having an analyte as described above, a solution containing a labeled analogue or a reaction improvement analogue, and solutions including not less than one kind of CFSs.

In the above description, (a) a sample including an analyte is as described above. In addition, as solutions (b) to (f), any one is used as long as not to inhibit formation of a complex between an analyte and a CFS, and/or a complex between an analogue (a labeled analogue or a reaction improvement analogue) and a CFS, and for example, water, a buffer solution, and the like are included.

As such a buffer solution, one having buffer action at a pH range of usually 5 to 11, and usually used in this field is included. Examples of the buffer solution include Tris buffer, Good's buffer, TE buffer, TAE buffer, TBE buffer, TBS buffer, a phosphate buffer, a borate buffer, and the like, and use concentration thereof is usually in a range of 1 mM to 2 M, and preferably 10 mM to 1 M, and pH is usually 5 to 11, preferably 5 to 10, more preferably 5.5 to 8.5, further preferably 6 to 8 and particularly preferably around 7.

1-5. CFS and a Solution Containing Thereof

In the present invention, "a substance formable a complex with an analyte or an analogue thereof (CFS)" means a substance having a property capable of forming a complex between a analyte or an analogue thereof and the CFS, namely, a complex containing the analyte or the analogue thereof and the CFS as constituent by binding with an analyte or the analogue thereof as the above described, or by binding with the analyte or the analogue thereof through other CFS.

Such CFS means the substance which binds with an analyte or an analogue thereof by interaction such as an "antigen"-"antibody" reaction, a "carbohydrate (sugar) chain"-"protein" reaction, "carbohydrate (sugar) chain"-"lectin" reaction, "enzyme"-"inhibitor" reaction, "protein"-"peptide chain" reaction or "chromosome or nucleotide chain"-"nucleotide chain" reaction, and the like. When one of the substances in the above-mentioned pairs is the analyte or the analogue thereof, the other is the CFS. For example, when an analyte or an analogue thereof is an "antigen", a CFS is an "antibody", and when an analyte or an analogue thereof is an "antibody", a CFS is an "antigen" (the same applied to the above other pairs).

In more specifically, such a substance includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, decomposition product thereof, and serum protein such as ferritin, etc.]; enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), a creatine kinase (CK-1, CK-2 and mCK, etc.), alactate dehydrogenase (LDH1 to LDH5, etc.), a glutamate oxaloacetate transaminase (ASTm and ASTs, etc.), a glutamate-pyruvate transaminase (ALTm and ALTs, etc.), a choline esterase (ChE1 to ChE5, etc.), a leucine aminopeptidase (C-LAP, AA and CAP, etc.), renin, a protein kinase and a tyrosine kinase, etc.]; microorganism such as bacteria (tuberculosis bacteria, pneumococcal organisms, diphtheria organisms, meningococcus, gonococcus, *staphylococcus, streptococcus*, enteric bacteria, coliform bacillus and *Helicobacter pylori*, etc.), viruses (rubella virus, herpes virus, hepatitis virus, ATL virus, AIDS virus, influenza virus, adenovirus, enterovirus, poliovirus, EB virus, HAV, HBV, HCV, HIV and HTLV, etc.), fungus (*candida* and *Cryptococcus*, etc.), spirochete (leptospire, *Treponema pallidum*, etc.), *chlamydia* and *mycoplasma*; protein, a peptide or a carbohydrate antigen derived from said microorganisms; various allergen causative of bronchospasm, allergic rhinitis and atopic dermatitis, etc. (allergen derived from the house dust, mites such as *Dermatophagoides farinae* and *Der-*

*matophagoides pteronyssinus*, etc., pollen from cedar, cypress, *Pasupalum thunbergii*, ragweed, timothy, sweet vernal grass and rye, etc., an animal such as a cat, a dog or a crab, etc., food such as rice and egg white, etc., fungus, insect, wood, drug or chemical substance, etc.); lipids (lipoprotein, etc.); protease (trypsin, plasmin and serine protease, etc.); antigen of tumor marker protein (protein antigen of tumor marker?) (PSA, PGI and PGII, etc.); a carbohydrate antigen [AFP (L1 to L3, etc.), hCG (hCG family, etc.), transferrin, IgG, thyroglobulin, Decay-accelerating factor (DAF), carcinoembryonic antigen (CEA, NCA, NCA-2 and NFA, etc.), CA19-9, PIVKA-II, CA125, prostate-specific antigen, a carbohydrate antigen tumor marker having a particular carbohydrate (sugar) chain produced by cancer cell and an ABO carbohydrate antigen, etc.]; carbohydrate (sugar) chain [hyaluronic acid, β-glucan and carbohydrate (sugar) chain contained in the above-described carbohydrate antigen, etc.]; a carbohydrate (sugar) chain binding protein (hyaluronic acid binding protein and β-glucan binding protein, etc.); lectin (concanavalin A, lentil lectin, kidney bean lectin, thorn apple lectin and wheat germ lectin, etc.); phospholipid (cardiolipin, etc.); lipopolysaccharide (endotoxin, etc.); chemical substances (hormones such as PTH, T3, T4, TSH, insulin, LH, FSH and prolactin, etc., an endocrine-disturbing chemicals such as tributyltin, nonyl phenol, 4-octyl phenol, di-n-butyl phthalate, dicyclohexyl phthalate, benzophenone, octachlorostyrene and di-2-ethylhexyl phthalate, etc.); a receptor (receptor for estrogen and TSH, etc.); a ligand (estrogen and TSH, etc.); and antibodies thereto, and the like. In this connection, the antibody used in the present invention encompasses a decomposition product such as Fab and F(ab')$_2$ fragments and the like produced by degradation with a proteolytic enzyme (proteinase, etc.) such as papain or pepsin or by chemical degradation.

The CFS described above may be used alone or in combination with two or more kinds.

In this connection, when two or more kinds of the CFSs are used in combination (together), the binding site of each CFS is not especially limited as long as two or more kinds of the CFSs can form a complex with an analyte or an analogue thereof. The binding sites to be bound by such CFSs include, for example, a case when all of binding sites to be bound by two or more of the CFSs are present on the analyte or the analogue thereof [binding form (1)]; a case when the binding site to be bound by at least one kind of the CFS (for example, CFS A) among two or more of the CFSs is present only on the analyte or the analogue thereof, and the binding site to be bound by another at least one kind of the CFS (for example, complex binding substance B) is present on a site newly generated by the formation of a complex between an analyte or an analogue thereof and the CFS A [binding form (2)]; and a case when the binding site to be bound by at least one kind of the CFS (for example, CFS A) among two or more of the CFSs is present only on the analyte or the analogue thereof, and the binding site to be bound by another at least one kind of the CFS (for example, CFS B) is present only on the CFS A [binding form (3)]. Among these, it is preferable that the binding sites to be bound by each two or more of the CFSs are different. In this connection, in binding form (2), the substance having property to specifically binding to a newly generated site (a CFS) includes, for example, an antibody, a peptide chain and a nucleotide chain, and the like, which can recognize a complex between an analyte or an analogue thereof and a CFS, and capable of binding thereto are included.

As a CFS as described above, one which binds with an analyte or an analogue thereof by an "antigen"-"antibody" reaction or a "carbohydrate (sugar) chain"-"protein" reaction is preferable. Specifically, an antibody to an analyte or an analogue thereof, or an antigen bound with an analyte or an analogue thereof, or protein binding to an analyte or an analogue thereof is preferable, an antibody to an analyte or an analogue thereof, or protein binding to an analyte or an analogue thereof is more preferable.

A CFS as described above may be bound with a labeling substance and/or a substance capable of changing electrophoretic mobility (hereinafter, abbreviated as a reaction improvement substance) of an analyte or an analogue thereof and may result in (1) a CFS having property capable of forming a complex with an analyte or an analogue thereof and capable of changing electrophoretic mobility of an analyte or an analogue thereof (hereinafter, abbreviated as a reaction improvement CFS or a reaction improvement CFS), (2) a CFS having property capable of forming a complex with an analyte or an analogue thereof and labeled with a labeling substance (a labeled CFS), and (3) a CFS labeled with a labeling substance, having property capable of forming a complex with an analyte or an analogue thereof and capable of changing electrophoretic mobility of an analyte or an analogue thereof (a labeled reaction improvement CFS).

By using a CFS bound with a reaction improvement substance, electrophoretic mobility of a CFS can be changed, and arrangement order of a solution containing an analyte or an analogue thereof, and solutions including not less than one kind of CFSs in a step (1), can arbitrarily be controlled, and efficiency in concentration of an analyte or an analogue thereof and/or a CFS, and a reaction of an analyte or an analogue thereof and a CFS (a complex formation reaction) can be enhanced.

In addition, by using a CFS bound with a labeling substance, an analyte in a sample can be measured (detected).

(1) A Reaction Improvement CFS

A reaction improvement CFS is one having property capable of forming a complex between an analyte or an analogue thereof and the substance, and capable of changing electrophoretic mobility of an analyte or an analogue thereof, in other words, one having property capable of generating difference in behavior (electrophoretic mobility) of said analyte or analogue thereof corresponding to electrophoresis operation by forming a complex with an analyte or an analogue thereof, and one capable of making electrophoretic mobility of a complex between an analyte or an analogue thereof and a reaction improvement CFS (or a complex between an analyte or an analogue thereof and a CFS other than a reaction improvement CFS) higher or lower than electrophoretic mobility (faster or slower than electrophoretic mobility) of an analyte or an analogue thereof itself (an analyte or an analogue thereof not bound with a reaction improvement CFS).

As such a reaction improvement CFS, the above-described CFSs bound with the following reaction improvement substances are general: For example, an inorganic metal oxide such as silica and alumina, etc.; a metal such as gold, titanium, iron and nickel, etc.; an inorganic metal oxide introduced with a functional group by an operation such as silane coupling treatment, etc.; organisms such as various microorganisms and eukaryote cells, etc.; polysaccharide such as agarose, cellulose and insoluble dextran, etc.; synthetic polymer compounds such as polystyrene latex, a styrene-butadiene copolymer, a styrene-methacrylic acid copolymer, an acrolein-ethyleneglycol dimethacrylate copolymer, styrene-styrenesulfonic acid latex, polyacrylamide, polyglycidyl methacrylate, polyacrolein coated particles, crosslinked polyacrylonitrile, acrylic acid or acrylate ester-based polymers, an acrylonitrile-butadiene copolymer, a vinyl chloride-acrylate ester copolymer and a poly vinyl acetate-acrylate copolymer, etc.; biomolecules such as erythrocyte, sugar, nucleic acid (polynucleotide such as RNA, DNA), protein, polypeptide and polyamino acid (polyglutamic acid, polyaspartic acid, polylysine, etc.); lipids; and the like.

However, for example, a reaction improvement substance may be bound to an analyte or an analogue thereof by a chemical binding method such as a method for introducing a functional group at the surface of a reaction improvement substance and subsequently binding to an analyte or an analogue thereof via this functional group; by a method for binding between a reaction improvement substance and an analyte or an analogue thereof via a linker; and the like. In this connection, in the above description, a reaction improvement substance is one having property capable of providing property as a reaction improvement CFS as described above to said CFS, by binding to a CFS. Namely, a reaction improvement substance is one having property capable of changing electrophoretic mobility of an analyte or an analogue thereof, in other words, one having property capable of generating difference in behavior (electrophoretic mobility) of said analyte or analogue thereof corresponding to electrophoresis operation, via a CFS, by forming a complex between an analyte or an analogue thereof and a CFS (or a complex among an analyte or an analogue thereof, a reaction improvement CFS and a CFS other than a reaction improvement CFS), and thus is capable of making electrophoretic mobility of a complex between an analyte or an analogue thereof and a reaction improvement CFS higher or lower than electrophoretic mobility (faster or slower than electrophoretic mobility) of an analyte or an analogue thereof itself or a complex between an analyte or analogue thereof not bound with a reaction improvement CFS and a CFS.

Among those, as a reaction improvement CFS, those obtained by binding nucleic acid (a nucleotide chain), protein, polypeptide or polyamino acid to a CFS as described above are preferable, and those obtained by binding nucleic acid (a nucleotide chain) or polyamino acid to a CFS are more preferable. In addition, as a reaction improvement substance, those including an antibody as a CFS are preferable, specifically, those obtained by binding nucleic acid (a nucleotide chain), protein, polypeptide or polyamino acid as a reaction improvement substance to an antibody as a CFS are preferable, and among others those obtained by binding nucleic acid (a nucleotide chain) or polyamino acid, as a reaction improvement substance, to an antibody as a CFS are particularly preferable.

To make binding of a reaction improvement substance to a CFS, namely, to prepare a reaction improvement CFS, any common method used in this field may be applied, for example, a known labeling method itself generally used in known EIA, RIA, FIA methods or a hybridization method themselves (for example, Ikagaku Jikken Koza (Experimental Manual in Medical Chemistry), vol. 8, edited by Yuichi Yamamura, $1^{st}$ Ed., Nakayama Shoten Co., Ltd., 1971; Zusetu (Illustrative Description) Fluorescent Antibodies, Akira Kawao, $1^{st}$ Ed., Softscience Co., Ltd., 1983; Enzyme Immunoassay, Eiji Ishikawa, Tadashi Kawai, Kiyoshi Miyai, $3^{rd}$ Ed., Igaku-Shoin Ltd., 1987; Molecular Cloning, A Laboratory Manual, 2nd Ed., J. Sambroock, E. F. Fritsch, T. Maniatis, Cold Spring Harbor Laboratory Press; Handbook of Fluorescent Probe and Research Chemicals, $7^{th}$ Ed., Chapter 8, Molecular Probe Inc.; WO 2002/082083); or a common method utilizing a reaction between avidin (or streptoavidin) and biotin.

In this connection, when a reaction improvement CFS is used as a CFS, combined use (parallel use) of a labeled CFS as described above is preferable. However, when a reaction improvement CFS itself is measurable (detectable) by any of a method, or enables to be labeled by a labeling substance, combined use of a labeled CFS is not necessary.

In addition, when a labeled CFS and a reaction improvement CFS are used in combination (are used parallely) as a CFS, and as long as a complex among 3 components of an analyte or an analogue thereof, a labeled CFS and a reaction improvement CFS, is formed, binding forms of these 3 components or binding sites of a labeled CFS and a reaction improvement CFS are not especially limited. Such binding forms include, for example, (1) so-called a sandwich complex wherein an analyte or an analogue thereof is sandwiched by a labeled CFS and a reaction improvement CFS, (2) a complex wherein a reaction improvement CFS or a labeled CFS is further bound at a binding site with an analyte or an analogue thereof and a labeled CFS or a reaction improvement CFS and (3) a complex wherein a reaction improvement CFS or a labeled CFS is further bound at a labeled CFS or a reaction improvement CFS bound with an analyte or an analogue thereof, and the like. In addition, said binding moieties include, for example, (1) the case when all of the binding sites of a labeled CFS and a reaction improvement CFS are present only on an analyte or an analogue thereof [binding form (1)], (2) the case when either of the binding sites of a labeled CFS or a reaction improvement CFS is present only on an analyte and an analogue thereof, and the other binding site is present at a new site generated by formation of a complex between an analyte and either of said labeled CFS and reaction improvement CFS [binding form (2)], (3) either of binding sites of a labeled CFS and a reaction improvement CFS is present only on an analyte or an analogue thereof, while the other binding site is present at only either of said labeled CFS and reaction improvement CFS [binding form (3)] and (4) the case of combinations thereof. Among those, a binding site of a labeled CFS, and a binding site of a reaction improvement CFS is preferably a different one. In this connection, in the above description (2), as one having property to specifically bind at a newly generated site (a labeled CFS and/or a reaction improvement CFS), for example, an antibody, a peptide chain, a nucleotide chain, and the like, which enable to recognize a complex between an analyte or an analogue thereof and a labeled CFS and/or a reaction improvement CFS, and bindable thereto are included.

(2) A Labeled CFS

A CFS as described above is generally one measurable (detectable) itself by any of a method, or enables to be labeled by a labeling substance. By using one having such property, an analyte in a sample can be measured (detected). In this connection, when an analyte or an analogue thereof itself is detectable by any of a method (for example, an enzyme, and the like), or an analyte or an analogue thereof is directly bindable to a labeling substance without using (not through) a CFS, an analyte in a sample can be measured (detected) even when said CFS may not have the above-described property. Examples of those detectable themselves by any of a method include an enzyme, a dye, a fluorescent substance, a luminescent substance, a substance having absorption at UV region, and the like.

Among those, as a CFS used in the present invention, a substance formable a complex with an analyte or an analogue thereof, and labeled by a labeling substance (a labeled CFS) is preferable.

As a labeling substance used in the present invention, any one used in this field such as an enzyme immunoassay (EIA), a radio immunoassay (RIA), a fluorescent immunoassay (FIA), a hybridization method, and the like, may be adopted. Such a labeling substance includes, for example, enzymes such as alkaline phosphatase (ALP), β-galactosidase (β-Gal), peroxidase (POD), microperoxidase, glucose oxidase (GOD), glucose-6-phophate dehydrogenase (G6PDH), malate dehydrogenase and luciferase, etc.; dyes such as Coomassie brilliant blue R250, and methyl orange, etc.; radioactive isotopes such as $^{99m}Tc$, $^{131}I$, $^{125}I$, $^{14}C$, $^{3}H$, $^{32}P$ and $^{35}S$, etc.; HiLyte type dyes such as HiLyte Fluor 488, HiLyte Fluor 555, HiLyte Fluor 647, HiLyte Fluor 680 and HiLyte Fluor 750, etc. (all of them are trade names of HiLyte Bioscience, Inc.); Alexa type dyes such as Alexa Fluor Dye 350, Alexa Fluor Dye 430, Alexa Fluor Dye 488, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700 and Alexa Fluor Dye 750 etc. (all of them are trade names of Molecular Probes, Inc.); CyDye type dyes such as Cy3, Cy3.5, Cy5, Cy5.5 and Cy7, etc. (all of them are trade names of Amersham Biosciences, Inc.); fluorescent materials such as fluorescein, rhodamine, dansyl, fluorescamine, coumarin, naphthylamine, or derivatives thereof, rare-earth fluorescent dyes [combinations of a rare earth metal such as samarium (Sm), europium (Eu), terbium (Tb) or dysprosium (Dy) and a chelate compound such as 4,4'-bis(1",1",1",2",2",3",3"-heptafluoro-4",6"-h exanedione-6"-yl)chlorosulfo-O-terphenyl (BHHCT), 4,7-bis(chlorosulfonyl)-1,10-phenanthoroline-2,9-dicarboxylic acid (BCPDA), β-naphthyltrifluoroacetic acid (β-NTA), etc.], intercalator dyes [for example, acridine dyes such as acridine orange, etc.; ethidium compounds such as ethidium bromide, ethidium homodimer-1 (EthD-1), ethidium homodimer-2 (EthD-2), ethidium bromide monoazide (EMA) and dihydroethidium, etc.; iodine compounds such as propidium iodide, and hexidium iodide, etc.; 7-aminoactinomycin D (7-AAD); cyanine dimmer type dyes such as POPO-1, BOBO-1, YOYO-1, TOTO-1, JOJO-1, POPO-3, LOLO-1, BOBO-3, YOYO-3, and TOTO-3, etc. (all of them are trade names of Molecular Probes, Inc.); SYTOX type dyes such as SYBR Gold, SYBR Green I and SYBR Green II, SYTOX Green, SYTOX Blue, and SYTOX Orange, etc. (all of them are trade names of Molecular Probes, Inc.), and the like], one bound to a minor group of DNA double helix [for example, 4',6-diamidino-2-phenylindole (DAPI: trade name of Molecular Probes, Inc.), pentahydrate(bis-benzimido) (Hoechst 33258: trade name of Molecular Probes, Inc.), and trihydrochloride (Hoechst 33342: trade name of Molecular Probes, Inc.), etc.]; benzimido type dyes (Hoechst 34580: trade name of Molecular Probes, Inc.) and the like], one specifically bound to the sequence of adenine-thymine (A-T) [for example, acridine dyes such as 9-amino-6-chloro-2-methoxyacridine (ACMA), and bis(6-chloro-2-methoxy-9-acridinyl) spermine (acridine homodimer), etc., hydroxystilbamidine, and the like]; luminescent materials such as luciferin, isoluminal, luminal, and bis(2,4,6-trifluorophenyl) oxalate, etc.; material having absortion in ultra-violet region such as phenol, naphthol, anthracene, or derivatives thereof; substances having property as spin labeling agents represented by compounds having an oxyl group such as 4-amino-2,2,6,6-tetramethylpiperidine-1-oxyl, 3-amino-2,2,5,5-tetramethylpyrrolidine-1-oxyl, and 2,6-di-t-butyl-α-(3,5-di-t-butyl-4-oxo-2,5-cyclohexadine-1-ylidene)-p-tolyloxyl; and the like.

Labeling a CFS with a labeling substance may be carried out according to a method similar to a method for labeling a CFS with a labeling substance as described above, or a common method described in WO 2002/082083.

(3) A Labeled Reaction Improvement CFS

Furthermore, in the present invention, as a CFS, such a substance may also be used that is labeled by a labeling substance, formable a complex with an analyte or an analogue thereof, and capable of changing electrophoretic mobility of an analyte (a labeled reaction improvement CFS), namely, a reaction improvement CFS labeled by a labeling substance. In this connection, a labeling substance and a reaction improvement CFS are as described above, and also labeling a reaction improvement CFS with a labeling substance may be carried out according to a method similar to a method for labeling a CFS with a labeling substance as described above, or a common method described in WO 2002/082083.

(4) Combinations of CFSs

As described above, in the present invention, for example, the following various CFSs are used. In this connection, they may naturally be used in suitable combinations.

(a) A CFS not bound with a labeling substance and a reaction improvement substance (b) A labeled CFS (c) A reaction improvement CFS (d) A labeled reaction improvement CFS (e) A CFS not bound with a labeling substance and a reaction improvement substance and a reaction improvement CFS (f) A labeled CFS and a reaction improvement CFS (g) A CFS not bound with a labeling substance, and a reaction improvement substance, and a labeled reaction improvement CFS (5) A Solution Containing a CFS As a solution containing a CFS of the present invention, as described above, any one may be used as long as it does not inhibit formation of a complex between an analyte or an analogue thereof and said CFS. Such solution includes, for example, water, a buffer solution, and the like.

As such a buffer solution, any one may be used as long as it has buffer action usually in a pH range of 5 to 11, and does not inhibit formation of said complex formation reaction. Examples of the buffer solution are those usually used in this field such as Tris buffer, Good's buffer, TE buffer, TAE buffer, TBE buffer, TBS buffer, a phosphate buffer, a borate buffer, and the like. Use concentration of these buffers is usually 1 mM to 2 M, preferably 10 mM to 1 M, and pH is usually 5 to 11, preferably 5 to 10, more preferably 5.5 to 8.5, further preferably 6 to 8 and particularly preferably around 7.

Concentration of a CFS contained in a solution as described above, namely use amount of a CFS is not simply described due to dependency on kinds of CFSs used, however, it is usually preferable that the CFS is present in the reaction solution (a solution containing an analyte or an analogue thereof and a CFS) at a concentration which is not lower than (preferably not lower than 2 times, more preferably not lower than 5 times) a concentration at which the CFS can bind to the whole of the analytes or analogues thereof of a concentration corresponding to the limit of measurement.

In addition, upper limit of the concentration is not especially limited, however, in view of economical efficiency, it is usually not higher than $10^{12}$ times (preferably not higher than $10^9$ times, more preferably not higher than $10^6$ times) a concentration at which the CFS can bind to the whole of the analytes or analogues thereof of a concentration corresponding to the limit of measurement.

In more specifically, a CFS may be contained in a solution as described above, so that concentration of a CFS in a solution containing an analyte or an analogue thereof and a CFS is, as lower limit, usually not lower than 10 pM, preferably not lower than 1 nM, and more preferably not lower than 100 nM, and as upper limit, usually not higher than 10 μM, preferably not higher than 1 μM and more preferably not higher than 500 nM.

1-6. Specific Methods for Forming a Complex

Modes for carrying out the methods for forming a complex of the present invention are specifically shown below.

(a) A Case when a CFS not Bound with a Labeling Substance and a Reaction Improvement Substance are Used.

(1) (a) A solution containing an analyte [for example, (i) a sample including an analyte, (ii) a solution including a sample having an analyte, and not less than one kind of CFSs] and (b) a solution containing not less than one kind of CFSs are introduced and arranged into a capillary so that a zone of the solution containing an analyte [for example, (i) a sample including an analyte, (ii) a solution including a sample having an analyte, and not less than one kind of CFSs], and a zone of the solution including not less than one kind of CFSs are separately formed (so that liquid-liquid interface is formed), and a complex between said analyte and CFS is formed on application of a voltage onto said capillary, without mixing these solutions in advance outside a capillary.

(2) Subsequently, said analyte is electrophoretically contacted with said CFS while concentrating said analyte and/or at least one kind of the CFSs by applying a voltage to said capillary before uniformly mixing these solutions, not by (not depending on) molecular diffusion and without physically mixing, to form the complex between said analyte and the CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], and a solution containing not less than one kind of CFSs, along with if necessary the liquid, arranged in a capillary by a step (1) are uniformly mixed by molecular diffusion". In this connection, "interface" means the same as described above.

In addition, in the above-described step (2), "concentrating said analyte and/or at least one kind of CFSs by applying a voltage onto a capillary" means that, as similarly described above, said analyte and/or at least one kind of CFS gather in band-like (plug-like) on application of a voltage onto a capillary. In other words, it means that said substances gather on application of a voltage onto a capillary so that such a portion is generated wherein concentration of said substances becomes higher than that of a substance in a zone arranged in a step (1), namely it means that an analyte and/or at least one kind of a CFS garher on application of a voltage onto a capillary, and a portion is generated wherein concentration of an analyte and/or concentration of not less than one kind of CFSs becomes higher than that of an analyte and/or not less than one kind of CFSs in a solution zone [for example, a zone of a solution containing an analyte (for example, (i) a sample including an analyte, (ii) a solution including a sample having an analyte, and not less than one kind of CFSs) and a zone of a solution containing not less than one kind of CFSs] arranged in a step (1).

In the above step (2), "said analyte is electrophoretically contacted with said CFS" means that, similarly as described above, contact of said analyte and CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(b) A Case when a Labeled CFS is Used.

(1) (a) A solution containing an analyte [for example, (i) a sample including an analyte, (ii) a solution including a sample having an analyte, and not less than one kind of CFSs] and (b) a solution containing not less than one kind of labeled CFSs are introduced and arranged into a capillary so that a zone of the solution containing an analyte [for example, (i) a sample including an analyte, (ii) solutions including a sample having an analyte, and not less than one kind of CFSs], and a zone of the solution containing not less than one kind of labeled CFSs are separately formed (so that liquid-liquid interface is formed), and a complex between said analyte and labeled CFS is formed on application of a voltage onto a capillary, without mixing these solutions in advance outside a capillary.

(2) Subsequently, said analyte is electrophoretically contacted with said labeled CFS while concentrating said analyte and/or at least one kind of said labeled CFS by applying a voltage onto said capillary before uniformly mixing these solutions, not by (not depending on) molecular diffusion and without physically mixing, to form the complex between said analyte and labeled CFS.

In the above description, "before these solutions are uniformly mixed" means "before each zone (liquid-liquid interface) of a solution containing an analyte [for example, (i) a sample including an analyte, (ii) solutions including a sample having an analyte, and not less than one kind of CFSs], and a solution containing not less than one kind of labeled CFSs, along with if necessary the liquid, arranged in a capillary by a step (1) are uniformly mixed by molecular diffusion". In this connection, "interface" means the same as described above.

In addition, in the above-described step (2), "concentrating said analyte and/or at least one kind of labeled CFSs by applying a voltage onto a capillary" means that, as similarly described above, said analyte and/or at least one kind of labeled CFS to gather in band-like (plug-like) on application of a voltage onto a capillary. In other words, it means that said substances gather on application of a voltage onto a capillary so that such a portion is generated wherein concentration of said substances becomes higher than that of a substance in a zone arranged in a step (1), namely, it means that an analyte and/or at least one kind of a labeled CFS garher on application of a voltage onto a capillary, and a portion is generated wherein concentration of an analyte and/or concentration of at least one kind of a labeled CFS becomes higher than that of an analyte and/or at least one kind of a labeled CFS in a solution zone [for example, a zone of a solution containing an analyte (for example, (i) a sample including an analyte, (ii) a solution including a sample having an analyte, and not less than one kind of CFSs) and a zone of a solution containing not less than one kind of labeled CFSs] arranged in a step (1).

In the above step (2), "said analyte is electrophoretically contacted with said labeled CFS" means that, similarly as described above, contact of said analyte and labeled CFS is conducted, not by (not depending on) molecular diffusion and by utilization of the phenomenon that a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(c) A Case when a Reaction Improvement CFS is Used.

(1) (a) A solution containing an analyte [for example, (i) a sample including an analyte, (ii) a solution including a sample having an analyte, and not less than one kind of CFSs] and (b) a solution containing not less than one kind of reaction improvement CFSs are introduced and arranged into a capillary so that a zone of the solution containing an analyte [for example, (i) a sample including an analyte, (ii) a solution including a sample having an analyte, and not less than one kind of CFSs], and a zone of the solution including not less than one kind of reaction improvement CFSs are separately formed (so that liquid-liquid interface is formed), and a complex between said analyte and reaction improvement CFS is formed on application of a voltage onto a capillary, without mixing these solutions in advance outside a capillary.

(2) Subsequently, said analyte is electrophoretically contacted with said reaction improvement CFS while concentrating said analyte and/or at least one kind of the reaction improvement CFS by applying a voltage onto said capillary before uniformly mixing these solutions, not by (not depending on) molecular diffusion and without physically mixing, to form the complex between said analyte and reaction improvement CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], and a solution containing not less than one kind of reaction improvement CFSs, along with if necessary the liquid, arranged in a capillary by a step (1) are uniformly mixed by molecular diffusion". In this connection, "interface" means the same as described above.

In addition, in the above-described step (2), "concentrating said analyte and/or at least one kind of reaction improvement CFSs by applying a voltage onto a capillary" means that, as similarly described above, said analyte and/or at least one kind of reaction improvement CFS gather in band-like (plug-like) on application of a voltage onto a capillary. In other words, it means that said substances gather on application of a voltage onto a capillary so that such a portion is generated wherein concentration of said substances becomes higher than that of a substance in a zone arranged in a step (1), namely, it means that an analyte and/or at least one kind of a reaction improvement CFS garher on application of a voltage onto a capillary, and a portion is generated wherein concentration of an analyte and/or concentration of not less than one kind of reaction improvement CFSs becomes higher than that of an analyte and/or not less than one kind of reaction improvement CFSs in a solution zone [for example, a solution zone containing an analyte (for example, (i) a sample including an analyte, (ii) a solution including a sample having an analyte, and not less than one kind of CFSs) and a zone of a solution containing not less than one kind of reaction improvement CFSs] arranged in a step (1).

In the above step (2), "said analyte is electrophoretically contacted with said reaction improvement substance?)" means that, similarly as described above, contact of said analyte and reaction improvement CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), the electrophoresis is conducted, a substance with higher electrophoretic mobility (faster electrophoretic speed) in a solution overtakes a substance with lower electrophoretic mobility (slow electrophoretic speed).

(d) A Case when a Labeled Reaction Improvement CFS is Used.

(1) (a) A solution containing an analyte [for example, (i) a sample including an analyte, (ii) a solution including a sample having an analyte, and not less than one kind of CFSs] and (b) a solution containing not less than one kind of labeled reaction improvement CFSs are introduced and arranged into a capillary so that a zone of the solution containing an analyte [for example, (i) a sample including an analyte, (ii) a solution including a sample having an analyte, and not less than one kind of CFSs], and a zone of a solution including not less than one kind labeled reaction improvement CFSs are separately formed (so that liquid-liquid interface is formed), and a complex between said analyte and labeled reaction improvement CFS is formed on application of a voltage onto said capillary, without mixing these solutions in advance outside a capillary.

(2) Subsequently, said analyte is electrophoretically contacted said labeled reaction improvement CFS while concentrating said analyte and/or at least one kind of a labeled reaction improvement CFS by applying a voltage onto said capillary before uniformly mixing these solutions, not by (not depending on) molecular diffusion and without physically mixing, to form the complex between said analyte and labeled reaction improvement CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], and a solution including not less than one kind labeled reaction improvement CFSs, along with if necessary the liquid, arranged in a capillary by a step (1) are uniformly mixed by molecular diffusion". In this connection, "interface" means the same as described above.

In addition, in the above-described step (2), "concentrating said analyte and/or at least one kind of labeled reaction improvement CFS by applying a voltage onto a capillary" means that, as similarly described above, for said analyte and/or at least one kind of labeled reaction improvement CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that an analyte and/or at least one kind of a labeled reaction improvement CFS garher on application of a voltage onto a capillary, and a portion is generated wherein concentration of an analyte and/or concentration of not less than one kind of labeled reaction improvement CFSs becomes higher than that of an analyte and/or not less than one kind of labeled reaction improvement CFSs in a solution zone [for example, a zone of a solution containing an analyte (for example, (i) a sample including an analyte, (ii) a solution including a sample having an analyte, and not less than one kind of CFSs) and a zone of a solution containing not less than one kind of labeled reaction improvement CFSs] arranged in a step (1).

In the above step (2), "said analyte is electrophoretically contacted with said labeled reaction improvement CFS?)" means that, similarly as described above, contact of said analyte and labeled reaction improvement CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(e) A Case when a CFS not Bound with a Labeling Substance and a Reaction Improvement Substance, and a Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a reaction improvement CFS are introduced and arranged into a capillary so that a zone of the solution containing an analyte [for example, (i) a sample including an analyte, (ii) a solution including a sample having an analyte, and not less than one kind of CFSs], a zone of the solution including not less than one kind of CFSs, and a zone of the solution including not less than one kind of reaction improvement CFSs are separately formed (so that liquid-liquid interface is formed), and a complex between said analyte, CFS and reaction improvement CFS is formed on application of a voltage onto a capillary, without mixing these solutions in advance outside a capillary.

(2) Subsequently, said analyte is electrophoretically contacted with said CFS and reaction improvement CFS while concentrating at least one selected from said analyte, not less than one kind of CFS and not less than one kind of reaction improvement CFS by applying a voltage onto said capillary before uniformly mixing these solutions, not by (not depending on) molecular diffusion and without physically mixing, to form the complex between said analyte, CFS and reaction improvement CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], a solution including not less than one kind of CFSs, and a solution including not less than one kind of reaction improvement CFSs, along with if necessary the liquid, arranged in a capillary by a step (1) are uniformly mixed by molecular diffusion". In this connection, "interface" means the same as described above.

In addition, in the above-described step (2), "concentrating at least one selected from said analyte, not less than one kind of CFS and not less than one kind of reaction improvement CFS, by applying a voltage onto a capillary" means that, as similarly described above, at least one selected from said analyte, not less than one kind of CFS and not less than one kind of reaction improvement CFS gather in band-like (plug-like) on application of a voltage onto a capillary. In other words, it means that said substances gather on application of a voltage onto a capillary so that such a portion is generated wherein concentration of said substances becomes higher than that of a substance in a zone arranged in a step (1), namely, it means that at least one selected from an analyte, not less than one kind of CFS and not less than one kind of reaction improvement CFS garher on application of a voltage onto a capillary, and a portion is generated wherein concentration of an analyte, concentration of not less than one kind of a CFS or concentration of not less than one kind of a reaction improvement CFS becomes higher than that of an analyte, not less than one kind of a CFS or not less than one kind of a reaction improvement CFS in a solution zone [for example, a zone of a solution containing an analyte (for example, (i) a sample including an analyte, (ii) a solution including a sample having an analyte, and not less than one kind of CFSs), a zone of a solution including not less than one kind of CFSs and a zone of a solution including not less than one kind of reaction improvement CFSs] arranged in a step (1).

In the above step (2), "said analyte is electrophoretically contacted with said CFS and reaction improvement CFS" means_that, similarly as described above, contact of said analyte, CFS and reaction improvement CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(f) A Case when a Labeled CFS and a Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a labeled CFS and (c) a solution containing not less than one kind of a reaction improvement CFS are introduced and arranged into a capillary so that a zone of the solution containing an analyte [for example, (i) a sample including an analyte, (ii) a solution including a sample having an analyte, and not less than one kind of CFSs], a zone of the solution containing not less than one kind of labeled CFSs, and a zone of the solution containing not less than one kind of reaction improvement CFSs are separately formed (so that liquid-liquid interface is formed), and a complex between said analyte, labeled CFS and reaction improvement CFS is formed on application of a voltage onto a capillary, without mixing these solutions in advance outside a capillary.

(2) Subsequently, said analyte is electrophoretically contacted with said labeled CFS and reaction improvement CFS while concentrating at least one selected from said analyte, not less than one kind of labeled CFS and not less than one kind of reaction improvement CFS by applying a voltage onto said capillary before uniformly mixing these solutions, not by (not depending on) molecular diffusion and without physically mixing, to form the complex between said analyte, labeled CFS and reaction improvement CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], a solution including not less than one kind of labeled CFSs, and a solution including not less than one kind of reaction improvement CFSs along with if necessary the liquid, arranged in a capillary by a step (1) are uniformly mixed by molecular diffusion". In this connection, "interface" means the same as described above.

In addition, in the above-described step (2), "concentrating at least one selected from said analyte, not less than one kind of labeled CFS and not less than one kind of reaction improvement CFS, by applying a voltage onto a capillary" means that, as similarly described above, at least one selected from said analyte, not less than one kind of labeled CFS and not less than one kind of reaction improvement CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that at least one selected from an analyte, not less than one kind of labeled CFS and not less than one kind of reaction improvement CFS garher on application of a voltage onto a capillary, and a portion is generated wherein concentration of an analyte, concentration of not less than one kind of a labeled CFS or concentration of not less than one kind of a reaction improvement CFS becomes higher than that of an analyte, not less than one kind of a labeled CFS or not less than one kind of a reaction improvement CFS in a solution zone [for example, a zone of a solution containing an analyte (for example, (i) a sample including an analyte, (ii) a solution including a sample having an analyte, and not less than one kind of CFSs), a zone of a solution including not less than one kind of a labeled CFS, and a zone of a solution including not less than one kind of a reaction improvement CFS] arranged in a step (1).

In the above step (2), "said analyte is electrophoretically contacted with said labeled CFS and reaction improvement CFS" means_that, similarly as described above, contact of said analyte, labeled CFS and reaction improvement CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(g) A Case when a CFS not Bound with a Labeling Substance and a Reaction Improvement Substance, and a Labeled Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a labeled reaction improvement CFS are introduced and arranged into a capillary so that a zone of a solution containing an analyte [for example, (i) a sample including an analyte, (ii) a solution including a sample having an analyte, and not less than one kind of CFSs], a zone of the solution including not less than one kind of CFSs, and a zone of the solution containing not less than one kind labeled reaction improvement CFSs are separately formed (so that liquid-liquid interface is formed), and a complex between said analyte, CFS and labeled reaction improvement CFS is formed on application of a voltage onto a capillary, without mixing these solutions in advance outside a capillary.

(2) Subsequently, said analyte is electrophoretically contacted with said CFS and labeled reaction improvement CFS while concentrating at least one selected from said analyte, not less than one kind of CFS and not less than one kind of labeled reaction improvement CFS by applying a voltage onto said capillary before uniformly mixing these solutions, not by (not depending on) molecular diffusion and without physically mixing, to form the complex between said analyte, CFS and labeled reaction improvement CFS.

In the above description, "before these solutions are uniformly mixed" means "before each zone (liquid-liquid interface) of a solution containing an analyte [for example, (i) a sample including an analyte, (ii) a solution including a sample having an analyte, and not less than one kind of CFSs], a solution including not less than one kind of CFSs, and a solution containing not less than one kind labeled reaction improvement CFSs, along with if necessary the liquid, arranged in a capillary by a step (1) are uniformly mixed by molecular diffusion". In this connection, "interface" means the same as described above.

In addition, in the above-described step (2), "concentrating at least one selected from said analyte, not less than one kind of CFS and not less than one kind of labeled reaction improvement CFS, by applying a voltage onto a capillary" means that, as similarly described above, at least one selected from said analyte, not less than one kind of CFS and not less than one kind of labeled reaction improvement CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that at least one selected from an analyte, not less than one kind of CFS and not less than one kind of labeled reaction improvement CFS garher on application of a voltage onto a capillary, and a portion is generated wherein concentration of an analyte, concentration of not less than one kind of a CFS or concentration of not less than one kind of a labeled reaction improvement CFS becomes higher than that of an analyte, not less than one kind of a CFS or not less than one kind of a labeled reaction improvement CFS in a solution zone [for example, a zone of solution containing an analyte (for example, (i) a sample including an analyte, (ii) a solution including a sample having an analyte, and not less than one kind of CFSs), a zone of a solution including not less than one kind of CFSs and a zone of a solution containing not less than one kind labeled reaction improvement CFSs] arranged in a step (1).

In the above step (2), "said analyte is electrophoretically contacted with said CFS and labeled reaction improvement CFS" means that, similarly as described above, contact of said analyte, CFS and labeled reaction improvement CFS is conducted, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

A method for forming a complex of the present invention can also be used in so-called a competitive method. The procedure in carrying it out in a competitive method is as follows:

(h) A Case when a Labeled Analogue and a CFS are Used.

(1) (a) A solution containing a sample having an analyte and a labeled analogue (or a solution including a sample having an analyte, a labeled analogue and not less than one kind of CFSs) and (b) a solution containing not less than one kind of CFSs are introduced and arranged into a capillary so that a zone of the solution containing a sample having an analyte and a labeled analogue (or the solution including a sample having an analyte, a labeled analogue and not less than one kind of CFSs), and a zone of the solution including not less than one kind of CFSs are separately formed (so that liquid-liquid interface is formed), and a complex A between said analyte and CFS and a complex B between said labeled analogue and CFS are formed on application of a voltage onto a capillary, without mixing these solutions in advance outside a capillary.

(2) Subsequently, said analyte and labeled analogue are electrophoretically contacted with said CFS (namely, said analyte is electrophoretically contacted with said CFS, and said labeled analogue electrophoretically contacted with said CFS) while concentrating said analyte and labeled analogue and/or not less than one kind of a CFS by applying a voltage onto said capillary before uniformly mixing these solutions, not by (not depending on) molecular diffusion and without physically mixing, to form the complex A between said analyte and CFS and a complex B between said labeled analogue and CFS.

In the above description, "before these solutions are uniformly mixed" means "before each zone (liquid-liquid interface) of a solution including a sample having an analyte and a labeled analogue (or a solution including a sample having an analyte, a labeled analogue and not less than one kind of CFSs), and a solution including not less than one kind of CFSs, along with if necessary the liquid, arranged in a capillary by a step (1) are uniformly mixed by molecular diffusion". In this connection, "interface" means the same as described above.

In addition, in the above-described step (2), "concentrating said analyte and labeled analogue, and/or not less than one kind of a CFS, by applying a voltage onto a capillary" means that, as similarly described above, said analyte and labeled analogue and/or not less than one kind of CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that an analyte and a labeled analogue, and/or not less than one kind of a CFS garher on application of a voltage onto a capillary, and a portion is generated wherein concentration of an analyte and a labeled analogue, and/or concentration of a CFS becomes higher than that of an analyte and a labeled analogue, and/or not less than one kind of a CFS in a solution zone [for example, a zone of a solution including a sample having an analyte and a labeled analogue (or a solution including a sample having an analyte, a labeled analogue and not less than one kind of CFSs), a zone of a solution containing CFSs] arranged in a step (1).

In the above step (2), "said analyte and labeled analogue are electrophoretically contacted with said CFS (namely, said analyte is electrophoretically contacted with said CFS, and said labeled analogue electrophoretically contacted with said CFS)" means that, similarly as described above, contact of said analyte, labeled analogue and CFS are conducted (contact of each of said analyte and CFS, and labeled analogue and CFS are conducted), not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtake a substance with lower electrophoretic mobility (slow electrophoretic speed).

(i) A Case when a Labeled Analogue and a Reaction Improvement CFS are Used.

(1) (a) A solution including a sample having an analyte and a labeled analogue (or a solution including a sample having an analyte, a labeled analogue and not less than one kind of CFSs) and (b) a solution containing not less than one kind of reaction improvement CFSs are introduced and arranged into a capillary so that a zone of the solution including a sample having an analyte and a labeled analogue (or the solution including a sample having an analyte, a labeled analogue and not less than one kind of CFSs), and a zone of the solution including not less than one kind of reaction improvement CFSs are separately formed (so that liquid-liquid interface is formed), and a complex A between said analyte and reaction improvement CFS and a complex B between said labeled analogue and reaction improvement CFS are formed on application of a voltage onto a capillary, without mixing these solutions in advance outside a capillary.

(2) Subsequently, said analyte and labeled analogue are electrophoretically contacted with said reaction improvement CFS (namely, said analyte is electrophoretically contacted with said reaction improvement CFS, and said labeled analogue is electrophoretically contacted with said reaction improvement CFS) while concentrating said analyte and labeled analogue and/or not less than one kind of said reaction improvement CFS by applying a voltage onto said capillary before uniformly mixing these solutions, not by (not depending on) molecular diffusion and without physically mixing, to form the complex A between said analyte and reaction improvement CFS and a complex B between said labeled analogue and reaction improvement CFS.

In the above description, "before these solutions are uniformly mixed" means "before each zone (liquid-liquid interface) of a solution including a sample having an analyte and a labeled analogue (or a solution including a sample having an analyte, a labeled analogue and not less than one kind of CFSs), and a solution including not less than one kind of reaction improvement CFSs, along with if necessary the liquid, arranged in a capillary by a step (1) are uniformly mixed by molecular diffusion". In this connection, "interface" means the same as described above.

In addition, in the above-described step (2), "concentrating said analyte and labeled analogue, and/or not less than one kind of reaction improvement CFS, by applying a voltage onto a capillary" means that, as similarly described above, said analyte and labeled analogue and/or not less than one kind of reaction improvement CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that an analyte and a labeled analogue, and/or not less than one kind of reaction improvement CFS garher on application of a voltage onto a capillary, and a portion is generated wherein concentration of an analyte and a labeled analogue, and/or concentration of a reaction improvement CFS becomes higher than that of an analyte and a labeled analogue, and/or not less than one kind of a reaction improvement CFS in a solution zone [for example, a zone of a solution including a sample having an analyte and a labeled analogue (or a solution including a sample having an analyte, a labeled analogue and not less than one kind of CFSs), a zone of a solution including reaction improvement CFSs] arranged in a step (1).

In the above step (2), "said analyte and labeled analogue are electrophoretically contacted with said reaction improvement CFS (namely, said analyte is electrophoretically contacted with said reaction improvement CFS, and said labeled analogue is electrophoretically contacted with said reaction improvement CFS)" means that, similarly as described above, contact of said analyte, labeled analogue and reaction improvement CFS are conducted (contact of each of said analyte and reaction improvement CFS, and labeled analogue and reaction improvement CFS are contacted), not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), and the electrophoresis is conducted, a substance with higher electrophoretic mobility (faster electrophoretic speed) in a solution overtakes a substance with lower electrophoretic mobility (slow electrophoretic speed).

(j) A Case when a Labeled Analogue, a CFS and a Reaction Improvement CFS are Used.

(1) (a) A solution containing a sample having an analyte and a labeled analogue (or a solution including a sample having an analyte, a labeled analogue and not less than one kind of CFSs), (b) a solution including not less than one kind of a CFS and (c) a solution including not less than one kind of a reaction improvement CFS are introduced and arranged into a capillary so that a zone of the solution containing a sample having an analyte and a labeled analogue (or the solution containing a sample having an analyte, a labeled analogue and not less than one kind of CFSs), a zone of the solution including not less than one kind of CFSs and a zone of the solution including not less than one kind of reaction improvement CFSs are separately formed (so that liquid-liquid interface is formed), and a complex A between said analyte, CFS and reaction improvement CFS and a complex B between said labeled analogue, CFS and reaction improvement CFS are formed on application of a voltage onto a capillary, without mixing these solutions in advance outside a capillary.

(2) Subsequently, said analyte and labeled analogue are electrophoretically contacted with said CFS and reaction improvement CFS (namely, said analyte is electrophoretically contacted with said CFS and reaction improvement CFS, and said labeled analogue is electrophoretically contacted with said CFS and reaction improvement CFS) while concentrating at least one selected from said analyte and labeled analogue, not less than one kind of a CFS and not less than one kind of a reaction improvement CFS by applying a voltage onto said capillary before uniformly mixing these solutions, not by (not depending on) molecular diffusion and without physically mixing, to form the complex A between said analyte, CFS and reaction improvement CFS and a complex B between said labeled analogue, CFS and reaction improvement CFS.

In the above description, "before these solutions are uniformly mixed" means "before each zone (liquid-liquid interface) of a solution including a sample having an analyte and a labeled analogue (or a solution including a sample having an analyte, a labeled analogue and not less than one kind of CFSs), a solution including not less than one kind of CFSs, and a solution including not less than one kind of reaction improvement CFSs, along with if necessary the liquid, arranged in a capillary by a step (1) are uniformly mixed by molecular diffusion". In this connection, "interface" means the same as described above.

In addition, in the above-described step (2), "concentrating at least one selected from said analyte and labeled analogue, not less than one kind of CFS and not less than one kind of reaction improvement CFS, by applying a voltage onto a capillary" means that, as similarly described above, at least one selected from said analyte and labeled analogue, not less than one kind of CFS and not less than one kind of reaction improvement CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that at least one selected from an analyte and labeled analogue, not less than one kind of CFS and not less than one kind of reaction improvement CFS garher on application of a voltage onto a capillary, and a portion is generated wherein concentration of an analyte and a labeled analogue, concentration of not less than one kind of a CFS or concentration of not less than one kind of a reaction improvement CFS becomes higher than that of an analyte and a labeled analogue, not less than one kind of a CFS or not less than one kind of a reaction improvement CFS in a solution zone [for example, a zone of a solution including an analyte and a labeled analogue (or a solution including a sample having an analyte, a labeled analogue and not less than one kind of CFSs), a zone of a solution including not less than one kind of CFSs, and a zone of a solution including not less than one kind of reaction improvement CFSs] arranged in a step (1).

In the above step (2), "said analyte and labeled analogue are electrophoretically contacted with said CFS and reaction improvement CFS (namely, said analyte is electrophoretically contacted with said CFS and reaction improvement CFS, and said labeled analogue is electrophoretically contacted with said CFS and reaction improvement CFS)" means that, similarly as described above, contact of said analyte and labeled analogue, CFS and reaction improvement CFS are conducted (namely, contact of each of said analyte, CFS and reaction improvement CFS, and said labeled analogue, CFS and reaction improvement CFS are conducted), not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

(k) A Case when a Reaction Improvement Analogue and a Labeled CFS are Used.

(1) (a) A solution containing sample having an analyte and reaction improvement analogue (or a solution including a sample having an analyte, a reaction improvement analogue and not less than one kind of CFSs) and (b) a solution including not less than one kind of labeled CFSs are introduced and arranged into a capillary so that a zone of a solution including the sample having an analyte and a reaction improvement analogue (or the solution including a sample having an analyte, a reaction improvement analogue and not less than one kind of CFSs), and a zone of the solution including not less than one kind of labeled CFSs are separately formed (so that liquid-liquid interface is formed), and a complex A between said analyte and labeled CFS and a complex B between said reaction improvement analogue and labeled CFS are formed on application of a voltage onto a capillary, without mixing these solutions in advance outside a capillary.

(2) Subsequently, said analyte and reaction improvement analogue are electrophoretically contacted with said labeled CFS (namely, said analyte is electrophoretically contacted said labeled CFS, and said reaction improvement analogue is electrophoretically contacted with said labeled CFS) while concentrating said analyte and reaction improvement analogue and/or not less than one kind of labeled CFS by applying a voltage onto said capillary, before uniformly mixing these solutions, not by (not depending on) molecular diffusion and without physically mixing, to form the complex A between said analyte and labeled CFS and the complex B between said reaction improvement analogue and labeled CFS.

In the above description, "before these solutions are uniformly mixed" means "before each zone (liquid-liquid interface) of a solution including a sample having an analyte and a reaction improvement analogue (or a solution including a sample having an analyte, a reaction improvement analogue and not less than one kind of CFSs), and a solution including not less than one kind of labeled CFSs, along with if necessary the liquid, arranged in a capillary by a step (1) are uniformly mixed by molecular diffusion". In this connection, "interface" means the same as described above.

In addition, in the above-described step (2), "concentrating said analyte and reaction improvement analogue and/or not less than one kind of labeled CFS, by applying a voltage onto a capillary" means that, as similarly described above, said analyte and reaction improvement analogue and/or not less than one kind of labeled CFS gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that an analyte and reaction improvement analogue and/or not less than one kind of labeled CFS garher on application of a voltage onto a capillary, and a portion is generated wherein concentration of an analyte and a reaction improvement analogue and/or concentration of not less than one kind of a labeled CFS becomes higher than that of an analyte and a reaction improvement analogue, and/or not less than one kind of a labeled CFS in a solution zone [for example, a zone of a solution including an analyte and a reaction improvement analogue (or a solution including a sample having an analyte, a reaction improvement analogue and not less than one kind of CFSs), a solution including not less than one kind of labeled CFSs] arranged in a step (1).

In the above step (2), "said analyte and reaction improvement analogue are electrophoretically contacted with said labeled CFS (namely, said analyte is electrophoretically contacted said labeled CFS, and said reaction improvement analogue is electrophoretically contacted with said labeled CFS)" means that, similarly as described above, contacted s said analyte, reaction improvement analogue and labeled CFS are conducted (namely, contact of each of said analyte and labeled CFS, and said reaction improvement analogue and labeled CFS are conducted), not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

(l) A Case when a Labeled Analogue and a CFS are Used.

(1) (a) A solution including a sample having an analyte, and not less than one kind of CFSs, and (b) a solution containing a labeled analogue are introduced and arranged into a capillary so that a zone of a solution including a sample having an analyte, and not less than one kind of CFSs, and a zone of a solution including a labeled analogue are separately formed (so that liquid-liquid interface is formed), and a complex B between said labeled analogue and CFS is formed on application of a voltage onto a capillary, without mixing these solutions in advance outside a capillary.

(2) Subsequently, said labeled analogue is electrophoretically contacted with CFS (namely, said labeled analogue is electrophoretically contacted with said CFS not involved in the formation of a complex (complex A) with said analyte in the said solution including a sample having an analyte, and not less than one kind of CFSs) while concentrating said labeled analogue and/or said CFS not involved in the formation of a complex A by applying a voltage onto said capillary before uniformly mixing these solutions, not by (not depending on) molecular diffusion and without physically mixing, to form the complex B between said labeled analogue and CFS.

In the above description, "before these solutions are uniformly mixed" means "before each zone (liquid-liquid interface) of a solution including a sample having an analyte, and not less than one kind of CFSs, and a solution including a labeled analogue, along with if necessary the liquid, arranged in a capillary by a step (1) are uniformly mixed by molecular diffusion". In this connection, "interface" means the same as described above.

In addition, in the above-described step (2), "concentrating said labeled analogue and/or said CFS not involved in the formation of a complex A, by applying a voltage onto a capillary" means that, as similarly described above, said labeled analogue and/or said CFS not involved in the formation of a complex A gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that said labeled analogue and/or said CFS not involved in the formation of a complex A garher on application of a voltage onto a capillary, and a portion is generated wherein concentration of a concentration of a labeled analogue and/or a concentration of a CFS not involved in the formation of a complex A becomes higher than that of a labeled analogue and/or a CFS not involved in the formation of a complex A in a solution zone [for example, a zone of a solution including a sample having an analyte, and not less than one kind of CFSs, and a zone of a solution including a labeled analogue] arranged in a step (1).

In the above step (2), "said labeled analogue is electrophoretically contacted with CFS (namely, said labeled analogue is electrophoretically contacted with said CFS not involved in the formation of the complex (complex A) with said analyte in the said solution including a sample having an analyte, and not less than one kind of CFSs)" means that, similarly as described above, contact of said labeled analogue and CFS are conducted (namely, contact of said labeled analogue and said CFS not involved in the formation of the complex (complex A) with said analyte in the said solution including a sample having an analyte, and not less than one kind of CFSs) not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

(m) A Case when a Labeled Analogue and a Reaction Improvement CFS are Used.

(1) (a) A solution containing a sample having an analyte, and not less than one kind of reaction improvement CFSs, and (b) a solution containing a labeled analogue are introduced and arranged into a capillary so that a zone of a solution including a sample having an analyte, and not less than one kind of reaction improvement CFSs, and a zone of a solution including a labeled analogue are separately formed (so that liquid-liquid interface is formed), and a complex B between said labeled analogue and reaction improvement CFS is formed on application of a voltage onto a capillary, without mixing these solutions in advance outside a capillary.

(2) Subsequently, said labeled analogue is electrophoretically contacted with said reaction improvement CFS (namely, said labeled analogue is electrophoretically contacted with said reaction improvement CFS not involved in the formation of a complex (complex A) with said analyte in the said solution including a sample having an analyte, and not less than one kind of reaction improvement CFS) while concentrating said labeled analogue and/or said reaction improvement CFS not involved in the formation of a complex A by applying a voltage onto said capillary before uniformly mixing these solutions, not by (not depending on) molecular diffusion and without physically mixing, to form the complex B between said labeled analogue and reaction improvement CFS.

In the above description, "before these solutions are uniformly mixed" means "before each zone (liquid-liquid interface) of a solution including a sample having an analyte, and not less than one kind of reaction improvement CFSs, and a solution including a labeled analogue, along with if necessary the liquid, arranged in a capillary by a step (1) are uniformly mixed by molecular diffusion". In this connection, "interface" means the same as described above.

In addition, in the above-described step (2), "concentrating said labeled analogue and/or said reaction improvement CFS not involved in the formation of a complex A, by applying a voltage onto a capillary" means that, as similarly described above, said labeled analogue and/or said reaction improvement CFS not involved in the formation of a complex A gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that a labeled analogue and/or a reaction improvement CFS not involved in the formation of a complex A garher on application of a voltage onto a capillary, and a portion is generated wherein concentration of a labeled analogue and/or concentration of a reaction improvement CFS not involved in the formation of a complex A becomes higher than that of a labeled analogue and/or a reaction improvement CFS not involved in the formation of a complex A in a solution zone [for example, a zone of a solution including a sample having an analyte, and not less than one kind of reaction improvement CFSs, and a zone of a solution including a labeled analogue] arranged in a step (1).

In the above step (2), "said labeled analogue is electrophoretically contacted with said reaction improvement CFS (namely, said labeled analogue is electrophoretically contacted with said reaction improvement CFS not involved in the formation of a complex (complex A) with said analyte in the said solution including a sample having an analyte, and not less than one kind of reaction improvement CFS)" means that, similarly as described above, contact of said labeled analogue and reaction improvement CFS are conducted (namely, contacted said labeled analogue and said reaction improvement CFS not involved in the formation of the complex (complex A) with said analyte in the said solution including a sample having an analyte, and not less than one kind of reaction improvement CFS) not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

(n) A Case when a Labeled Analogue, a CFS and a Reaction Improvement CFS are Used.

(1) (a) A solution containing a sample having an analyte and not less than one kind of a CFS (or not less than one kind of a reaction improvement CFS), (b) a solution containing a labeled analogue and (c) a solution containing not less than one kind of a reaction improvement CFS (or not less than one kind of a CFS) are introduced and arranged into a capillary so that a zone of the solution including a sample having an analyte and at least one kind of a CFS (or not less than one kind of a reaction improvement CFS), a zone of the solution including a labeled analogue and a zone of a solution including not less than one kind of a reaction improvement CFS (or not less than one kind of a CFS) are separately formed (so that liquid-liquid interface is formed), and a complex A between said analyte, CFS and reaction improvement CFS and a complex B between said labeled analogue, CFS and reaction improvement CFS are formed on application of a voltage onto a capillary, without mixing these solutions in advance outside a capillary.

(2) Subsequently, said analyte and labeled analogue are electrophoretically contacted with said CFS and reaction improvement CFS [namely, a comple between said analyte and CFS (or reaction improvement CFS) in said solution (a) is electrophoretically contacted with said reaction improvement CFS (or CFS) in said solution (c), and said labeled analogue is electrophoretically contacted with said CFS (or reaction improvement CFS) not involved in the formation of said complex with said analyte in said solution (a) and said reaction improvement CFS (or CFS) in said solution (c)] while concentrating at least one selected from the complex A between said analyte and not less than one kind of CFS (or not less than one kind of reaction improvement CFS), labeled analogue, and not less than one kind of reaction improvement CFS (or not less than one kind of CFS) by applying a voltage onto said capillary before uniformly mixing these solutions, not depending on molecular diffusion and without physically mixing, to form the complex A between said analyte, CFS and reaction improvement CFS and the complex B between said labeled analogue, CFS and reaction improvement CFS.

In the above description, "before these solutions are uniformly mixed" means "before each zone (liquid-liquid interface) of a solution including a sample having an analyte and not less than one kind of a CFS (or not less than one kind of a reaction improvement CFS), a solution including a labeled analogue and a solution including not less than one kind of reaction improvement CFSs (or not less than one kind of a CFS), along with if necessary the liquid, arranged in a capillary by a step (1) are uniformly mixed by molecular diffusion". In this connection, "interface" means the same as described above.

In addition, in the above-described step (2), "concentrating at least one selected from said complex between said analyte and not less than one kind of a CFS (or not less than one kind of a reaction improvement CFS), said labeled analogue, and not less than one kind of a reaction improvement CFS (or not less than one kind of a CFS), by applying a voltage onto a capillary" means that, as similarly described above, at least one selected from said complex between said analyte and not less than one kind of a CFS (or not less than one kind of a reaction improvement CFS), said labeled analogue, and not less than one kind of a reaction improvement CFS (or not less than one kind of a CFS) gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that at least one selected from a complex between said analyte and not less than one kind of a CFS (or not less than one kind of a reaction improvement CFS), a labeled analogue, and not less than one kind of a reaction improvement CFS (or not less than one kind of a CFS) garher on application of a voltage onto a capillary, and a portion is generated wherein concentration of a complex between said analyte and not less than one kind of a CFS (or not less than one kind of a reaction improvement CFS), concentration of a labeled analogue or concentration of not less than one kind of a reaction improvement CFS (or not less than one kind of a CFS) becomes higher than that of a complex between said analyte and at least one kind of a CFS (or not less than one kind of a reaction improvement CFS), a labeled analogue, or not less than one kind of a reaction improvement CFS (or not less than one kind of a CFS) in a solution zone [for example, a zone of a solution including a sample having an analyte and not less than one kind of a CFS (or not less than one kind of a reaction improvement CFS), a zone of a solution including a labeled analogue and a zone of a solution including not less than one kind of reaction improvement CFSs (or not less than one kind of a CFS)] arranged in a step (1).

In the above step (2), "said analyte and labeled analogue are electrophoretically contacted with said CFS and reaction improvement CFS [namely, a comple between said analyte and CFS (or reaction improvement CFS) in said solution (a) is electrophoretically contacted with said reaction improvement CFS (or CFS) in said solution (c), and said labeled analogue is electrophoretically contacted with said CFS (or reaction improvement CFS) not involved in the formation of said complex with said analyte in said solution (a) and said reaction improvement CFS (or CFS) in said solution (c)]" means that, similarly as described above, contacted said analyte, labeled analogue, CFS and reaction improvement CFS are conducted [namely, contact of said comple between said analyte and CFS (or reaction improvement CFS) in said solution (a) and said reaction improvement CFS (or CFS) in said solution (c), and said labeled analogue, said CFS (or reaction improvement CFS) not involved in the formation of said complex with said analyte in said solution (a) and said reaction improvement CFS (or CFS) in said solution (c) are conducted], not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

(o) A Case when a Reaction Improvement Analogue and a Labeled CFS are Used.

(1) (a) A solution containing a sample having an analyte, and not less than one kind of labeled CFSs, and (b) a solution containing a reaction improvement analogue are introduced and arranged into a capillary so that a zone of a solution including a sample having an analyte, and not less than one kind of labeled CFSs, and a zone of a solution including a reaction improvement analogue are separately formed (so that liquid-liquid interface is formed), and a complex B between said reaction improvement analogue and labeled CFS is formed on application of a voltage onto a capillary, without mixing these solutions in advance outside a capillary.

(2) Subsequently, said reaction improvement analogue is electrophoretically contacted with labeled CFS (namely, said reaction improvement analogue is electrophoretically with said labeled CFS not involved in the formation of a complex (complex A) with said analyte in the said solution including a sample having an analyte, and not less than one kind of labeled CFSs) while concentrating said reaction improvement and/or said labeled CFS not involved in the formation of a complex A analogue by applying a voltage onto said capillary before uniformly mixing these solutions, not by (not depending on) molecular diffusion and without physically mixing, to form the complex B between said reaction improvement analogue and labeled CFS.

In the above description, "before these solutions are uniformly mixed" means "before each zone (liquid-liquid interface) of a solution including a sample having an analyte, and not less than one kind of labeled CFSs, and a solution including a reaction improvement analogue, along with if necessary the liquid, arranged in a capillary by a step (1) are uniformly mixed by molecular diffusion". In this connection, "interface" means the same as described above.

In addition, in the above-described step (2), "concentrating a reaction improvement analogue and/or a labeled CFS not involved in the formation of a complex A, by applying a voltage onto a capillary" means that, as similarly described above, a reaction improvement analogue and/or a labeled CFS not involved in the formation of a complex A gather in band-like (plug-like) on application of a voltage onto a capillary. In other words, it means that said substances gather on application of a voltage onto a capillary so that such a portion is generated wherein concentration of said substances becomes higher than a substance in a zone arranged in a step (1), namely, it means that said reaction improvement analogue and/or said labeled CFS not involved in the formation of a complex A garher on application of a voltage onto a capillary, and a portion is generated wherein concentration of concentration of a reaction improvement analogue and/or concentration of a labeled CFS not involved in the formation of a complex A becomes higher than that of a reaction improvement analogue and/or a labeled CFS not involved in the formation of a complex A in a solution zone [for example, a zone of a solution including an analyte, and not less than one kind of labeled CFSs, and a zone of a solution including a reaction improvement analogue] arranged in a step (1).

In the above step (2), "said reaction improvement analogue is electrophoretically contacted with labeled CFS (namely, said reaction improvement analogue is electrophoretically with said labeled CFS not involved in the formation of a complex (complex A) with said analyte in the said solution including a sample having an analyte, and not less than one kind of labeled CFSs)" means that, similarly as described above, contact of said reaction improvement analogue and labeled CFS are conducted (namely, contact of said reaction improvement analogue and said labeled CFS not involved in the formation of a complex (complex A) with said analyte in the said solution including a sample having an analyte, and not less than one kind of labeled CFSs is conducted not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed), a substance with higher electrophoretic mobility (faster electrophoretic speed) in a solution overtakes a substance with lower electrophoretic mobility (slow electrophoretic speed).

In the above-described methods (a) to (o), as for level (degree) of concentration of a substance to be concentrated [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.], concentration of a substance [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.] at an gathered part (in band-like) of said substance on application of a voltage onto a capillary, relative to concentration of an substance [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.] in a solution zone arranged by a step (1) is, as lower limit, usually not lower than 1.5 times, preferably not lower than 5 times, more preferably not lower than 10 times, and further preferably not lower than 25 times, and upper limit is not especially limited, however usually not higher than $10^7$ times, preferably not higher than $10^6$ times and more preferably not higher than $10^5$ times.

In addition, in the above-described methods (a) to (o), "contacted while concentrating" means, similarly as described above, both cases when concentration and contact are simultaneously carried out, and a case when contact is carried out after concentration is substantially completed, and therefore encompasses so-called all the cases other than a case when concentration is carried out after contact is substantially completed.

In the above-described methods (a) to (o), a step (2) can be carried out, similarly as described above, before a solution arranged in a capillary by a step (1) is uniformly mixed under conditions enabling concentration, contacting and formation of a complex, by applying a voltage onto said capillary.

In the above-described methods (a) to (o), a step (2) can be carried out, similarly as described above by applying a voltage onto said capillary under condition that concentration, contacting and formation of a complex can be carried out by applying a voltage onto said capillary, before a solution arranged in a capillary by a step (1) is uniformly mixed.

Specific examples, preferable embodiments, and the like of such conditions are as described above, and for example, the above step (2) may be carried out in accordance with the above-described method for concentration, in suitable consideration of electrophoretic mobility of an analyte, a CFS, a labeled CFS, a reaction improvement CFS, a labeled reaction improvement CFS, a labeled analogue, a reaction improvement analogue, a complex composed of 2 or more kinds thereof, to be used, or electric conductivity of solutions including these.

In addition, applied voltage and other reaction conditions (for example, pH, temperature, time, etc.), and the like in a step (2) may also suitably be determined from a range as described above, in consideration of an analyte, a CFS, a labeled CFS, a reaction improvement CFS, a labeled reaction improvement CFS, a labeled analogue, a reaction improvement analogue, a complex composed of 2 or more kinds thereof, solutions including these, and the like.

2. A Method for Separation of the Present Invention

A method for separation of the present invention features in electrical separation of a complex between an analyte or an analogue thereof and not less than one kind of CFSs, formed by a method for formation of a complex of the present invention as described above, and a CFS not involved in formation of said complex or an analogue not involved in formation of said complex.

Namely, the features is that a complex between an analyte or an analogue thereof and a CFS in a solution, formed by each contact by electrophoretically moving (migrating) in a capillary in a step (2) of the present invention, and a CFS not involved in formation of said complex or an analogue not involved in formation of said complex are further electrophoretically moved (migrated) and are separated.

A method for separation of the present invention may be carried out in accordance with a known method itself except in electrically separating a complex between an analyte or an analogue thereof and not less than one kind of CFSs, and a CFS not involved in formation of said complex or an analogue not involved in formation of said complex, in a known method itself for separating a substance by electric movement (migration) using, for example, a capillary, and as for material and reagents to be used also, those used in known methods themselves may be used.

Therefore, a method for separation of the present invention includes the following steps (1) to (3):

(1) a step (a step of introduction) of arranging (a) a solution containing an analyte or an analogue thereof and (b) a solution containing not less than one kind of a substance formable the complex (the CFS) with said analyte or said analogue thereof, in a capillary, so that by applying a voltage to said capillary the complex between said analyte or analogue thereof and the CFS are formed without mixing these solutions in advance;

(2) a step (a step of concentrating reaction) of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS; and (3) a step (a step of separation) of separating said complex and the CFS not involved in the formation of said complex or the analogue not involved in the formation of said complex by further electrical movement (migration).

In this connection, in the above description, embodiments, a specific example, a preferable example, and the like of an analyte, an analogue (a labeled analogue, a reaction improvement analogue, etc.), a solution containing an analyte or an analogue thereof, a sample including an analyte, a CFS (a labeled CFS, a reaction improvement CFS, a labeled reaction improvement CFS, etc.), solutions including these, a step of introduction [a step (1)], a step of a concentrating reaction [a step (2)], are as described above.

2-1. A Step of Separation [a Step (3)]

As described above, a complex between an analyte or an analogue thereof and a CFS, obtained by steps (1) and (2) of the present invention, and a CFS not involved in formation of said complex or an analogue not involved in formation of said complex, are separated in a capillary, by further electrical movement (migration).

A method for separation of the present invention is for separation of a complex between an analyte or an analogue thereof and a CFS, and a CFS not involved in formation of said complex or an analogue not involved in formation of said complex, and in more specifically, (1) for separation of a complex between said analyte and CFS, and a CFS not involved in formation of said complex, by further electrical movement (migration); or (2) for separation of a complex between said analogue and CFS, and an analogue not involved in formation of said complex or a complex between said analyte and CFS not involved in formation of said complex, by further electrical movement (migration).

For example, when a method for separation of the present invention is used in a non-competitive method (for example, methods (a) to (g) to be described later, and the like), and when a CFS including a labeling substance (a labeled CFS or a labeled reaction improvement CFS) is used, separation of at least a CFS including a labeling substance not involved (free labeling substances) in formation of a complex between an analyte and a CFS, and a complex including an analyte is enough. Though separation of a CFS not including a labeling substance, from said complex is not necessarily required, separation of said complex and all of the CFSs not involved (free CFSs) in formation of a complex is preferable.

In addition, for example, when a method for separation of the present invention is used in a competitive method (for example, methods (h) to (o) to be described later, and the like), and when a labeled analogue is used, separation of at least a (final) complex between a labeled analogue and (all of the) CFSs, and a labeled analogue not involved (free labeled analogue) in formation of said complex is enough. Separation of a complex between an analyte and a CFS, and a (final) complex between a labeled analogue and (all of the) CFSs is not necessarily required. In addition, when a reaction improvement analogue is used, separation of at least a complex between a reaction improvement analogue and a labeled CFS, and a complex between an analyte and a labeled CFS is enough.

A step (3) of the present invention may be carried out using a method which enables to sufficiently separate a complex between an analyte or an analogue thereof and a CFS, and a CFS not involved in formation of said complex or an analogue not involved in formation of said complex. As such a method, a known electrophoresis method itself and usually used in this field can be used.

Specifically, electrophoresis methods based on various principles (separation modes) can be used. Examples of such method are ITP, IF, as described above; so-called a capillary zone electrophoresis method (CZE) for separation of an objective substance by moving each substance in different speed depending on intensity of a charge thereof, wherein a capillary is fundamentally filled with only a buffer solution for electrophoresis, [Reference: H. Hisamoto at al., Chem. Commun., (2001), 2662, and the like]; so-called a micelle electro kinetic chromatography (MEKC) using a charged substance forming an ionic micelle, and separating a objective substance by interaction with said micelle, [Reference: S. Terabe, Trends Anal. Chem., (1989), 8, 129, and the like]; so-called a capillary gel electrophoresis method (CGE) for separating an objective substance by using a filler such as a polymer having molecular sieve effect, and by charge of a molecule and size of a molecule inducing interaction with a polymer, [Reference: S. Hjerten, J. Chromatogr., (1987), 397, 409, and the like].

In this connection, in the present invention, reagents, and the like used in an electrophoresis method as described above can be used, as appropriate. In addition, these reagents, an operation method in separation, conditions, and the like can suitably be selected in accordance with the description in references, as described above, and the like.

As an electrophoresis method used in a step (3) of the present invention, any of an electrophoresis method based on the same principle (separation mode) as in a concentration method used in a step (2), or an electrophoresis method based on different principle (separation mode) as in a concentration method used in a step (2) may be used.

In this connection, when use of an electrophoresis method based on the same principle (separation mode) as in a step (2) provides insufficient separation of a complex between an analyte or an analogue thereof and a CFS, and a CFS not involved in formation of said complex or an analogue not involved in formation of said complex, use of an electrophoresis method based on different principle (separation mode) as in a concentration method used in a step (2) to carry out a step (3) of the present invention is desirable.

In such a case, execution of ITP, FASS, and the like in a step (2), and subsequently CZE, and the like in a step (3) is particularly preferable.

As described above, in a separation method of the present invention, the following 2 cases are included: (i) contact of said analyte or analogue thereof and CFS is conducted while concentrating an analyte or an analogue thereof and/or at least one kind of a CFS, to form a complex between said analyte or analogue thereof and CFS by a step (2) (in other words, contact of said analyte or analogue thereof and CFS is conducted by applying a voltage onto said capillary under such condition as an analyte or an analogue thereof and/or at least one kind of a CFS are concentrated, to form a complex between said analyte or analogue thereof and CFS), and subsequently by using the same separation mode without changing applied voltage (in other words, while applying a voltage with the same intensity under the same condition as in a step (2)), said complex and CFS not involved in formation of said complex or analogue not involved in formation of said complex are separated by further electric moving (migrating); (ii) or contact of said analyte or analogue thereof and CFS is conducted while concentrating an analyte or an analogue thereof and/or at least one kind of a CFS, to form a complex between said analyte or analogue thereof and CFS by a step (2) (in other words, contact of said analyte or analogue thereof and CFS is conducted by applying a voltage onto said capillary under such condition as an analyte or an analogue thereof and/or at least one kind of a CFS are concentrated, to form a complex between said analyte or analogue thereof and CFS), and subsequently by using different separation mode and/or different applied voltage [in other words, by changing condition (separation mode used) from that in a step (2) and/or intensity of voltage to be applied], said complex and a CFS not involved in formation of said complex or an analogue not involved in formation of said complex are separated by further electric moving (migrating).

As for applied voltage in a step (3), any range may be adopted as long as a complex between an analyte or an analogue thereof and a CFS, and a CFS not involved in formation of said complex or an analogue not involved in formation of said complex are sufficiently separated, and it is suitably selected from a range usually used in this field. In more specifically, the voltage is applied so that electric field intensity is in a range of usually, as lower limit, not lower than 5 V/cm, preferably not lower than 10 V/cm, more preferably not lower than 50 V/cm, further preferably not lower than 500 V/cm, particularly preferably not lower than 1000 V/cm, and as upper limit, usually not higher than 10000 V/cm, preferably not higher than 5000 V/cm, and more preferably not higher than 2000 V/cm. In this connection, as described above, applied voltage in a step (3) may be the same as or different from that in a step (2).

In addition, other separation conditions (for example, pH, temperature, time, and the like) may be any range as long as a complex of an analyte or an analogue thereof and a CFS, and a CFS not involved in formation of said complex or an analogue not involved in formation of said complex are sufficiently separated, and it is suitably selected in accordance with a known method itself usually used in this field.

Specifically, although not simply described due to dependency on property of an analyte or an analogue thereof and a CFS, however, lower limit of the pH is usually not lower than 2, preferably not lower than 4, and more preferably not lower than 5, and upper limit is not higher than 13, preferably not higher than 11 and more preferably not higher than 9. Lower limit of the temperature is usually not lower than 0° C., preferably not lower than 5° C. and more preferably not lower than 10° C., and upper limit is usually not higher than 90° C., preferably not higher than 80° C., more preferably not higher than 50° C., further preferably not higher than 40° C., and particularly preferably not higher than 30° C. In addition, lower limit of the time is usually not shorter than 1 minute, preferably not shorter than 2 minutes and more preferably not shorter than 3 minutes, and upper limit is not longer than 20 minutes and more preferably not longer than 10 minutes.

As described above, a step (3) is carried out in a capillary, and as such a capillary, the same one as used in a step (2) is included, and material and inner diameter of the capillary are also as described above.

In addition, a step (3) of the present invention is carried out usually in a state that an electrophoresis medium such as a buffer solution for electrophoresis or said buffer solution for electrophoresis containing fillers, is filled in a capillary (in separation region as described above. In this connection, a specific example, use concentration, pH, molecular weight, viscosity, an introduction method into a capillary, introduction timing, and the like of an electrophoresis medium are the same as described above.

In this connection, as described above, when a step (3) of the present invention is carried out using an electrophoresis method based on different principle (separation mode) from that in a concentration method used in a step (2), an electrophoresis medium used in a step (2) and an electrophoresis medium used in a step (3) are not required to be the same, and a different electrophoresis medium may be used by suitable selection thereof.

In this connection, steps (2) and (3) of the present invention are usually carried out using the same capillary (in the same capillary). Namely, a capillary used in a separation method of the present invention has at least a part enabling to carry out a step (1) of the present invention, a part enabling to carry out a step (2) of the present invention, and a part enabling to carry out a step (3) of the present invention. These parts may be present each independently in a capillary, or a part of or all of these parts may be present in overlapped state. In other words, as a result, a capillary used in a separation method of the present invention is one, which enables to arrange in a capillary (a) a solution containing an analyte or an analogue thereof and (b) a solution containing not less than one kind of substances formable a complex (a CFS) with said analyte or analogue thereof, so that by applying a voltage onto said capillary the complex between said analyte or analogue thereof and CFS is formed without mixing these solutions in advance, and enables to contact said analyte or analogue thereof and CFS while concentrating said analyte or analogue thereof and/or at least one kind of CFS by applying a voltage onto said capillary, before uniformly mixing these solutions, to form the complex between said analyte or analogue thereof and CFS, and further enables to separate said complex and a CFS not involved in formation of said complex or an analogue not involved in formation of said complex, by further electrical movement (migration?).

2-2. Specific Methods for Separation

Modes for carrying out the methods for separation of the present invention are specifically shown below.

(a) A Case when a CFS not Bound with a Labeling Substance and a Reaction Improvement Substance are Used.

(1) (a) A solution containing an analyte [for example, (i) a sample including an analyte, (ii) a solution including a sample having an analyte, and not less than one kind of CFSs] and (b) a solution containing not less than one kind of CFSs are introduced and arranged into a capillary, as the above-described step (1) in the case (a) of "1-6. Specific methods for forming a complex", (2) Subsequently, said analyte is electrophoretically contacted with said CFS to form the complex between said analyte and the CFS, as the above-described step (2) in the case (a) of "1-6. Specific methods for forming a complex", and (3) Said complex and CFS not involved in formation of said complex are separated in a separation region of a capillary by further electric movement (migration).

(b) A Case when a Labeled CFS is Used.

(1) (a) A solution containing an analyte [for example, (i) a sample including an analyte, (ii) a solution including a sample having an analyte, and not less than one kind of CFSs] and (b) a solution containing not less than one kind of labeled CFSs are introduced and arranged into a capillary, as the above-described step (1) in the case (b) of "1-6. Specific methods for forming a complex", (2) Subsequently, said analyte is electrophoretically contacted with said labeled CFS to form the complex between said analyte and labeled CFS, as the above-described step (2) in the case (b) of "1-6. Specific methods for forming a complex", and (3) Said complex and said labeled CFS not involved in formation of said complex are separated in a separation region of a capillary by further electric movement (migration).

(c) A Case when a Reaction Improvement CFS is Used.

(1) (a) A solution containing an analyte [for example, (i) a sample including an analyte, (ii) a solution including a sample having an analyte, and not less than one kind of CFSs] and (b) a solution containing not less than one kind of reaction improvement CFSs are introduced and arranged into a capillary, as the above-described step (1) in the case (c) of "1-6. Specific methods for forming a complex", (2) Subsequently, said analyte is electrophoretically contacted with said reaction improvement CFS to form the complex between said analyte and reaction improvement CFS, as the above-described step (2) in the case (c) of "1-6. Specific methods for forming a complex", and (3) Said complex and said reaction improvement CFS not involved in formation of said complex are separated in a separation region of a capillary by further electric movement (migration).

(d) A Case when a Labeled Reaction Improvement CFS is Used.

(1) (a) A solution containing an analyte [for example, (i) a sample including an analyte, (ii) a solution including a sample having an analyte, and not less than one kind of CFSs] and (b) a solution containing not less than one kind of labeled reaction improvement CFSs are introduced and arranged into a capillary, as the above-described step (1) in the case (d) of "1-6. Specific methods for forming a complex", (2) Subsequently, said analyte is electrophoretically contacted said labeled reaction improvement CFS to form the complex between said analyte and labeled reaction improvement CFS, as the above-described step (2) in the case (d) of "1-6. Specific methods for forming a complex", and (3) Said complex and said labeled reaction improvement CFS not involved in formation of said complex are separated in a separation region of a capillary by further electric movement (migration).

(e) A Case when a CFS not Bound with a Labeling Substance and a Reaction Improvement Substance, and a Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a reaction improvement CFS are introduced and arranged into a capillary, as the above-described step (1) in the case (e) of "1-6. Specific methods for forming a complex", (2) Subsequently, said analyte is electrophoretically contacted with said CFS and reaction improvement CFS to form the complex between said analyte, CFS and reaction improvement CFS, as the above-described step (2) in the case (e) of "1-6. Specific methods for forming a complex", and (3) Said complex and said CFS not involved in formation of said complex and optionally a reaction improvement CFS not involved in formation of said complex are separated in a separation region of a capillary by further electric movement (migration).

(f) A Case when a Labeled CFS and a Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a labeled CFS and (c) a solution containing not less than one kind of a reaction improvement CFS are introduced and arranged into a capillary, as the above-described step (1) in the case (f) of "1-6. Specific methods for forming a complex", (2) Subsequently, said analyte is electrophoretically contacted with said labeled CFS and reaction improvement CFS to form the complex between said analyte, labeled CFS and reaction improvement CFS, as the above-described step (2) in the case (f) of "1-6. Specific methods for forming a complex", and (3) Said complex and said labeled CFS not involved in formation of said complex and optionally a reaction improvement CFS not involved in formation of said complex are separated in a separation region of a capillary by further electric movement (migration).

(g) A Case when a CFS not Bound with a Labeling Substance and a Reaction Improvement Substance, and a Labeled Reaction Improvement CFS are Used.

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a labeled reaction improvement CFS are introduced and arranged into a capillary, as the above-described step (1) in the case (g) of "1-6. Specific methods for forming a complex", (2) Subsequently, said analyte is electrophoretically contacted with said CFS and labeled reaction improvement CFS to form the complex between said analyte, CFS and labeled reaction improvement CFS, as the above-described step (2) in the case (g) of "1-6. Specific methods for forming a complex", and (3) Said complex and said labeled reaction improvement CFS not involved in formation of said complex and optionally a CFS not involved in formation of said complex are separated in a separation region of a capillary by further electric movement (migration).

A method for separation of the present invention can also be used in so-called a competitive method. The procedure in carrying it out in a competitive method is as follows:

(h) A Case when a Labeled Analogue and a CFS are Used.

(1) (a) A solution containing a sample having an analyte and a labeled analogue (or a solution including a sample having an analyte, a labeled analogue and not less than one kind of CFSs) and (b) a solution containing not less than one kind of CFSs are introduced and arranged into a capillary, as the above-described step (1) in the case, (h) of "1-6. Specific methods for forming a complex", (2) Subsequently, said analyte and labeled analogue are electrophoretically contacted with said CFS (namely, said analyte is electrophoretically contacted with said CFS, and said labeled analogue electrophoretically contacted with said CFS) to form the complex A between said analyte and CFS and a complex B between said labeled analogue and CFS, as the above-described step (2) in the case (h) of "1-6. Specific methods for forming a complex", and (3) Said complex B and said labeled analogue not involved in formation of said complex B are separated in a separation region of a capillary by further electric movement (migration).

(i) A Case when a Labeled Analogue and a Reaction Improvement CFS are Used.

(1) (a) A solution including a sample having an analyte and a labeled analogue (or a solution including a sample having an analyte, a labeled analogue and not less than one kind of CFSs) and (b) a solution containing not less than one kind of reaction improvement CFSs are introduced and arranged into a capillary, as the above-described step (1) in the case (i) of "1-6. Specific methods for forming a complex", (2) Subsequently, said analyte and labeled analogue are electrophoretically contacted with said reaction improvement CFS (namely, said analyte is electrophoretically contacted with said reaction improvement CFS, and said labeled analogue is electrophoretically contacted with said reaction improvement CFS) to form the complex A between said analyte and reaction improvement CFS and a complex B between said labeled analogue and reaction improvement CFS, as the above-described step (2) in the case (i) of "1-6. Specific methods for forming a complex", and (3) Said complex B and said labeled analogue not involved in formation of said complex B are separated in a separation region of a capillary by further electric movement (migration).

(j) A Case when a Labeled Analogue, a CFS and a Reaction Improvement CFS are Used.

(1) (a) A solution containing a sample having an analyte and a labeled analogue (or a solution including a sample having an analyte, a labeled analogue and not less than one kind of CFSs), (b) a solution including not less than one kind of a CFS and (c) a solution including not less than one kind of a reaction improvement CFS are introduced and arranged into a capillary, as the above-described step (1) in the case (j) of "1-6. Specific methods for forming a complex", (2) Subsequently, said analyte and labeled analogue are electrophoretically contacted with said CFS and reaction improvement CFS (namely, said analyte is electrophoretically contacted with said CFS and reaction improvement CFS, and said labeled analogue is electrophoretically contacted with said CFS and reaction improvement CFS) to form the complex A between said analyte, CFS and reaction improvement CFS and a complex B between said labeled analogue, CFS and reaction improvement CFS, as the above-described step (2) in the case (j) of "1-6. Specific methods for forming a complex", and (3) Said complex B and said labeled analogue not involved in formation of said complex B are separated in a separation region of a capillary by further electric movement (migration).

(k) A Case when a Reaction Improvement Analogue and a Labeled CFS are Used.

(1) (a) A solution containing sample having an analyte and reaction improvement analogue (or a solution including a sample having an analyte, a reaction improvement analogue and not less than one kind of CFSs) and (b) a solution including not less than one kind of labeled CFSs are introduced and arranged into a capillary, as the above-described step (1) in the case (k) of "1-6. Specific methods for forming a complex", (2) Subsequently, said analyte and reaction improvement analogue are electrophoretically contacted with said labeled CFS (namely, said analyte is electrophoretically contacted said labeled CFS, and said reaction improvement analogue is electrophoretically contacted with said labeled CFS) to form the complex A between said analyte and labeled CFS and the complex B between said reaction improvement analogue and labeled CFS, as the above-described step (2) in the case (k) of "1-6. Specific methods for forming a complex", and (3) Said complex B and said complex A are separated in a separation region of a capillary by further electric movement (migration).

(l) A Case when a Labeled Analogue and a CFS are Used.

(1) (a) A solution including a sample having an analyte, and not less than one kind of CFSs, and (b) a solution containing a labeled analogue are introduced and arranged into a capillary, as the above-described step (1) in the case (l) of "1-6. Specific methods for forming a complex", (2) Subsequently, said labeled analogue is electrophoretically contacted with CFS (namely, said labeled analogue is electrophoretically contacted with said CFS not involved in the formation of a complex (complex A) with said analyte in the said solution including a sample having an analyte, and not less than one kind of CFSs) to form the complex B between said labeled analogue and CFS, as the above-described step (2) in the case (l) of "1-6. Specific methods for forming a complex", and (3) Said complex B and said labeled analogue not involved in formation of said complex B are separated in a separation region of a capillary by further electric movement (migration).

(m) A Case when a Labeled Analogue and a Reaction Improvement CFS are Used.

(1) (a) A solution containing a sample having an analyte, and not less than one kind of reaction improvement CFSs, and (b) a solution containing a labeled analogue are introduced and arranged into a capillary, as the above-described step (1) in the case (m) of "1-6. Specific methods for forming a complex", (2) Subsequently, said labeled analogue is electrophoretically contacted with said reaction improvement CFS (namely, said labeled analogue is electrophoretically contacted with said reaction improvement CFS not involved in the formation of a complex (complex A) with said analyte in the said solution including a sample having an analyte, and not less than one kind of reaction improvement CFS) to form the complex B between said labeled analogue and reaction improvement CFS, as the above-described step (2) in the case (m) of "1-6. Specific methods for forming a complex", and (3) Said complex B and said labeled analogue not involved in formation of said complex are separated in a separation region of a capillary by further electric movement (migration).

(n) A Case when a Labeled Analogue, a CFS and a Reaction Improvement CFS are Used.

(1) (a) A solution containing a sample having an analyte and not less than one kind of a CFS (or not less than one kind of a reaction improvement CFS), (b) a solution containing a labeled analogue and (c) a solution containing not less than one kind of a reaction improvement CFS (or not less than one kind of a CFS) are introduced and arranged into a capillary, as the above-described step (1) in the case (n) of "1-6. Specific methods for forming a complex", (2) Subsequently, said analyte and labeled analogue are electrophoretically contacted with said CFS and reaction improvement CFS [namely, a comple between said analyte and CFS (or reaction improvement CFS) in said solution (a) is electrophoretically contacted with said reaction improvement CFS (or CFS) in said solution (c), and said labeled analogue is electrophoretically contacted with said CFS (or reaction improvement CFS) not involved in the formation of said complex with said analyte in said solution (a) and said reaction improvement CFS (or CFS) in said solution (c)], as the above-described step (2) in the case (n) of "1-6. Specific methods for forming a complex", and (3) Said complex B and said labeled analogue not involved in formation of said complex B are separated in a separation region of a capillary by further electric movement (migration).

(o) A Case when a Reaction Improvement Analogue and a Labeled CFS are Used.

(1) (a) A solution containing a sample having an analyte, and not less than one kind of labeled CFSs, and (b) a solution containing a reaction improvement analogue are introduced and arranged into a capillary, as the above-described step (1) in the case (o) of "1-6. Specific methods for forming a complex", (2) Subsequently, said reaction improvement analogue is electrophoretically contacted with labeled CFS (namely, said reaction improvement analogue is electrophoretically with said labeled CFS not involved in the formation of a complex (complex A) with said analyte in the said solution including a sample having an analyte, and not less than one kind of labeled CFSs) to form the complex B between said reaction improvement analogue and labeled CFS, as the above-described step (2) in the case (o) of "1-6. Specific methods for forming a complex", and (3) Said complex B and said complex A are separated in a separation region of a capillary by further electric movement (migration).

3. A Method for Measuring of the Present Invention

By measuring the amount of a complex between an analyte or an analogue thereof and a CFS, and the amount of a CFS not involved in formation of said complex or an analogue not involved in formation of said complex, which are separated by a method for separation of the present invention, by a method corresponding to property of, for example, a labeling substance in a complex, or a labeling substance in a CFS or analogue thereof not involved in formation of a complex, the amount of an analyte present in a sample can be determined simply, in high sensitivity and in a short time.

Therefore, a method for measuring of the present invention features in comprising:

(1) a step (a step of introduction) of arranging (a) a solution containing an analyte or an analogue thereof and (b) a solution containing not less than one kind of a substance formable the complex (the CFS) with said analyte or said analogue thereof, in a capillary, so that by applying a voltage to said capillary the complex between said analyte or said analogue thereof and the CFS are formed without mixing these solutions in advance;

(2) a step (a step of concentrating reaction) of contacting said analyte or said analogue thereof with the CFS while concentrating said analyte or said analogue thereof and/or at least one kind of the CFSs by applying a voltage to said capillary before uniformly mixing these solutions to form the complex between said analyte or said analogue thereof and the CFS;

(3) a step (a step of separation) of separating said complex and the CFS not involved in the formation of said complex or the analogue not involved in the formation of said complex by further electrical movement (migration); and (4) a step (a step of measurement) of measuring the amount of thus separated complex, or the amount of the CFS not involved in formation of said complex or the amount of the analogue not involved in formation of said complex, to determine the amount of an analyte based on the result.

In this connection, in the above description, embodiments, a specific example, a preferable example, and the like of an analyte, an analogue (a labeled analogue, a reaction improvement analogue, etc.), a solution containing an analyte or an analogue thereof, a sample including an analyte, a CFS (a labeled CFS, a reaction improvement CFS, a labeled reaction improvement CFS, etc.), solutions including these, a step of introduction [a step (1)], a step of a concentrating reaction [a step (2)], a step of separation [a step (3)] are as described above.

A method for measuring of the present invention is for measuring the amount of a complex between an analyte or an analogue thereof and a CFS, or the amount of a CFS not involved in formation of said complex or the amount of an analogue not involved in formation of said complex, which are separated by a step (3) of the present invention as described above, and for determining the amount of an analyte, based on the results, and in more specifically, (1) for measuring the amount of a complex between an analyte and a CFS, or the amount of a CFS not involved in formation of said complex, which are separated by a step (3) of the present invention, and for determining the amount of an analyte, based on the results; or (2) for measuring the amount of a complex between an analogue and a CFS, or the amount of an analogue not involved in formation of said complex, or the amount of a complex between an analyte and a CFS, which are separated, and for determining the amount of an analyte, based on the results.

A method for measuring of the present invention is applicable to any of a non-competitive method or a competitive method.

Namely, when a method for measuring of the present invention is carried out by a non-competitive method, for example, it may be carried out as follows:

(1) By a step (1) of the present invention, (a) A solution containing an analyte [for example, (i) a sample including an analyte, (ii) a solution including a sample having an analyte, and not less than one kind of CFSs] and (b) a solution containing not less than one kind of CFSs (a CFS, a labeled CFS, a reaction improvement CFS, a labeled reaction improvement CFS, combinations thereof) are arranged into a capillary, so that by applying a voltage to said capillary the complex between said analyte and the CFS [(analyte-CFS) complex, (analyte-labeled CFS) complex, (analyte-reaction improvement CFS) complex, (analyte-labeled reaction improvement CFS) complex, (CFS-analyte-reaction improvement CFS) complex, (labeled CFS-analyte-reaction improvement CFS) complex, (CFS-analyte-labeled reaction improvement CFS) complex, and combinations thereof, etc.] is formed, without mixing these solutions in advance;

(2) by a step (2) of the present invention, said analyte is contacted with said CFS while concentrating said analyte and/or at least one kind of the CFSs by applying a voltage to said capillary before uniformly mixing these solutions to form the complex between said analyte and the CFS;

(3) by a step (3) of the present invention, said complex and a CFS not involved in formation of said complex are separated by further electrical movement (migration); and (4) the amount of separated complex or the amount of a CFS not involved in formation of said complex is measured to determine the amount of an analyte in a sample based on the result.

In addition, when a method for measuring of the present invention is carried out by a competitive method, for example, it may be carried out as follows:

(1) By a step (1) of the present invention, (i) (a) a sample including an analyte (or a solution including a sample having an analyte, and not less than one kind of CFSs), (b) a solution containing a labeled analogue labeled by a labeling substance (or a solution including a labeled analogue and not less than one kind of CFSs), and (c) a solution containing not less than one kind of CFSs (a CFS, a reaction improvement CFS, combinations thereof), or (ii) (a) a solution containing a sample having an analyte, and a labeled analogue (or a solution including a sample having an analyte, a labeled analogue and not less than one kind of CFSs), and (b) a solution containing not less than one kind of CFSs (a CFS, a reaction improvement CFS, combinations thereof), or (iii) (a) a solution including a sample having an analyte, and not less than one kind of CFSs (a CFS, a reaction improvement CFS, combinations thereof), and (b) a solution containing a labeled analogue (or a solution including a labeled analogue and not less than one kind of CFSs), are arranged into a capillary, so that by applying a voltage to said capillary a complex B between said labeled analogue and CFS [(labeled analogue-CFS) complex, (labeled analogue-reaction improvement CFS) complex, (CFS-labeled analogue-reaction improvement CFS) complex, and combinations thereof, etc.] is formed, or a complex A between said analyte and CFS [(analyte-CFS) complex, (analyte-reaction improvement CFS) complex, (CFS-analyte-reaction improvement CFS) complex, and combinations thereof, etc.] and such Complex B are formed, without mixing these solutions in advance;

(2) by a step (2) of the present invention, (i) said labeled analogue is contacted with said CFS [namely, said labeled analogue is contacted with a CFS not involved in the formation of a complex (complex A) including said analyte] or (ii) said analyte and labeled analogue are contacted with said CFS (namely, said analyte is contacted with said CFS and said labeled analogue is contacted with said CFS) while concentrating at least one of said analyte, said labeled analogue and not less than one kind of CFSs before uniformly mixing these solutions, to form the complex B between said labeled analogue and CFS or to form the complex A between said analyte and CFS and the complex B;

(3) by a, step (3) of the present invention, said complex B, and a labeled analogue not involved in formation of said complex B are separated by further electrical movement (migration); and (4) the amount of separated complex B, or the amount of said labeled analogue not involved in formation of said complex B is measured to determine the amount of an analyte in a sample based on the result.

In addition, when a method for measuring of the present invention is carried out by a competitive method, for example, it may also be carried out as follows:

(1) By a step (1) of the present invention, (i) (a) a sample including an analyte (or a solution including a sample having an analyte, and not less than one kind of CFSs), (b) a solution containing a analogue bound with a reaction improvement substance (a reaction improvement analogue) (or a solution including a reaction improvement analogue and not less than one kind of CFSs), and (c) a solution containing not less than one kind of CFSs (a CFS, a labeled CFS, combinations thereof), or (ii) (a) a solution including a sample having an analyte, and a reaction improvement analogue (or a solution including a sample having an analyte, a reaction improvement analogue and not less than one kind of CFSs), and (b) a solution containing not less than one kind of CFSs (a CFS, a labeled CFS, combinations thereof), or (iii) (a) a solution including a sample having an analyte, and not less than one kind of CFSs (a CFS, a labeled CFS, combinations thereof), and (b) a solution containing a reaction improvement analogue (or a solution including a reaction improvement analogue and not less than one kind of CFSs), are arranged into a capillary, so that by applying a voltage to said capillary a complex B between said reaction improvement analogue and labeled CFS is formed, or a complex A between said analyte and labeled CFS and such Complex B are formed, without mixing these solutions in advance;

(2) by a step (2) of the present invention, (i) said reaction improvement analogue is contacted with said labeled CFS [namely, said reaction improvement analogue is contacted with a labeled CFS not involved in the formation of a complex (complex A) including said analyte] or (ii) said analyte and reaction improvement analogue are contacted with said labeled CFS (namely, said analyte is contacted with said labeled CFS and said reaction improvement analogue is contacted with said labeled CFS) while concentrating at least one of said analyte, said reaction improvement analogue and not less than one kind of labeled CFS before uniformly mixing these solutions, to form the complex B between said reaction improvement analogue and labeled CFS or to form the complex A between said analyte and labeled CFS and the complex B;

(3) by a step (3) of the present invention, said complex B and complex A are separated by further electrical movement (migration); and (4) the amount of separated complex B or the amount of separated complex A is measured to determine the amount of an analyte in a sample based on the result.

In this connection, an analogue (a labeled analogue or a reaction improvement analogue) is used by (i) co-presence with an analyte in a sample (namely, a sample including an analyte) as a solution including a labeled analogue or a reaction improvement analogue and an analyte (a solution containing an analyte and an analogue); or (2) without co-presence with an analyte in a sample (namely, a sample including an analyte) and separately from a solution containing an analyte, as a solution containing an analogue.

3-1. A Step of Measurement [a Step (4)]

In a step (4) of the present invention, the amount of a complex or the amount of a CFS not involved in formation of said complex or the amount of an analogue not involved in formation of said complex, which are separated, may be measured, for example, by a method corresponding to property of a labeling substance in said complex, or a labeling substance in a CFS not involved in formation of said complex or a labeling substance in an analogue not involved in formation of said complex, and based on measurement results of said labeling substance. Namely, in a non-competitive method, the amount of a complex between an analyte and a CFS, or the amount of a CFS not involved in formation of said complex, which are separated, may be determined, for example, by a method corresponding to property of a labeling substance in said complex, or labeling substance in CFS not involved in formation of said complex, and based on the result of measurement of said labeling substance. In a competitive method, the amount of a complex B or the amount of a labeled analogue not involved in formation of said complex B (or the amount of a complex B or the amount of a complex A), which are separated, may be determined, by a method corresponding to property of a labeling substance in said complex B, or a labeling substance in a labeled analogue not involved in formation of said complex B (or a labeling substance in a complex A), and based on the measurement result of said labeling substance.

Measurement of a labeling substance may be carried out in accordance with each specified method corresponding to a kind of a labeling substance. For example, when said property is enzyme activity, measurement of a labeling substance may be carried out in accordance with a common method such as EIA or a hybridization method [for example, a method described in "Enzyme immunoassay method, protein, nucleic acid, enzyme, separate vol., No. 31, Edited by T. Kitagawa, T. Nannbara, A. Tuji, 51 to 63, KYQRITSU SHUPPAN Co., Ltd., published on Sep. 10, 1987", etc.]; when said property is radioactivity, measurement of a labeling substance may be carried out by using suitably selected measuring instrument such as a liquid immersion type GM counter, a liquid scintillation counter, and a well-type scintillation counter, depending on kind and intensity of radiation ray emitted by said radio active substance in accordance with a common method such as RIA or a hybridization method, [for example, Medical Chemistry Experimental Course, vol. 8, Edited by U. Yamamura, $1^{st}$ Ed., published by Nakayama Bookstore in 1971; Biochemistry Experimental Course 2, A Tracer Experiment Method (part 2), A. Takemura, H, Honjo, 501 to 525, published by TOKYO KAGAKU DOJIN Co., Ltd. on Feb. 25, 1977]; when said property is fluorescence, measurement of a labeling substance may be carried out in accordance with a common method such as FIA or a hybridization method using measuring instrument such as fluorospectrometer or a confocal laser scanning microscope [a method described in, for example, "Illustration Explanation, Fluorescent antibody, A. Kawao, $1^{st}$ Ed, published by Softscience Co., Ltd., 1983"; "Medical Chemistry Experimental Course, vol. 2, Chemistry of nucleic acid III, M. Saneyoshi, 299 to 318, published by TOKYO KAGAKU DOJIN Co., Ltd. on Dec. 15, 1977"]; when said property is luminescence, measurement of a labeling substance may be carried out in accordance with a common method using measuring instrument such as a photon-counter [for example, a method described in "Enzyme immunoassay method, protein, nucleic acid, enzyme, separate vol., No. 31, Edited by T. Kitagawa, T. Nannbara, A. Tuji, 252 to 263, KYORITSU SHUPPAN Co., Ltd., published on, Sep. 10, 1987"]; further when said property is UV absorption, measurement of a labeling substance may be carried out in accordance with a common method using measuring instrument such as a spectrometer; when said property is color phenomenon, measurement of a labeling substance may be carried out in accordance with a common method using measuring instrument such as a spectrometer or a microscope; when said property is spin, measurement of a labeling substance may be carried out in accordance with a common method using electron spin resonance instrument [for example, a method described in "Enzyme immunoassay method, protein, nucleic acid, enzyme, separate vol., No. 31, Edited by T. Kitagawa, T. Nannbara, A. Tuji, 264 to 271, KYORITSU SHUPPAN Co., Ltd., published on Sep. 10, 1987", etc.].

In addition, determination of the amount of an analyte present in a sample, based on measured amount of a complex or amount of a CFS not involved in formation of said complex or amount of an analogue not involved in formation of said complex, namely the amount of a labeling substance in a complex or amount of a labeling substance in a CFS not involved in formation of said complex or a labeling substance in an analogue not involved in formation of said complex, may be carried out for example, as follows:

In a competitive method, determination of the amount of an analyte present in a sample based on the measured amount of a complex or the amount of a CFS not involved in formation of said complex, namely the amount of a labeling substance in a complex or the amount of a labeling substance in a CFS not involved in formation of said complex, obtained as above, can be carried out, for example, by preparing a calibration curve showing relation between the amount of an analyte and the amount of a labeling substance in a complex or the amount of a labeling substance in a CFS not involved in formation of said complex, obtained by measurement with a similar method using a sample containing a known concentration of an analyte, and by applying the amount of a labeling substance obtained by measurement of a sample containing an analyte to said calibration curve. In addition, in a non-competitive method, determination of the amount of an analyte present in a sample based on the amount of a complex B or the amount of a labeled analogue not involved in formation of said complex B (or the amount of a complex B or the amount of complex A), namely the amount of a labeling substance in a complex B or the amount of a labeling substance in a labeled analogue not involved in formation of said complex B (or the amount of a labeling substance in a complex A), obtained as above, can be carried out, for example, by preparing a calibration curve showing relation between the amount of an analyte, and the amount of a labeling substance in a complex B or the amount of a labeling substance in a labeled analogue not involved in formation of said complex B (or the amount of a labeling substance in a complex A), obtained by measurement with a similar method using a sample containing a known concentration of an analyte, and by applying the amount of a labeling substance obtained by measurement of a sample containing an analyte to said calibration curve.

In addition, by the addition of a known concentration of a detectable substance as an internal standard into a sample, and by comparing the amount of said substance added as internal standard, with the amount of a complex not involved in formation of said complex, or the amount of a CFS or the amount of an analogue not involved in formation of said complex [namely, the amount of a labeling substance in a complex or the amount of a labeling substance in a CFS not involved in formation of said complex, or the amount of a labeling substance in a complex B or the amount of a labeling substance in a labeled analogue not involved in formation of said complex B (or the amount of a labeling substance in a complex B or the amount of a labeling substance in a complex A)], the relative amount of an analyte in a sample may be calculated. In addition, such calculation can also be correct an error among electrophoresis equipment (device). Furthermore, by using the mobility of a peak of an internal standard it is possible to also correct the mobility of an objective peak.

Such detectable substances (internal standards) include, for example, peptide, protein, nucleic acid (DNA, RNA), an amino acid, sugar, a sugar chain, etc., labeled with the above described labeling substance; and a fluorescent substance, etc.

In addition, in the present invention, when an enzyme is used as a labeling substance, and the like, substrates or other coupling enzymes of said enzyme may be required to measure activity of said enzyme. In such a case, for example, these substrates or other coupling enzymes may be arranged in a capillary at the downstream side of a solution including a complex or a CFS not involved in formation of said complex or an analogue not involved in formation of said complex [namely, a complex between an analyte and a CFS or a CFS not involved in formation of said complex, or a complex B or a labeled analogue not involved in formation of said complex B (or a complex B or a complex A)], separated by a step (3) of the present invention, at least before carrying out a step (4) of the present invention. It is preferable that in a step (1) of the present invention a solution including these substrates or other coupling enzymes is arranged at further downstream side of the solution (zone) arranged at the most downstream side among a solution (zone) including an analyte or analogue thereof and a solution (zone) including not less than one kind of CFSs, and steps (1) to (4) of the present invention are carried out.

In addition, when an intercalator dye is used as a labeling substance, in a step (1) of the present invention said intercalator dye is not required to be introduced and arranged in a capillary with a solution containing an analyte or an analogue thereof, and a solution including not less than one kind of CFSs. And also, in a step (2) of the present invention said intercalator dye is not required to make contact with an analyte or an analogue thereof and a CFS. It is only necessary to carry out at least a step (3) of the present invention in the presence of said intercalator dye. In such a case, specifically, for example, said intercalator dye may be contained in an electrophoresis medium and/or buffer solution used in a step (3) of the present invention. Among others, in the present invention, it is preferable that a step (2) and a step (3) of the present invention are carried out in the presence of said intercalator dye. In this case, said intercalator dye may be contained in an electrophoresis medium and/or buffer solution used in a step (2) and in a step (3) of the present invention.

3-2. Use of a Charged Polymer

In the present invention, it is preferable that a step (2) is carried out in the presence of a charged polymer.

Namely, (i) by making contact of an analyte or an analogue thereof, and a CFS in the presence of a charged polymer to form a complex between said analyte or analogue thereof and CFS, or (ii) by making contact of an analyte, an analogue (a labeled analogue) and a CFS in the presence of a charged polymer to form a complex A between said analyte and CFS, and a complex B between said labeled analogue and CFS; or (iii) by making contact of an analyte, a reaction improvement analogue and a labeled CFS in the presence of a charged polymer to form a complex A between said analyte and labeled CFS and a complex B between said reaction improvement analogue and labeled CFS, effect of a co-present substance in a sample (particularly in a serum sample) having bad effect on analysis can be reduced. Specifically, for example, (i) by making contact of an analyte and CFS in the presence of a charged polymer, a complex between said analyte and CFS [(analyte-CFS) complex, (analyte-labeled CFS) complex, (analyte-reaction improvement CFS) complex, (analyte-labeled reaction improvement CFS) complex, (CFS-analyte-reaction improvement CFS) complex, (labeled CFS-analyte-reaction improvement CFS) complex, (CFS-analyte-labeled reaction improvement CFS) complex, and combinations thereof, etc.] is formed; or (ii) by making contact of an analyte, a labeled analogue and a CFS in the presence of a charged polymer (namely, by making contact of said analyte and CFS, and said labeling analogue and CFS), a complex A between said analyte and said CFS [(analyte-CFS) complex, (analyte-reaction improvement CFS) complex, (CFS-analyte-reaction improvement CFS) complex, and combinations thereof, etc.] and a complex B between said labeled analogue and CFS [(labeled analogue-CFS) complex, (labeled analogue-reaction improvement CFS) complex, (CFS-labeled analogue-reaction improvement CFS) complex, and combinations thereof, etc.] are formed; or (iii) by making contact of an analyte, a reaction improvement analogue and a labeled CFS (namely, by making contact of said analyte and labeled CFS, and said reaction improvement analogue and labeled CFS) in the presence of a charged polymer, a complex A between said analyte and said labeled CFS and a complex B between said reaction improvement analogue and said labeled CFS are formed.

As a charged polymer used in the present invention, one having the opposite charge (plus or minus) from that of a co-present substance in a sample is used. In addition, a charged polymer having the same charge as that of a CFS used is preferable.

As such a charged polymer, polyanionic polymers and polycationic polymers are included.

Polyanionic polymers include, polysaccharides such as heparin, heparin sulfate, chondroitin sulfate, dextran sulfate, polytungstic acid, tungstophosphoric acid, hyaluronic acid, dermatan sulfate and polyanethole sulfate, etc.; polynucleotides such as DNA (plasmid DNA, calf thymus DNA, salmon sperm DNA, DNA bound with cellulose and synthetic DNA, etc.), and RNA, etc.; polypeptides such as polyamino acids (polyaspartic acid, polyglutamic acid, etc.), a synthetic polypeptide, etc.; synthetic polymer compounds such as poly-dIdC, polyvinyl sulfate, polyacrylic acid, etc.; ceramics such as glass particle, colloidal glass, glass milk, etc.; and complexes thereof; and the like.

In addition, polycationic polymers include, polysaccharides such as chitosan, derivatives thereof, etc.; polypeptides such as polylysine, polyhistidine, polyarginine, protamine, histone, ornithine, etc.; synthetic polymer compounds such as polyallyl amine, polyethylene imine, polyvinyl amine, etc.; polyamines such as spermine, spermidine, etc.; cationic lipid; ceramics; complexes thereof; and the like.

Among them, an anionic polysaccharide is preferable, and heparin sulfate is particularly preferable.

The above-described charged polymers may be used alone or in suitable combination with two or more kinds.

A method for making the above described charged polymers present in carrying out a step (2) is not especially limited as long as formation of a complex can finally be carried out in the presence of a charged polymer.

Such a method includes, for example, a method for making a charged polymer co-present in an electrophoresis medium to be filled in a capillary as described above; a method for making a charged polymer co-present in a solution containing an analyte or an analogue thereof, and/or in a solution containing CFS; and the like.

Among these, the charged polymer is co-present preferably in a solution (zone) other than the solution (zone) containing an analyte, more preferably in at least one solution (zone) arranged adjacently upstream side or downstream side of the solution (zone) containing an analyte.

Use amount of the above-described charged polymer is not simply be described due to dependency on the kind of the charged polymer used, however, for example, concentration in an electrophoresis medium to be filled in a channel is, as lower limit, usually not lower than 0.01% (w/v), preferably not lower than 0.05% (w/v), and more preferably not lower than 0.5% (w/v), and as upper limit, usually not higher than 50% (w/v), preferably not higher than 10% (w/v) and further preferably not higher than 5% (w/v), and among others about 1% (w/v) is particularly preferable. In addition, concentration in a solution containing an analyte or an analogue thereof or in a solution containing a CFS is, as lower limit, usually not lower than 0.001% (w/v), preferably not lower than 0.01% (w/v), more preferably not lower than 0.02% (w/v), and further preferably not lower than 0.025% (w/v), and as upper limit, usually not higher than 10% (w/v), preferably not higher than 5% (w/v), more preferably not higher than 1% (w/v) and further preferably not higher than 0.05% (w/v).

3-3. A Specific Methods for Measurement

Modes for carrying out the methods for measurement of the present invention are specifically shown below.

(1) A Non-Competitive Method

A method for measurement for the case of a non-competitive method is as follows:

(a) A Case when a CFS not Bound with a Labeling Substance and a Reaction Improvement Substance are Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs] and (b) a solution containing not less than one kind of CFSs are introduced and arranged into a capillary, as the above-described step (1) in the case (a) of "1-6. Specific methods for forming a complex", (2) Subsequently, said analyte is electrophoretically contacted with said CFS to form the complex between said analyte and the CFS, as the above-described step (2) in the case (a) of "1-6. Specific methods for forming a complex", (3) Said complex and said CFS not involved in formation of said complex are separated by further electric movement (migration), as the above-described step (3) in the case (a) of "2-2. specific methods for separation", and (4) The amount of a CFS contained in the separated complex or the amount of a CFS not involved in formation of said complex is measured by a method corresponding to property (kind) of a CFS, and the amount of an analyte in a sample is calculated by applying the measurement result (measurement value) to a calibration curve showing relation between the amount of an analyte and the amount of a CFS, obtained by a similar method using a sample containing a known concentration of an analyte.

[Method B]:

A known concentration of a detectable substance as an internal standard is added to at least one of a solution containing an analyte and a solution containing CFS in the above-described step (1) of [method A], and the above-described steps (1) to (3) are carried out using that solution containing the internal standard. The amount of a CFS contained in the separated complex or the amount of a CFS not involved in formation of said complex is measured by a method corresponding to property (kind) of a CFS, and the amount of an analyte in a sample is calculated by comparing the measurement result (measurement value) with the amount of said substance added as internal standard.

(b) A Case when a Labeled CFS is Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs] and (b) a solution containing not less than one kind of labeled CFSs are introduced and arranged into a capillary, as the above-described step (1) in the case (b) of "1-6. Specific methods for forming a complex", (2) Subsequently, said analyte is electrophoretically contacted with said labeled CFS to form the complex between said analyte and labeled CFS, as the above-described step (2) in the case (b) of "1-6. Specific methods for forming a complex", (3) Said complex and said labeled CFS not involved in formation of said complex are separated by further electric movement (migration) by further electric movement (migration), as the above-described step (3) in the case (b) of "2-2. specific methods for separation", and (4) The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one of a solution containing an analyte and a solution containing a labeled CFS in the above-described step (1) of [method A], and the above-described steps (1) to (3) are carried out using that solution containing the internal standard. The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by comparing the measurement result (measurement value) with the amount of said substance added as internal standard.

(c) A Case when a Reaction Improvement CFS is Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs] and (b) a solution containing not less than one kind of reaction improvement CFSs are introduced and arranged into a capillary, as the above-described step (1) in the case (c) of "1-6. Specific methods for forming a complex", (2) Subsequently, said analyte is electrophoretically contacted with said reaction improvement CFS to form the complex between said analyte and reaction improvement CFS, as the above-described step (2) in the case (c) of "1-6. Specific methods for forming a complex", (3) Said complex and said reaction improvement CFS not involved in formation of said complex are by further electric movement (migration), as the above-described step (3) in the case (c) of "2-2. specific methods for separation", and (4) The amount of a reaction improvement CFS contained in the separated complex or the amount of a reaction improvement CFS not involved in formation of said complex is measured by a method corresponding to property (kind) of a reaction improvement CFS, and the amount of an analyte in a sample is calculated by applying the measurement result (measurement value) to a calibration curve showing relation between the amount of an analyte and the amount of a reaction improvement CFS, obtained by a similar method using a sample containing a known concentration of an analyte.

[Method B]:

A known concentration of a detectable substance as an internal standard is added to at least one of a solution containing an analyte and a solution containing a reaction improvement CFS in the above-described step (1) of [method A], and the above-described steps (1) to (3) are carried out using that solution containing the internal standard. The amount of a reaction improvement CFS contained in the separated complex or the amount of a reaction improvement CFS not involved in formation of said complex is measured by a method corresponding to property (kind) of a reaction improvement CFS, and the amount of an analyte in a sample is calculated by comparing the measurement result (measurement value) with the amount of said substance added as internal standard.

(d) A Case when a Labeled Reaction Improvement CFS is Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs] and (b) a solution containing not less than one kind of labeled reaction improvement CFSs are introduced and arranged into a capillary, as the above-described step (1) in the case (d) of "1-6. Specific methods for forming a complex", (2) Subsequently, said analyte is electrophoretically contacted said labeled reaction improvement CFS to form the complex between said analyte and labeled reaction improvement CFS, as the above-described step (2) in the case (d) of "1-6. Specific methods for forming a complex", (3) Said complex and said labeled reaction improvement CFS not involved in formation of said complex are separated by further electric movement (migration), as the above-described step (3) in the case (d) of "2-2. specific methods for separation", and (4) The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one of a solution containing an analyte and a solution containing a labeled reaction improvement CFS in the above-described step (1) of [method A], and the above-described steps (1) to (3) are carried out using that solution containing the internal standard. The amount of a labeling substance contained in the separated complex or the amount of a labeling contained substance in a labeled reaction improvement CFS not involved in formation of said complex is measured by a method corresponding to property (kind) of a labeling substance, and the amount of an analyte in a sample is calculated by comparing the measurement result (measurement value) with the amount of said substance added as internal standard.

(e) A Case when a CFS not Bound with a Labeling Substance and a Reaction Improvement Substance, and a Reaction Improvement CFS are Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a reaction improvement CFS are introduced and arranged into a capillary, as the above-described step (1) in the case (e) of "1-6. Specific methods for forming a complex", (2) Subsequently, said analyte is electrophoretically contacted with said CFS and reaction improvement CFS to form the complex between said analyte, CFS and reaction improvement CFS, as the above-described step (2) in the case (e) of "1-6. Specific methods for forming a complex", (3) Said complex and said CFS not involved in formation of said complex and optionally a reaction improvement CFS not involved in formation of said complex are separated by further electric movement (migration), as the above-described step (3) in the case (e) of "2-2. specific methods for separation", and (4) The amount of a CFS contained in the separated complex or the amount of a reaction improvement CFS contained in the separated complex, or the amount of a CFS not involved in formation of said complex or the amount of a reaction improvement CFS not involved in formation of said complex is measured by a method corresponding to property (kind) of a CFS or a reaction improvement CFS, and the amount of an analyte in a sample is calculated by applying the measurement result (measurement value) to a calibration curve showing relation between the amount of an analyte, and the amount of a CFS or the amount of a reaction improvement CFS, obtained by a similar method using a sample containing a known concentration of an analyte.

[Method B]:

A known concentration of a detectable substance as an internal standard is added to at least one selected from a solution containing an analyte, a solution containing a CFS and a solution containing a reaction improvement CFS in the above-described step (1) of [method A], and the above-described steps (1) to (3) are carried out using that solution containing the internal standard. The amount of a CFS contained in the separated complex or the amount of a reaction improvement CFS contained in the separated complex, or the amount of a CFS not involved in formation of said complex or the amount of a reaction improvement CFS not involved in formation of said complex is measured by a method corresponding to property (kind) of a CFS or a reaction improvement CFS, and the amount of an analyte in a sample is calculated by comparing the measurement result (measurement value) with the amount of said substance added as internal standard.

(f) A Case when a Labeled CFS and a Reaction Improvement CFS are Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs], (b) a solution containing not less than one kind of a labeled CFS and (c) a solution containing not less than one kind of a reaction improvement CFS are introduced and arranged into a capillary, as the above-described step (1) in the case (f) of "1-6. Specific methods for forming a complex", (2) Subsequently, said analyte is electrophoretically contacted with said labeled CFS and reaction improvement CFS to form the complex between said analyte, labeled CFS and reaction improvement CFS, as the above-described step (2) in the case (f) of "1-6. Specific methods for forming a complex", and (3) Said complex and said labeled CFS not involved in formation of said complex and optionally a reaction improvement CFS not involved in formation of said complex are separated by further electric movement (migration), as the above-described step (3) in the case (f) of "2-2. specific methods for separation", and (4) The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one selected from a solution containing an analyte, a solution containing a labeled CFS and a solution containing a reaction improvement CFS in the above-described step (1) of [method A], and the above-described steps (1) to (3) are carried out using that solution containing the internal standard. The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by comparing the measurement result (measurement value) with the amount of said substance added as internal standard.

(g) A Case when a CFS not Bound with a Labeling Substance and a Reaction Improvement Substance, and a Labeled Reaction Improvement CFS are Used.

In this case, for example, it may be carried out as the following [method A] or [method B].

[Method A]:

(1) (a) A solution containing an analyte [for example, (i) a sample including an analyte, (ii) a solution including a sample having an analyte, and not less than one kind of CFSs], (b) a solution containing not less than one kind of a CFS and (c) a solution containing not less than one kind of a labeled reaction improvement CFS are introduced and arranged into a capillary, as the above-described step (1) in the case (g) of "1-6. Specific methods for forming a complex", (2) Subsequently, said analyte is electrophoretically contacted with said CFS and labeled reaction improvement CFS to form the complex between said analyte, CFS and labeled reaction improvement CFS, as the above-described step (2) in the case (g) of "1-6. Specific methods for forming a complex", (3) Said complex and said labeled reaction improvement CFS not involved in formation of said complex and optionally a CFS not involved in formation of said complex are separated by further electric movement (migration), as the above-described step (3) in the case (g) of "2-2. specific methods for separation", and (4) The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one selected from a solution containing an analyte, a solution containing a CFS and a solution containing a labeled reaction improvement CFS in the above-described step (1) of [method A], and the above-described steps (1) to (3) are carried out using that solution containing the internal standard. The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by comparing the measurement result (measurement value) with the amount of said substance added as internal standard.

(2) A Competitive Method

A method for measurement for the case of a competitive method is as follows:

(h) A Case when a Labeled Analogue and a CFS are Used.

In this case, for example, it may be carried out as the following [method A] or [method B].

[Method A]:

(1) (a) A solution containing a sample having an analyte and a labeled analogue (or a solution including a sample having an analyte, a labeled analogue and not less than one kind of CFSs) and (b) a solution containing not less than one kind of CFSs are introduced and arranged into a capillary, as the above-described step (1) in the case (h) of "1-6. Specific methods for forming a complex", (2) Subsequently, said analyte and labeled analogue are electrophoretically contacted with said CFS (namely, said analyte is electrophoretically contacted with said CFS, and said labeled analogue electrophoretically contacted with said CFS) to form the complex A between said analyte and CFS and a complex B between said labeled analogue and CFS, as the above-described step (2) in the case (h) of "1-6. Specific methods for forming a complex", (3) Said complex B and said labeled analogue not involved in formation of said complex B are separated by further electric movement (migration), as the above-described step (3) in the case (h) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and a labeled analogue (or a solution including a sample having an analyte, a labeled analogue and not less than one kind of CFSs) or a solution containing a CFS in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(i) A Case when a Labeled Analogue and a Reaction Improvement CFS are Used.

In this case, for example, it may be carried out as the following [method A] or [method B].

[Method A]:

(1) (a) A solution including a sample having an analyte and a labeled analogue (or a solution including a sample having an analyte, a labeled analogue and not less than one kind of CFSs) and (b) a solution containing not less than one kind of reaction improvement CFSs are introduced and arranged into a capillary, as the above-described step (1) in the case (i) of "1-6. Specific methods for forming a complex", (2) Subsequently, said analyte and labeled analogue are electrophoretically contacted with said reaction improvement CFS (namely, said analyte is electrophoretically contacted with said reaction improvement CFS, and said labeled analogue is electrophoretically contacted with said reaction improvement CFS) to form the complex A between said analyte and reaction improvement CFS and a complex B between said labeled analogue and reaction improvement CFS, as the above-described step (2) in the case (i) of "1-6. Specific methods for forming a complex"

(3) Said complex B and said labeled analogue not involved in formation of said complex B are separated by further electric movement (migration), as the above-described step (3) in the case (i) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and a labeled analogue (or a solution including a sample having an analyte, a labeled analogue and not less than one kind of CFSs) or a solution containing a reaction improvement CFS in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(j) A Case when a Labeled Analogue, a CFS and a Reaction Improvement CFS are Used.

In this case, for example, it may be carried out as the following [method A] or [method B].

[Method A]:

(1) (a) A solution containing a sample having an analyte and a labeled analogue (or a solution including a sample having an analyte, a labeled analogue and not less than one kind of CFSs), (b) a solution including not less than one kind of a CFS and (c) a solution including not less than one kind of a reaction improvement CFS are introduced and arranged into a capillary, as the above-described step (1) in the case (j) of "1-6. Specific methods for forming a complex", (2) Subsequently, said analyte and labeled analogue are electrophoretically contacted with said CFS and reaction improvement CFS (namely, said analyte is electrophoretically contacted with said CFS and reaction improvement CFS, and said labeled analogue is electrophoretically contacted with said CFS and reaction improvement CFS) to form the complex A between said analyte, CFS and reaction improvement CFS and a complex B between said labeled analogue, CFS and reaction improvement CFS, as the above-described step (2) in the case (j) of "1-6. Specific methods for forming a complex", (3) Said complex B and said labeled analogue not involved in formation of said complex B are separated by further electric movement (migration), as the above-described step (3) in the case (j) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one selected from a solution containing a sample having an analyte and a labeled analogue (or a solution including a sample having an analyte, a labeled analogue and not less than one kind of CFSs), a solution containing a CFS and a solution containing a reaction improvement CFS in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(k) A Case when a Reaction Improvement Analogue and a Labeled CFS are Used.

In this case, for example, it may be carried out as the following [method A] or [method B].

[Method A]:

(1) (a) A solution containing sample having an analyte and reaction improvement analogue (or a solution including a sample having an analyte, a reaction improvement analogue and not less than one kind of CFSs) and (b) a solution including not less than one kind of labeled CFSs are introduced and arranged into a capillary, as the above-described step (1) in the case (k) of "1-6. Specific methods for forming a complex", (2) Subsequently, said analyte and reaction improvement analogue are electrophoretically contacted with said labeled CFS (namely, said analyte is electrophoretically contacted said labeled CFS, and said reaction improvement analogue is electrophoretically contacted with said labeled CFS) to form the complex A between said analyte and labeled CFS and the complex B between said reaction improvement analogue and labeled CFS, as the above-described step (2) in the case (k) of "1-6. Specific methods for forming a complex", (3) Said complex B and said complex A are separated by further electric movement (migration), as the above-described step (3) in the case (k) of "2-2. specific methods for separation", and (4) The amount of a labeling substance contained in the separated complex B or the amount of a labeling substance contained in the separated complex A is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and a reaction improvement analogue (or a solution including a sample having an analyte, a reaction improvement analogue and not less than one kind of CFSs) or a solution containing a labeled CFS in the above-described step (1) of [method A], and the above-described steps (1) to (3) are carried out using that solution containing the internal standard. The amount of a labeling substance contained in the separated complex B or the amount of a labeling substance contained in said the separated complex A is measured by a method corresponding to property (kind) of a labeling substance, and the amount of an analyte in a sample is calculated by comparing the measurement result (measurement value) with the amount of said substance added as internal standard.

(l) A Case when a Labeled Analogue and a CFS are Used.

In this case, for example, it may be carried out as the following [method A] or [method B].

[Method A]:

(1) (a) A solution including a sample having an analyte, and not less than one kind of CFSs, and (b) a solution containing a labeled analogue are introduced and arranged into a capillary, as the above-described step (1) in the case (1) of "1-6. Specific methods for forming a complex", (2) Subsequently, said labeled analogue is electrophoretically contacted with CFS (namely, said labeled analogue is electrophoretically contacted with said CFS not involved in the formation of a complex (complex A) with said analyte in the said solution including a sample having an analyte, and not less than one kind of CFSs) to form the complex B between said labeled analogue and CFS, as the above-described step (2) in the case (1) of "1-6. Specific methods for forming a complex", (3) Said complex B and said labeled analogue not involved in formation of said complex B are separated by further electric movement (migration), as the above-described step (3) in the case (1) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and not less than one kind of CFSs or a solution containing a labeled analogue in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(m) A Case when a Labeled Analogue and a Reaction Improvement CFS are Used.

In this case, for example, it may be carried out as the following [method A] or [method B].

[Method A]:

(1) (a) A solution containing a sample having an analyte, and not less than one kind of reaction improvement CFSs, and (b) a solution containing a labeled analogue are introduced and arranged into a capillary, as the above-described step (1) in the case (m) of "1-6. Specific methods for forming a complex", (2) Subsequently, said labeled analogue is electrophoretically contacted with said reaction improvement CFS (namely, said labeled analogue is electrophoretically contacted with said reaction improvement CFS not involved in the formation of a complex (complex A) with said analyte in the said solution including a sample having an analyte, and not less than one kind of reaction improvement CFS) to form the complex B between said labeled analogue and reaction improvement CFS, as the above-described step (2) in the case (m) of "1-6. Specific methods for forming a complex", (3) Said complex B and said labeled analogue not involved in formation of said complex are separated by further electric movement (migration), as the above-described step (3) in the case (m) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and not less than one kind of reaction improvement CFSs or a solution containing a labeled analogue in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(n) A Case when a Labeled Analogue, a CFS and a Reaction Improvement CFS are Used.

In this case, for example, it may be carried out as the following [method A] or [method B].

[Method A]:

(1) (a) A solution containing a sample having an analyte and not less than one kind of a CFS (or not less than one kind of a reaction improvement CFS), (b) a solution containing a labeled analogue and (c) a solution containing not less than one kind of a reaction improvement CFS (or not less than one kind of a CFS) are introduced and arranged into a capillary, as the above-described step (1) in the case (n) of "1-6. Specific methods for forming a complex", (2) Subsequently, said analyte and labeled analogue are electrophoretically contacted with said CFS and reaction improvement CFS [namely, a comple between said analyte and CFS (or reaction improvement CFS) in said solution (a) is electrophoretically contacted with said reaction improvement CFS (or CFS) in said solution (c), and said labeled analogue is electrophoretically contacted with said CFS (or reaction improvement CFS) not involved in the formation of said complex with said analyte in said solution (a) and said reaction improvement CFS (or CFS) in said solution (c)], as the above-described step (2) in the case (n) of "1-6. Specific methods for forming a complex", (3) Said complex B and said labeled analogue not involved in formation of said complex B are separated by further electric movement (migration), as the above-described step (3) in the case (n) of "2-2. specific methods for separation", and (4) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to at least one selected from a solution containing a sample having an analyte and not less than one kind of a CFS (or not less than one kind of a reaction improvement CFS), a solution containing a labeled analogue and a solution containing not less than one kind of a reaction improvement CFS (or not less than one kind of a CFS) in the above-described step (1) of [method A], and the above-described steps (1) to (3) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard.

(o) A Case when a Reaction Improvement Analogue and a Labeled CFS are Used.

In this case, for example, it may be carried out as the following [method A] or [method B].

[Method A]:

(1) (a) A solution containing a sample having an analyte, and not less than one kind of labeled CFSs, and (b) a solution containing a reaction improvement analogue are introduced and arranged into a capillary, as the above-described step (1) in the case (o) of "1-6. Specific methods for forming a complex", (2) Subsequently, said reaction improvement analogue is electrophoretically contacted with labeled CFS (namely, said reaction improvement analogue is electrophoretically with said labeled CFS not involved in the formation of a complex (complex A) with said analyte in the said solution including a sample having an analyte, and not less than one kind of labeled CFSs) to form the complex B between said reaction improvement analogue and labeled CFS, as the above-described step (2) in the case (o) of "1-6. Specific methods for forming a complex", (3) Said complex B and said complex A are separated by further electric movement (migration), as the above-described step (3) in the case (o) of "2-2. specific methods for separation", and (4) The amount of a labeling substance contained in the separated complex B or the amount of a labeling substance contained in the separated complex A is measured by a method corresponding to property (kind) of a labeling substance, and the amount of an analyte in a sample is calculated by applying the measurement result (measurement value) to a calibration curve showing relation between the amount of an analyte and the amount of a labeling substance, obtained by a similar method using a sample containing a known concentration of an analyte.

[Method B]:

A known concentration of a detectable substance as an internal standard is added to a solution containing a sample having an analyte and not less than one kind of a labeled CFS or a solution containing a reaction improvement analogue in the above-described step (1) of [method A], and the above-described steps (1) to (3) are carried out using that solution containing the internal standard. The amount of a labeling substance contained in the separated complex B or the amount of a labeling substance contained in said the separated complex A is measured by a method corresponding to property (kind) of a labeling substance, and the amount of an analyte in a sample is calculated by comparing the measurement result (measurement value) with the amount of said substance added as internal standard.

A method for measurement of the present invention may be carried out in accordance with the above-described known methods themselves except by using a method for separation of the present invention, and reagents to be used may also be selected, as appropriate, in accordance with known methods themselves.

4. A Kit of the Present Invention

A kit of the present invention is one to be used for carrying out the above-described method for forming a complex, method for separation and method for measuring of the present invention.

As such a kit, the following items should be included:

(1) At least (i) the above-described CFS, (ii) if necessary an analogue, and (iii) an instruction book to be used in the above-described method for forming a complex, method for separation and method for measuring of the present invention; or (2) (i) electrophoresis device (or microfluidic device) equipped with a capillary (channel) having at least a part enabling to carry out the above-described step (1) of the present invention and a part enabling to carry out the above-described step (2) of the present invention, preferably a capillary (channel) having a part enabling to carry out the above-described step (1), a part enabling to carry out the above-described step (2) and further a part enabling to carry out the above-described step (3) of the present invention, (ii) a CFS, (iii) if necessary an analogue, and (iv) an instruction book to be used in the above-described method for forming a complex, method for separation and method for measuring of the present invention.

In this connection, said "instruction book" means a handling manual (instruction manual) of said kit, attached documents (covering letter) or a pamphlet (leaflet), and the like, wherein features, principle, operation procedure, and the like, of a method of the present invention are substantially described by writing or drawings, and the like.

Preferable embodiments and specific examples of these composition elements are as described above.

Furthermore, a kit of the present invention may also contain reagents other than the above. Such reagents include, for example, a buffer solution for electrophoresis separation, a reagent diluent, internal standard, a calibrator (a standard solution), control, reagents (enzyme substrate, coupling enzymes, and the like) for measurement of labeling substances (for example, enzyme, dyes, luminescent substances, fluorescent substances, and the like), reagents for focusing a detector, and the like, but not limited thereto.

The present invention is explained in more detail below by referring to Examples and Comparative Examples, however, the present invention should not be limited thereby.

EXAMPLES

Example 1

An Analyte (an Antigen)

α-fetoprotein (AFP) (manufactured by Wako Pure Chemical Industries, Ltd.)

[A Reaction Improvement CFS (a DNA Labeled Antibody)

According to the procedure shown in FIG. 1, anti-AFP antibody Fab' fragment bound with DNA was prepared.

Namely, a 250 bp DNA fragment introduced with an $NH_2$ group at the 5' terminal was purified first by a common method. Subsequently, the $NH_2$ group introduced to the DNA fragment, and a succinimidyl group of a sulfosuccinimidyl 4-(p-maleimidophenyl)butyrate (Sulfo-SMPB) linker (a linker having a succinimidyl group and a maleimido group: manufactured by Pierce Co.) were subjected to a reaction by a common method. Then, by gel filtration treatment, unreacted linkers were removed to give a 250 bp DNA fragment bound with a linker. The resultant 250 bp DNA fragment bound with a linker, and an anti-AFP antibody WA1 Fab' fragment, prepared in advance using an anti-AFP antibody WA1 (manufactured by Wako Pure Chemical Industries, Ltd.) in accordance with a common method, were subjected to a reaction. The resultant reaction products were each purified using a DEAE column to prepare an anti-AFP antibody WA1 Fab' fragment bound with a 250 bp DNA fragment (a 250 bp DNA labeled antibody)

[A Labeled CFS (a Fluorescence Labeled Antibody)]

An anti-AFP antibody WA2 (manufactured by Wako Pure Chemical Industries, Ltd.) which recognizes an epitope of AFP different from a WA1 antibody, was treated by a common method to give an anti-AFP antibody WA2 Fab' fragment. A fluorescent substance Alexa647 (manufactured by Molecular Probes Inc.) was introduced to an amino group of said fragment by a common method to prepare an Alexa647 labeled anti-AFP antibody WA2 Fab' fragment (a fluorescence labeled antibody).

[A Capillary Chip]

A capillary chip having a layout shown in FIG. 2 was produced according to a method described in "Technology and application of microchemistry chip", T. Kitamori et al., published in 2004 (Maruzen Co., Ltd.) as follows:

Namely, a photo resist film was formed on Si film which was formed on a quartz substrate. This photo resist was exposed using a mask having a capillary design (layout) shown in FIG. 2 and developed. Si at the part, where a photo resist was removed by development, was removed by sputtering, and then wet etching was carried out using a solution of hydrogen fluoride to produce a capillary channel groove (capillary) at the quartz substrate. After removing a photo resist and a Si film remained on the quartz substrate, said quartz substrate and a cover plate having a hole for a fluid reservoir were adhered together by an HF bonding technique to produce a capillary chip.

In this connection, in FIG. 2, L1 and L2 show a well for introducing a leading buffer, S shows a well for introducing an electrophoresis sample, R1 shows a well for introducing a reagent solution (a solution containing a 250 bp DNA labeled antibody), and W1 and W2 show represent a well for drain, respectively.

[Electrophoresis]
(1) A Electrophoresis Sample
Into a 0.5 mL tube, 1 µL of AFP having predetermined concentration, 1 µL of 2 µM a fluorescence labeled antibody and 8 µL of a leading buffer containing 50 mM Cl⁻ ion were mixed to prepare 10 µL of a reaction solution. The reaction solution was stood still on ice to be subjected to an antigen-antibody reaction for about 30 minutes to form a [fluorescence labeled antibody-AFP] immune complex. In this connection, the final concentration of AFP was 0 pM, 25 pm, 50 pM or 100 pM, and the final concentration of the fluorescence labeled antibody was 200 nM.

The obtained reaction solution containing the immune complex was used as an electrophoresis sample.

(2) A Reagent Solution (a Solution Containing a 250 bp DNA Labeled Antibody)
A trailing buffer (containing 75 mM of HEPES) containing 20 nM of a 250 bp DNA labeled antibody was used as a reagent solution.

(3) Procedure of Electrophoresis
a) Introduction of an Electrophoresis Sample and a Reagent Solution
Into an S well (a well for introducing an electrophoresis sample) shown in FIG. 1, 10 µL of an electrophoresis sample (a solution containing a [fluorescence labeled antibody-AFP] immune complex) was delivered by drops, 10 µL of a reagent solution (a solution containing a DNA labeled antibody) was delivered by drops into an R1 well (a well for introducing a reagent solution), and 10 µL of a leading buffer was delivered by drops into an L1 and L2 wells, respectively, and by application of a pressure of −5 psi for 100 seconds between W1 (a well for drain) and W2 (a well for drain) an electrophoresis sample, a reagent solution and a leading buffer were introduced into the channel. Arrangement relation of an electrophoresis sample and a reagent solution in a capillary was schematically shown in FIG. 3. In this connection, in FIG. 3, a shaded area shows an arrangement area of an electrophoresis sample and a dotted area shows an arrangement area of a reagent solution, respectively.

b) Concentration and Reaction
By applying a voltage of 312 V, 625 V or 2500 V between an R1 well and an L1 well, a 250 bp DNA labeled antibody in the reagent solution contacted with a [fluorescence labeled antibody-AFP] immune complex in the electrophoresis sample, while concentrating a 250 bp DNA labeled antibody in a reagent solution, to form a [fluorescence labeled antibody-AFP-250 bp DNA labeled antibody] immune complex was formed while making concentrated a 250 bp DNA labeled antibody in a reagent solution at 10° C.

In this connection, reaction time was about 200 seconds in application of a voltage of 312 V, about 100 seconds in application of a voltage of 625 V, and about 25 seconds in application of a voltage of 2500 V.

c) Separation and Detection
When a [fluorescence labeled antibody-AFP-250 bp DNA labeled antibody] immune complex overtook through a crossing part of an L2 channel and a main channel, 2800 V was applied onto the L2 well and 300 V was applied onto an L1 well, for 100 seconds to separate and detect said immune complex.

In this connection, the detection was carried out by serial measurement of fluorescent intensity by laser excitation of 635 nm at a capillary part at 2 cm from the crossing part of the L2 channel, using a, fluorescent microscope (BX-50, manufactured from KS Olympus Co., Ltd.)

[Results]
FIG. 4 shows relation (linearity) between AFP concentration and peak area, and FIG. 5 shows each of electrophoresis chromatogram when an electrophoresis sample of an AFP concentration of 0 pM and 100 pM was used. In this connection, in FIG. 4, vertical axis shows peak area and horizontal axis shows AFP concentration, respectively. In addition, in FIG. 5, a solid line (-) shows the case when an electrophoresis sample of an AFP concentration of 100 pM was used and a dotted line (• • •) shows the case when an electrophoresis sample of an AFP concentration of 0 pM was used, respectively.

From FIGS. 4 and 5, it is found that a peak of a [fluorescence labeled antibody-AFP-250 bp DNA labeled antibody] immune complex is observed and peak area thereof is proportional to AFP concentration. Namely, it can be understood that an immune complex is electrophoretically formed in a capillary (channel) and there is no necessity to react and form the immune complex in advance outside a capillary (channel).

In addition, Table 2 shows the relation between an applied voltage and an AFP reaction rate in concentration and reaction. As Comparative Example, the AFP reaction rate obtained when these solutions are reacted for 120 seconds by a conventional method introducing a plurality of solutions in a mixing capillary (channel) simultaneously to be subjected to mixing and reaction (JP-A-2005-31070, and the like), was also shown.

In this connection, AFP reaction rate is a relative value obtained when an AFP signal (peak area) was detected similarly as above after reacting a fluorescence labeled antibody, AFP and a 250 bp DNA labeled antibody at 10° C. for 30 minutes in advance outside a capillary to obtain 10 µL of a reaction solution containing 200 nM of a fluorescence labeled antibody, 100 pM of AFP and 20 nM of a 250 bp DNA labeled antibody, and introducing the obtained reaction solution from an S well, was taken as 100%.

TABLE 2

| | Example (This invention) | | | Comparative Example (Conventional Method) | Reaction outside a capillary |
|---|---|---|---|---|---|
| Impressed Voltage | 2500 V | 625 V | 312 V | — | — |
| Reaction Time | About 25 secs. | About 100 secs. | About 200 secs. | 120 secs. | 30 mins. |
| AFP Signal | 145 | 346 | 435 | — | 460 |
| Reaction Rate | 32% | 75% | 95% | 26% | 100% |

As is clear from Table 2, it is found that even in application of 2500 V (a reaction time of about 25 seconds), reaction rate equivalent to or over that in a conventional method can be obtained, and in the case of application of 625 V (a reaction time of about 100 seconds) showing nearly the same reaction time in a conventional method, significantly higher reaction rate than that in a conventional method can be obtained. Namely, it can be understood that by a method of the present invention a complex is formed in excellently higher reaction rate than in a conventional method.

Example 2

An Analyte (an Antigen)

The same one as in Example 1 was used.
[A Reaction Improvement CFS (a DNA Labeled Antibody]
 The same one as in Example 1 was used.
 [A labeled CFS (a fluorescence labeled antibody)]
 The same one as in Example 1 was used.
[A Capillary Chip]

A capillary chip having a layout shown in FIG. 6 was produced according to a method described in "Technology and application of microchemistry chip", T. Kitamori et al., published in 2004 (Maruzen Co., Ltd.) as follows:

Namely, a photo resist film was formed on Si film which was formed on a quartz substrate. This photo resist was exposed using a mask having a capillary design (layout) shown in FIG. 6 and developed. Si at the part, where a photo resist was removed by development, was removed by sputtering, and then wet etching was carried out using a solution of hydrogen fluoride to prepare a capillary channel groove (capillary) at the quartz substrate. After removing a photo resist and a Si film remained on the quartz substrate, said quartz substrate and a cover plate having a hole for a fluid reservoir were adhered together by an HF bonding technique to prepare a capillary chip.

In this connection, in FIG. 6, L1 and L2 show a well for introducing a leading buffer, and SR shows a well for introducing an electrophoresis sample, the $1^{st}$ reagent solution (a solution containing a 250 bp DNA labeled antibody) and $2^{nd}$ reagent solution (a solution containing a fluorescence labeled antibody), respectively.

[Electrophoresis]
(1) A Electrophoresis Sample

Leading buffers (containing 50 mM of Cl⁻ ion) each containing 0 nM, 0.8 nM, 4 nM, 20 nM, 50 nM and 100 nM of AFP were used as electrophoresis samples.

(2) The $1^{st}$ Reagent Solution (a Solution Containing a 250 bp DNA Labeling Antibody)

A leading buffer (containing 50 mM of Cl⁻ ion) containing 100 nM of a 250 bp DNA labeled antibody was used as the 1st reagent solution.

(3) The $2^{nd}$ Reagent Solution (a Solution Containing a Fluorescence Labeled Antibody)

A leading buffer (containing 50 mM of Cl⁻ ion) containing 400 nM of 250 bp of a fluorescence labeled antibody was used as the $2^{nd}$ reagent solution (4) Procedure of Electrophoresis
a) Introduction of an Electrophoresis Sample, the $1^{st}$ Reagent Solution and the $2^{nd}$ Reagent Solution After whole of the channel shown in FIG. 6 was filled with a leading buffer, 10 μL of the $2^{nd}$ reagent solution (a solution containing a fluorescence labeled antibody) was delivered by drops into an SR well, and by application of a pressure of −5 psi for 2 seconds onto an L1 well to introduce the $2^{nd}$ reagent solution were introduced into the channel. Then, the $2^{nd}$ reagent solution in the SR well was replaced by 10 μL of the electrophoresis sample (a solution containing AFP), and similarly by application of a pressure of −5 psi for 2 seconds to the L1 well the electrophoresis sample was introduced into the channel. Furthermore, the electrophoresis sample in the SR well was replaced by 10 μL of the $1^{st}$ reagent solution (a solution containing a 250 bp DMA labeled antibody), and by application of a pressure of −5 psi for 2 seconds onto the L1 well the $1^{st}$ reagent solution was introduced into the channel. By this procedure, the $2^{nd}$ reagent solution zone, an electrophoresis sample zone and the $1^{st}$ reagent solution zone were formed in the channel in the order from the downstream side. Arrangement relation of the electrophoresis sample, the $1^{st}$ reagent solution and the $2^{nd}$ reagent solution in a capillary was schematically shown in FIG. 7. In this connection, in FIG. 7, a vertical line area shows an arrangement area of the $1^{st}$ reagent solution, a shaded area shows the electrophoresis sample and a dotted area shows, the $2^{nd}$ reagent solution, respectively.

Subsequently, the $1^{st}$ reagent solution in the SR well was replaced by 10 μL of a trailing buffer containing 75 mM of HEPES, and by application of a pressure of −5 psi for 2 seconds onto the L1 well the trailing buffer was introduced and arranged at the upstream side of the $1^{st}$ reagent solution zone.

b) Concentration and Reaction

By applying a voltage of 312 V between the SR well and the L1 well (a well for introducing a leading buffer), a DNA labeled antibody in the $1^{st}$ reagent solution, AFP in the electrophoresis sample and a fluorescence labeled antibody in the $2^{nd}$ reagent solution were contacted, while concentrating these, to form a [fluorescence labeled antibody-AFP-250 bp DNA labeled antibody] immune complex at 10° C.

In this connection, reaction time is about 200 seconds.

c) Separation and Detection

When a [fluorescence labeled antibody-AFP-250 bp DNA labeled antibody] immune complex overtook through a crossing part of an L2 channel and a main channel, 2800 V was applied onto the L2 well and 300 V was applied onto an L1 well, for 100 seconds to separate and detect said immune complex.

In this connection, the detection was carried out by serial measurement of fluorescent intensity by laser excitation of 635 nm at a capillary part at 2 cm from the crossing part of the L2 channel, using a fluorescent microscope (BX-50, manufactured from KS Olympus Co., Ltd.)

[Results]

FIG. 8 shows relation (linearity) between AFP concentration and peak area, and FIG. 9 also shows relation (linearity) between AFP concentration and peak area, in the low AFP concentration region (results for using electrophoresis samples of an AFP concentration of 0 nM, 0.8 nM, 4 nM and 20 nM). In this connection, in FIGS. 8 and 9, vertical axis shows peak area and horizontal axis shows AFP concentration, respectively. In addition, as Comparative Example, the result obtained by similar detection as above after introducing a reaction solution obtained by reaction of a fluorescence labeled antibody, AFP and a 250 bp DNA labeled antibody at 10° C. for 30 minutes in advance outside the capillary from the SR well to the capillary, was also shown in FIGS. 8 and 9. In this connection, the final concentration of a fluorescence labeled antibody in the reaction was 200 nM, the final concentration of AFP was 0 nM. 0.8 nM, 4 nM, 20 nM, 50 nM or 100 nM, and the final concentration of a 250 bp DNA labeled antibody was 20 nM.

In FIGS. 8 and 9, • mark shows the result obtained by a method in Example 2 and ○ mark shows the result obtained by a method in Comparative Example, respectively. In addition, in FIG. 9, a solid line shows a regression line in the result obtained by method in Example 2 and a dotted line shows a regression lines in the result obtained by a method in Comparative Example, respectively.

From FIGS. 8 and 9, it is found that a peak of a [fluorescence labeled antibody-AFP-250 bp DNA labeled antibody] immune complex is observed and peak area thereof is proportional to AFP concentration. Particularly, in the case when an immune complex is formed in advance, and then electrophoresis treatment is carried out, the linearity is poor in the low AFP concentration region (the detection values lie beneath the regression line), whereas good linearity is found to be obtained in any of low and high concentration regions of AFP, in the case of the present invention, wherein an immune reaction is carried out in a capillary electrophoretically, and then electrophoresis treatment is carried out.

INDUSTRIAL APPLICABILITY

The present invention relates to a method for forming a complex between an analyte or an analogue thereof in a sample, and a substance formable a complex with said analyte or analogue thereof (a CFS), a method for separating a complex formed, and a CFS or an analogue not involved in formation of said complex, along with a method for measuring an analyte in a sample, based on the amount of a complex separated, or the amount of a CFS or an analogue not involved in formation of a complex.

In accordance with a method of the present invention, a reaction between an analyte or an analogue thereof in a solution, and a substance formable a complex with said analyte or analogue thereof (a CFS) in a solution, can be carried out in a short time and in high reaction efficiency. As a result, separation of a complex with a substance formable a complex with said analyte or analogue thereof (a CFS), and a CFS or an analogue not involved in formation of a complex becomes possible rapidly, simply and in high accuracy, and furthermore, high sensitivity measurement of an analyte in a sample becomes possible, based on the amount of separated complex or the amount of a CFS or analogue not involved in formation of a complex.

Figure 1:
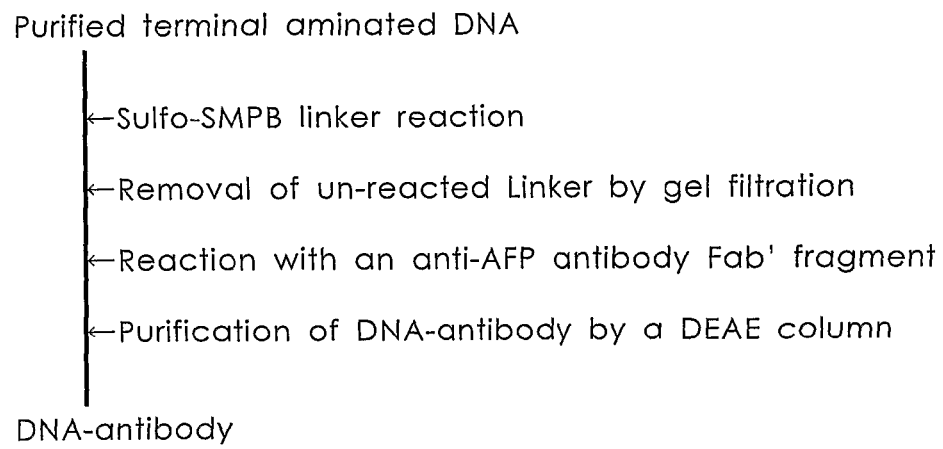
FIG. 1 shows a preparation scheme of a DNA labeled antibody [an anti-AFP antibody WA1 Fab' fragment bound with a 250 bp DNA fragment (a reaction improvement CFS)], prepared in Example 1.
Figure 2:
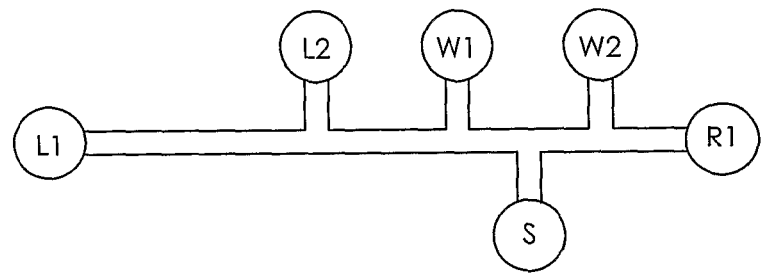
FIG. 2 shows a layout of a capillary chip prepared in Example 1.
Figure 3:
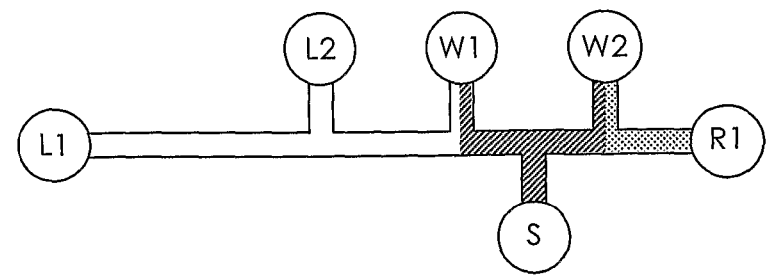
FIG. 3 shows an arrangement relation of an electrophoresis sample and a reagent solution introduced in a capillary in Example 1.
Figure 4:
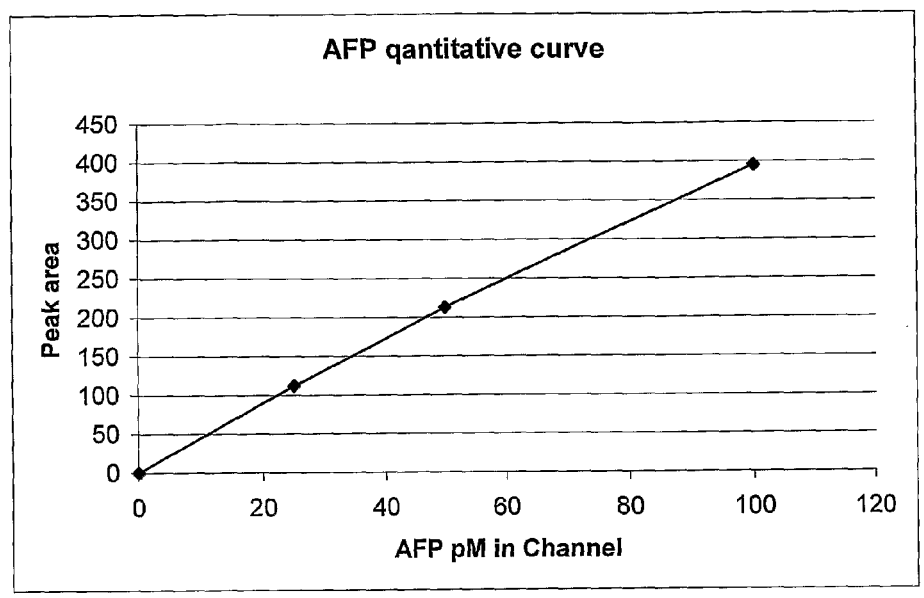
FIG. 4 shows a relation (linearity) between AFP concentration and peak area, obtained in Example 1.
Figure 5:
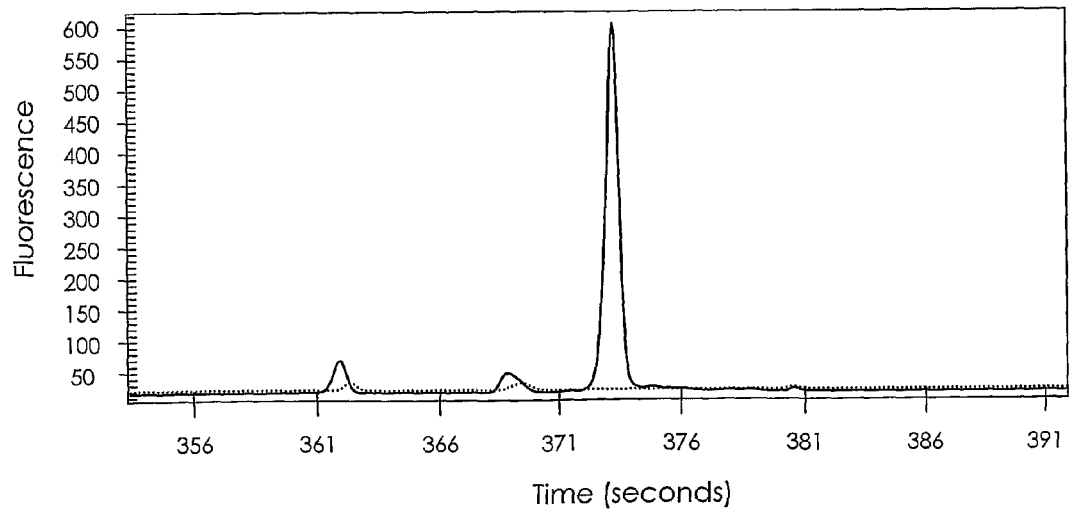
FIG. 5 shows electrophoresis chromatograms in the cases of using electrophoresis samples with AFP concentrations of 0 pM and 100 pM, obtained in Example 1.
Figure 6:
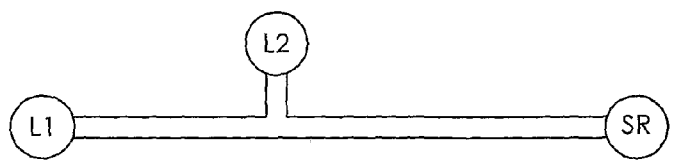
FIG. 6 shows a layout of a capillary chip prepared in Example 2.
Figure 7:
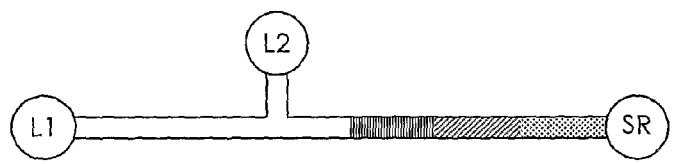
FIG. 7 shows an arrangement relation of an electrophoresis sample, the $1^{st}$ test sample and the $2^{nd}$ reagent solution introduced in a capillary in Example 2.
Figure 8:
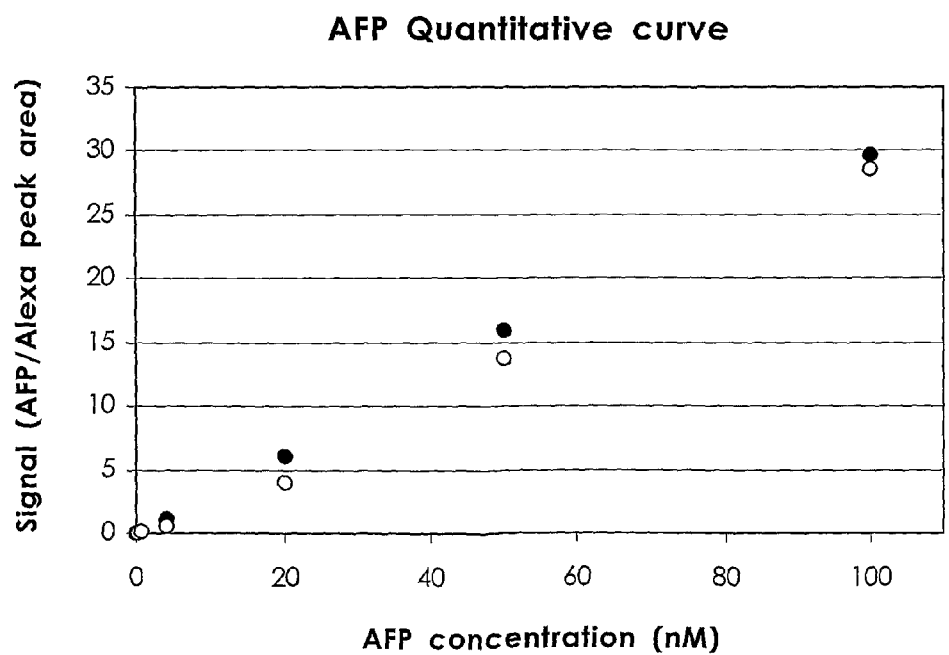
FIG. 8 shows a relation (linearity) between AFP concentration and peak area, obtained in Example 2.
Figure 9:
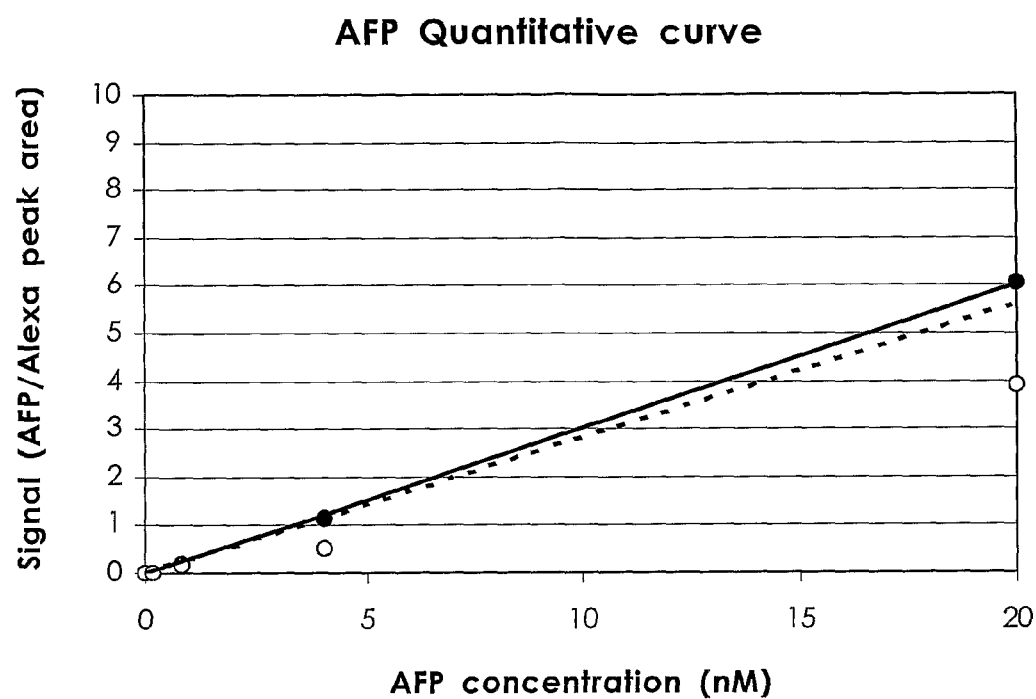
FIG. 9 shows a relation (linearity) between AFP concentration and peak area in low AFP concentration regions (results for using electrophoresis samples of an AFP concentration of 0 nM, 0.8 nM, 4 nM and 20 nM), obtained in Example 2.

The invention claimed is:

1. A method for separating a complex comprising the following steps:
(1) a step of arranging (a) a solution containing an analyte or an analogue thereof and (b) a solution containing not less than one kind of a substance capable of forming the complex with said analyte or said analogue thereof (the complex forming substance), each of (a) and (b) in a separate zone in a capillary, so that by applying a voltage to said capillary the complex between said analyte or said analogue thereof and the complex forming substance are formed without mixing these solutions in advance;
(2) a step of forming the complex by electrophoretically concentrating said analyte or said analogue thereof and/or the complex forming substance by utilizing a difference in their electrophoretic mobility wherein said analyte or said analogue thereof and/or said complex forming substance are gathered on application of a voltage onto a capillary by applying a voltage to said capillary, before these solutions are uniformly mixed to form the complex between said analyte or said analogue thereof and the complex forming substance; and
(3) a step of separating said complex, and the complex forming substance not involved in the formation of said complex or the analogue not involved in the formation of said complex by further electrical movement by using a different principle of electrophoresis from that in step (2),
wherein step (2) is carried out by ITP (isotachophoresis) or FASS (Field Amplification Sample Stacking).

2. The method according to claim 1, wherein at least said analyte after the applied voltage is concentrated by not less than 1.5 times said analyte before the applied voltage as a result of the application of voltage in step (2), said analogue after the applied voltage is concentrated by not less than 1.5 times said analogue before the applied voltage as a result of the application of voltage in step (2), or said at least one kind of the complex forming substances after the applied voltage is concentrated by not less than 1.5 times said complex forming substance before the applied voltage as a result of the application of voltage in step (2).

3. The method according to claim 1, wherein not less than one kind of the complex forming substance is one bound with a labeling substance and/or a reaction improvement substance capable of changing electrophoretic mobility of said analyte or said analogue thereof.

4. The method according to claim 1, wherein not less than two kinds of complex forming substances are used, and not less than two kinds of solutions containing each of such complex forming substances are used, and (1) at least one kind of the complex forming substances is one bound with a labeling substance, and at least one kind of the other complex forming substance is one bound with a reaction improvement substance capable of changing electrophoretic mobility of said analyte or said analogue thereof, or (2) at least one kind of the complex forming substance is one bound with a labeling substance and a reaction improvement substance capable of changing electrophoretic mobility of said analyte or said analogue thereof.

5. The method according to claim 1, wherein one kind of the complex forming substances is an antibody to said analyte or said analogue thereof, or protein binding to said analyte or said analogue thereof.

6. The method according to claim 1, wherein in step (1), a solution containing a substance with a higher electrophoretic mobility is arranged upstream of a solution containing a substance with lower electrophoretic mobility.

7. The method according to claim 1, wherein step (3) is carried out at a separation region independent of a part where step (2) is carried out in said capillary.

8. The method according to claim 1, wherein step (3) is carried out by capillary gel electrophoresis method.

9. The method according to claim 1, wherein said analogue is one bound with a labeling substance or a reaction improvement substance capable of changing electrophoretic mobility of said analyte or said analogue thereof.

10. The method according to claim 1, wherein step (1) is carried out by applying a voltage onto the capillary, increasing and/or reducing pressure in the capillary and/or relying on capillary phenomenon.

11. A method for separating a complex comprising the following steps:
(1) a step of arranging (a) a solution containing an analyte or an analogue thereof and (b) a solution containing not less than one kind of a substance capable of forming the complex with said analyte or said analogue thereof (the complex forming substance), each of (a) and (b) in a separate zone in a capillary, so that by applying a voltage to said capillary the complex between said analyte or said analogue thereof and the complex forming substance are formed without mixing these solutions in advance;
(2) a step of forming the complex by electrophoretically concentrating said analyte or said analogue thereof and/or the complex forming substance by utilizing a difference in their electrophoretic mobility wherein said analyte or said analogue thereof and/or said complex forming substance are gathered on application of a voltage onto a capillary by applying a voltage to said capillary, before these solutions are uniformly mixed to form the complex between said analyte or said analogue thereof and the complex forming substance;
(3) a step of separating said complex, and the complex forming substance not involved in the formation of said complex or the analogue not involved in the formation of said complex by further electrical movement by using a different principle of electrophoresis from that in step (2); and
(4) a step of measuring the amount of thus separated complex, and/or the amount of the complex forming substance and/or the analogue not involved in the formation of said complex to determine the amount of said analyte based on the result,
wherein step (2) is carried out by ITP (isotachophoresis) or FASS (Field Amplification Sample Stacking).

12. The method according to claim 11, wherein at least said analyte after the applied voltage is concentrated by not less than 1.5 times said analyte before the applied voltage as a result of the application of voltage in step (2), said analogue after the applied voltage is concentrated by not less than 1.5 times said analogue before the applied voltage as a result of the application of voltage in step (2), or said at least one kind of the complex forming substances after the applied voltage is concentrated by not less than 1.5 times said complex forming substance before the applied voltage as a result of the application of voltage in step (2).

13. The method according to claim 11, wherein not less than one kind of the complex forming substance is one bound with a labeling substance and/or a reaction improvement substance capable of changing electrophoretic mobility of said analyte or said analogue thereof.

14. The method according to claim 11, wherein not less than two kinds of complex forming substances are used, and not less than two kinds of solutions containing each of such complex forming substances are used, and (1) at least one kind of the complex forming substances is one bound with a labeling substance, and at least one kind of the other complex forming substance is one bound with a reaction improvement substance capable of changing electrophoretic mobility of said analyte or said analogue thereof, or (2) at least one kind of the complex forming substance is one bound with a labeling substance and a reaction improvement substance capable of changing electrophoretic mobility of said analyte or said analogue thereof.

15. The method according to claim 11, wherein one kind of the complex forming substances is an antibody to said analyte or said analogue thereof, or protein binding to said analyte or said analogue thereof.

16. The method according to claim 11, wherein in step (1), among said solutions, a solution containing a substance with a higher electrophoretic mobility is arranged upstream of a solution containing a substance with lower electrophoretic mobility.

17. The method according to claim 11, wherein step (3) is carried out at a separation region independent of a part where step (2) is carried out in said capillary.

18. The method according to claim 11, wherein step (3) is carried out by capillary gel electrophoresis method.

19. The method according to claim 11, wherein said analogue is one bound with a labeling substance or a reaction improvement substance capable of changing electrophoretic mobility of said analyte or said analogue thereof.

* * * * *